US007893048B2

(12) United States Patent
Alenfalk et al.

(10) Patent No.: US 7,893,048 B2

(45) Date of Patent: Feb. 22, 2011

(54) 2-AZETIDINONE DERIVATIVES AS CHOLESTEROL ABSORPTION INHIBITORS FOR THE TREATMENT OF HYPERLIPIDAEMIC CONDITIONS

(75) Inventors: Susanne Alenfalk, Molndal (SE); Mikael Dahlstrom, Molndal (SE); Fana Hunegnaw, Molndal (SE); Staffan Karlsson, Molndal (SE); Malin Lemurell, Molndal (SE); Ingemar Starke, Molndal (SE)

(73) Assignee: AstraZeneca AB, Sodertalje (SE)

( * ) Notice: Subject to any disclaimer, the term of this patent is extended or adjusted under 35 U.S.C. 154(b) by 507 days.

(21) Appl. No.: 11/993,466

(22) PCT Filed: Jun. 21, 2006

(86) PCT No.: PCT/SE2006/000765

§ 371 (c)(1),
(2), (4) Date: Dec. 21, 2007

(87) PCT Pub. No.: WO2006/137796

PCT Pub. Date: Dec. 28, 2006

(65) Prior Publication Data

US 2010/0137273 A1 Jun. 3, 2010

(30) Foreign Application Priority Data

Jun. 22, 2005 (SE) .................................... 0501465

(51) Int. Cl.

| | |
|---|---|
| ***C07D 205/08*** | (2006.01) |
| ***C07D 405/12*** | (2006.01) |
| ***A61K 31/397*** | (2006.01) |
| ***A61P 3/06*** | (2006.01) |
| ***A61P 9/10*** | (2006.01) |
| *C07D 319/06* | (2006.01) |
| *C07D 413/14* | (2006.01) |

(52) U.S. Cl. .................. 514/210.02; 540/360; 548/230; 549/375

(58) Field of Classification Search ................. 540/360; 514/210.02
See application file for complete search history.

(56) References Cited

U.S. PATENT DOCUMENTS 5,306,817 A 4/1994 Thiruvengadam et al.
5,631,365 A 5/1997 Rosenblum et al.
5,633,246 A 5/1997 McKittrick et al.
5,661,145 A 8/1997 Davis
5,739,321 A 4/1998 Wu et al.
5,744,467 A 4/1998 McKittrick et al.
5,756,470 A 5/1998 Yumibe et al.
5,767,115 A 6/1998 Rosenblum et al.
5,846,966 A 12/1998 Rosenblum et al.
5,886,171 A 3/1999 Wu et al.
5,919,672 A 7/1999 Homann et al.
RE37,721 E 5/2002 Rosenblum et al.
7,235,543 B2 6/2007 Burnett et al.
7,368,562 B2 5/2008 Burnett et al.
7,470,678 B2 * 12/2008 Starke et al. ........... 514/210.09
2002/0137690 A1 9/2002 Ghosal et al.
2003/0119428 A1 6/2003 Davis et al.
2003/0119757 A1 6/2003 Davis
2004/0018060 A1 1/2004 Kaezek et al.
2004/0018061 A1 1/2004 Jansson
2004/0254369 A1 12/2004 Framroze
2005/0096307 A1 5/2005 Graziano
2005/0267049 A1 12/2005 Goulet et al.
2006/0046996 A1 3/2006 Aoki et al.
2006/0069080 A1 3/2006 Veltri
2007/0049748 A1 3/2007 Uppala et al.
2007/0078098 A1 4/2007 DeVita et al.
2007/0129540 A1 6/2007 Framroze et al.
2007/0142304 A1 * 6/2007 Alenfalk et al. ............... 514/19
2007/0155674 A1 7/2007 Burnett et al.
2007/0155675 A1 7/2007 Burnett et al.
2008/0064676 A1 * 3/2008 Alenfalk et al. ......... 514/210.02
2008/0070890 A1 * 3/2008 Burnett et al. .......... 514/210.05
2009/0069285 A1 * 3/2009 Lemurell et al. ........ 514/210.02
2010/0048529 A1 * 2/2010 Dahlstrom et al. ..... 514/210.02
2010/0048530 A1 * 2/2010 Dahlstrom et al. ..... 514/210.15
2010/0099657 A2 * 4/2010 Alenfalk et al. ......... 514/210.02
2010/0125059 A1 * 5/2010 Nakano et al. .......... 514/210.02
2010/0137273 A1 6/2010 Alenfalk et al.
2010/0152156 A1 * 6/2010 Dahlstrom et al. ..... 514/210.02

(Continued)

FOREIGN PATENT DOCUMENTS

EP 524595 1/1993

(Continued)

OTHER PUBLICATIONS

Office Action dated Jul. 15, 2009 received in copending U.S. Appl. No. 10/596,725.

(Continued)

*Primary Examiner*—Mark L Berch
(74) *Attorney, Agent, or Firm*—Pepper Hamilton LLP

(57) ABSTRACT

Compounds of formula (I): (wherein variable groups are as defined within) pharmaceutically acceptable salts, solvates, solvates of such salts and prodrugs thereof and their use as cholesterol absorption inhibitors for the treatment of hyperlipidaemia are described. Processes for their manufacture and pharmaceutical compositions containing them are also described.

(I)

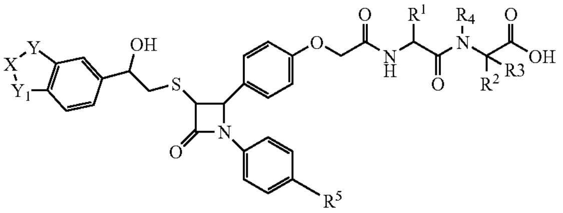

29 Claims, No Drawings

U.S. PATENT DOCUMENTS

| | | | | |
|---|---|---|---|---|
| 2010/0168075 | A1* | 7/2010 | Dahlstrom et al. | 514/210.02 |
| 2010/0216759 | A1* | 8/2010 | Alenfalk et al. | 514/210.02 |

FOREIGN PATENT DOCUMENTS

| | | |
|---|---|---|
| EP | 0792264 | 9/1997 |
| EP | 1362855 | 11/2003 |
| EP | 1413331 | 4/2004 |
| WO | 9302048 | 2/1993 |
| WO | 9414433 | 7/1994 |
| WO | 9417038 | 8/1994 |
| WO | 9501961 | 1/1995 |
| WO | 9508532 | 3/1995 |
| WO | 9526334 | 10/1995 |
| WO | 9535277 | 12/1995 |
| WO | 9609827 | 4/1996 |
| WO | 9616037 | 5/1996 |
| WO | 9619450 | 6/1996 |
| WO | 9716424 | 5/1997 |
| WO | 9716455 | 5/1997 |
| WO | 9745406 | 12/1997 |
| WO | 0020623 | 4/2000 |
| WO | 0034240 | 6/2000 |
| WO | 0038725 | 7/2000 |
| WO | 0060107 | 10/2000 |
| WO | 0063703 | 10/2000 |
| WO | 0266464 | 2/2002 |
| WO | 0218432 | 3/2002 |
| WO | 0250027 | 6/2002 |
| WO | 0250060 | 6/2002 |
| WO | 0250068 | 6/2002 |
| WO | 0250090 | 6/2002 |
| WO | 02058685 | 8/2002 |
| WO | 02058696 | 8/2002 |
| WO | 02058731 | 8/2002 |
| WO | 02058732 | 8/2002 |
| WO | 02058733 | 8/2002 |
| WO | 02058734 | 8/2002 |
| WO | 02072104 | 9/2002 |
| WO | 02079174 | 10/2002 |
| WO | 02096415 | 12/2002 |
| WO | 03026643 | 4/2003 |
| WO | 03026644 | 4/2003 |
| WO | 03088962 | 10/2003 |
| WO | 2004000803 | 12/2003 |
| WO | 2004000804 | 12/2003 |
| WO | 2004000805 | 12/2003 |
| WO | 2004005247 | 1/2004 |
| WO | 2004010948 | 2/2004 |
| WO | 2004010993 | 2/2004 |
| WO | 2004014947 | 2/2004 |
| WO | 2004003457 | 5/2004 |
| WO | 2004043456 | 5/2004 |
| WO | 2004081002 | 9/2004 |
| WO | 2004099132 | 11/2004 |
| WO | 2004107958 | 12/2004 |
| WO | 2005000353 | 1/2005 |
| WO | 2005021495 | 3/2005 |
| WO | 2005021497 | 3/2005 |
| WO | 2005033100 | 4/2005 |
| WO | 2005042692 | 5/2005 |
| WO | 2005044256 | 5/2005 |
| WO | 2005047248 | 5/2005 |
| WO | 2005049592 | 6/2005 |
| WO | 2005058316 | 6/2005 |
| WO | 2005061451 | 7/2005 |
| WO | 2005061452 | 7/2005 |
| WO | 2005062824 | 7/2005 |
| WO | 2005062897 | 7/2005 |
| WO | 2005066120 | 7/2005 |
| WO | 2005067903 | 7/2005 |
| WO | 2005069900 | 8/2005 |
| WO | 2005113495 | 12/2005 |
| WO | 2005113496 | 12/2005 |
| WO | 2006017257 | 2/2006 |
| WO | 2006060808 | 6/2006 |
| WO | 2006068990 | 6/2006 |
| WO | 2006072957 | 7/2006 |
| WO | 2006086562 | 8/2006 |
| WO | 2006102674 | 9/2006 |
| WO | 2006107936 | 10/2006 |
| WO | 2006116499 | 11/2006 |
| WO | 2006121861 | 11/2006 |
| WO | 2006122186 | 11/2006 |
| WO | 2006122216 | 11/2006 |
| WO | 2006124713 | 11/2006 |
| WO | 2006127893 | 11/2006 |
| WO | 2006134604 | 12/2006 |
| WO | 2006137080 | 12/2006 |
| WO | 2006137782 | 12/2006 |
| WO | 2006137792 | 12/2006 |
| WO | 2006137793 | 12/2006 |
| WO | 2006137794 | 12/2006 |
| WO | 2006137795 | 12/2006 |
| WO | 2006137796 | 12/2006 |
| WO | 2006137797 | 12/2006 |
| WO | 2006138163 | 12/2006 |
| WO | 2007003365 | 1/2007 |
| WO | 2007008529 | 1/2007 |
| WO | 2007008541 | 1/2007 |
| WO | 2007015161 | 2/2007 |
| WO | 2007016643 | 2/2007 |
| WO | 2007017705 | 2/2007 |
| WO | 2007030721 | 3/2007 |
| WO | 2007058335 | 5/2007 |
| WO | 2007059871 | 5/2007 |
| WO | 2007072088 | 6/2007 |
| WO | 2007075702 | 7/2007 |

OTHER PUBLICATIONS

Clader et al., "2-Azetidinone Cholesterol Absorption Inhibitors: Structure-Activity Relationships on the Heterocyclic Nucleus," J. Med Chem (1996) 39:3684-3693.

McKittrick et al., Stereoselective synthesis and biological activity of cis azetidinones as cholesterol absorption inhibitors, Bioorganic & Medicinal Chemistry Letters (1996) 6(16):1947-1950.

Burnett et al., "2-Azetidinones as Inhibitors of Cholesterol Absorption," J. Med Chem (1994) 12:1733-1736.

Castaner et al., "Ezetimibe," Drugs of the Future (2000) 25(7):679-685.

Vaccaro et al., "Sugar-substituted 2-azetidinone cholesterol absorption inhibitors: Enhanced potency by modification of the sugar," Bioorganic & Medicinal Chemistry Letters (1998) 8:313-318.

Fu et al., "Process for preparing Ezetimibe intermediate by an acid enhanced chemo- and enantioselective CBS catalyzed ketone reduction," Tetrahedron Letters (2003) 44:801-804.

Kirkup et al., "(−)-SCH 57939: synthesis and pharmacological properties of a potent, metabolically stable cholesterol absorption inhibitor," Bioorganic & Medicinal Chemistry Letters (1996) 6(17):2069-2072.

Vaccaro et al., "Carboxy-substituted 2-azetidinones as cholesterol absorption inhibitors," Bioorganic & Medicinal Chemistry Letters (1998) 8:319-322.

Rosenblum et al., "Discovery of 1-(4-fluorophenyl)-(3R)-[3-(4-fluorophenyl)-(3S)-hydroxypropyl]-(4S)-(4-hydroxyphenyl)-2-azetidinone (SCH 58235): a designed, potent, orally active inhibitor of cholesterol absorption.," J. Med Chem (1998) 41:973-980.

Wu et al., "A Novel One-Step Diastereo- and Enantioselective Formation of trans-Azetidinones and Its Application to the Total Synthesis of Cholesterol Absorption Inhibitors," J. Org. Chem (1999) 64:3714-3718.

Kvaerno et al., "Synthesis and in vitro evaluation of inhibitors of intestinal cholesterol absorption," J Med Chem (2005) 48(19):6035-6053.
Burnett "Beta-lactam cholesterol absorption inhibitors," Curr Med Chem (2004) 11:1873-1887.
Seedorf et al., "Cholesterol absorption inhibitor ezetimibe blocks uptake of oxidized LDL in human macrophages," Biochem Biophys Research Commun (2004) 320(4):1337-1341.
Kvaerno et al., "An in vitro assay for evaluation of small-molecule inhibitors of cholesterol absorption," (2004) 43 (35):4653-4656.
Clader "Ezetimibe and other azetidinone cholesterol absorption inhibitors of cholesterol absorption," Curr Topics in Med Chem (2005) 5 (3):243-256.
Garcia-Calvo et al., "The target of ezetimibe is Niemann-Pick C1-Like 1 (NPC1L1)," PNAS (2005) 102(23):8132-8137.
Ritter et al., "Heterocyclic ring scaffolds as small-molecule cholesterol absorption inhibitors," Org Biomol Chem (2005) 3:3514-3523.
Dugar et al., "Gamma-lactams and related compounds as cholesterol absorption inhibitors: homologs of the beta-lactam cholesterol absorption inhibitor SCH 48461," Bioorganic & Medicinal Letters (1995) 5(24):2947-2952.
Mounsey et al., "Diet may slow progression of diabetic nephropathy," The Journal of Family Practice (2003) 52 (9):672-673.
Sobieszczyk et al., "Acute pulmonary embolism: don't ignore the platelet," Circulation (2002) 106(14):1748-1749.
Journal of the American College of Cardiology (2000) 35(1):252A.
van Heek et al., "Comparison of the activity and disposition of the novel cholesterol absorption inhibitor, SCH58235, and its glucuronide, SCH60663," Br. J. Pharmcol (2000) 129(8):1748-1754.
Yang et al., "Allelic Variants in Long-QT Disease Genes in Patients With Drug-Associated Torsades de Pointes," Circulation (2002) 105(16):1943-1948.
Zaks et al., Enzymatic glucuronidation of a novel cholesterol absorption inhibitor, Sch 58235, Appl Biochem Biotechnol. (1998) 73(2-3):205-214.
Clader "The discovery of ezetimibe: a view from outside the receptor," J Med Chem (2004) 47(1):1-9.
Altmann et al., "Niemann-pick C1 like 1 protein is critical for intestinal cholesterol absorption," Science (2004) 303:1201-1204.
Notice of allowance dated Jul. 31, 2008 for U.S. Appl. No. 10/519,897.
Office Action dated Feb. 28, 2008 for U.S. Appl. No. 10/519,897.
Notice of allowance dated Aug. 28, 2007 for U.S. Appl. No. 10/519,897.
Office Action dated May 1, 2007 for U.S. Appl. No. 10/519,897.
Albert "Chemical aspects of selective toxicity," Nature (1958) pp. 421-423.
Office Action dated May 3, 2010 received in copending U.S. Appl. No. 10/596,731.
McKittrick et al., "Synthesis of C3 heteroatom-substituted azetidinones that display potent cholesterol absorption inhibitory activity," J Med Chem (1998) 41(5):752-9.
Office Action dated Sep. 17, 2009 received in copending U.S. Appl. No. 10/596,731.
Notice of Allowance dated Sep. 8, 2010 received in copending U.S. Appl. No. 11/993,033.
Non Final Office Action received in copendinng U.S. Appl. No. 11/993,033 dated Jun. 10, 2010.
Non Final Office Action received in copending U.S. Appl. No. 11/993,463 dated Jun. 7, 2010.
Notice of Allowance and Fee(s) Due received in copending U.S. Appl. No. 10/596,731 dated May 27, 2010.
Office Action dated Jun. 4, 2010 received in copending U.S. Appl. No. 11/993,484.
Office Action dated Jun. 9, 2010 received in copending U.S. Appl. No. 11/993,479.
Office Action dated Jun. 9, 2010 received in copending U.S. Appl. No. 11/993,475.
Office Action dated Jun. 10, 2010 received in copending U.S. Appl. No. 11/993,470.
Notice of Allowance dated Nov. 10, 2010 received in copending U.S. Appl. No. 11/993,463.

* cited by examiner

2-AZETIDINONE DERIVATIVES AS CHOLESTEROL ABSORPTION INHIBITORS FOR THE TREATMENT OF HYPERLIPIDAEMIC CONDITIONS

CROSS-REFERENCE TO RELATED APPLICATIONS

This application is the U.S. National Stage filing of International Application Serial No. PCT/SE2006/000765 filed Jun. 21, 2006, which claims priority to Swedish Application Serial No. 0501465-9 filed Jun. 22, 2005, each of which is incorporated herein by reference in its entirety.

This invention relates to 2-azetidinone derivatives, or pharmaceutically acceptable salts, solvates, solvates of such salts and prodrugs thereof. These 2-azetidinones possess cholesterol absorption inhibitory activity and are accordingly of value in the treatment of disease states associated with hyperlipidaemic conditions. They are therefore useful in methods of treatment of a warm-blooded animal, such as man. The invention also relates to processes for the manufacture of said 2-azetidinone derivatives, to pharmaceutical compositions containing them and to their use in the manufacture of medicaments to inhibit cholesterol absorption in a warm-blooded animal, such as man. A further aspect of this invention relates to the use of the compounds of the invention in the treatment of dyslipidemic conditions.

Atherosclerotic coronary artery disease is a major cause of death and morbidity in the western world as well as a significant drain on healthcare resources. It is well-known that hyperlipidaemic conditions associated with elevated concentrations of total cholesterol and low density lipoprotein (LDL) cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930-1938 and "Diabetes and Cardiovascular Disease: A Statement for Healthcare Professionals from the American Heart Association" Grundy S, Benjamin I., Burke G., et al; Circulation, 1999, 100, 1134-46).

Sitosterolemia is a lipid storage disorder characterised by increased levels of sitosterol and other plant sterols in the plasma and other tissues due to increased non-selective intestinal absorption of sterols and decreased hepatic removal. Sitosterolemia can result in accelerated atherosclerosis and other cardiovascular diseases. See WO 02/058696.

The concentration of plasma cholesterol depends on the integrated balance of endogenous and exogenous pathways of cholesterol metabolism. In the endogenous pathway, cholesterol is synthesized by the liver and extra hepatic tissues and enters the circulation as lipoproteins or is secreted into bile. In the exogenous pathway cholesterol from dietary and biliary sources is absorbed in the intestine and enters the circulation as component of chylomicrons. Alteration of either pathway will affect the plasma concentration of cholesterol.

The precise mechanism by which cholesterol is absorbed from the intestine is however not clear.

A clear association between reduction of total cholesterol and (LDL) cholesterol and decreased instance of coronary artery disease has been established, and several classes of pharmaceutical agents are used to control serum cholesterol. The major options to regulate plasma cholesterol include (i) blocking the synthesis of cholesterol by agents such as HMG-CoA reductase inhibitors, for example statins such as simvastatin and fluvastatin, which also by up-regulation of LDL-receptors will promote the cholesterol removal from the plasma; (ii) blocking the bile acid reabsorption by specific agents resulting in increased bile acid excretion and synthesis of bile acids from cholesterol with agents such as bile acid binders, such as resins e.g. cholestyramine and cholestipol; and (iii) by blocking the intestinal uptake of cholesterol by selective cholesterol absorption inhibitors. High density lipoprotein (HDL) elevating agents such as fibrates and nicotinic acid analogues have also been employed.

Compounds possessing such cholesterol absorption inhibitory activity have been described, see for instance the compounds described in WO 93/02048, WO 94/17038, WO 95/08532, WO 95/26334, WO 95/35277, WO 96/16037, WO 96/19450, WO 97/16455, WO 02/50027, WO 02/50060, WO 02/50068, WO 02/50090, WO 02/66464, WO 04/000803, WO 04/000804, WO04/000805, WO04/01993, WO04/010948, WO04/043456 WO 04/043457, WO 04/081002, WO05/000353, WO05/021495, WO05/021497, WO05/033100, U.S. Pat. No. 5,756,470, U.S. Pat. No. 5,767,115, US 20040180860, US20040180861 and U.S. RE 37,721.

The present invention is based on the discovery that certain 2-azetidinone derivatives surprisingly inhibit cholesterol absorption. Such properties are expected to be of value in the treatment of disease states associated with hyperlipidaemic conditions. The compounds of the present invention are not disclosed in any of the above applications and we have surprisingly found that the compounds of the present invention possess beneficial efficacious, metabolic and toxicological profiles that make them particularly suitable for in vivo administration to a warm blooded animal, such as man. In particular certain compounds of the present invention have a low degree of absorption compared to compounds of the prior art whilst retaining their ability to inhibit cholesterol absorption.

Accordingly there is provided a compound of formula (I):

A compound of formula (I):

(I)

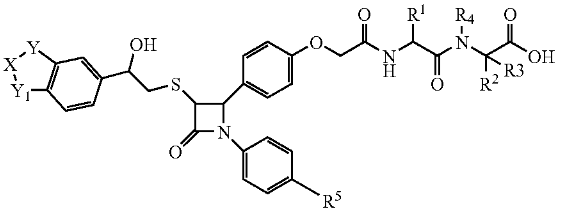

Wherein:

X=$-CH_2-$, $-CH_2CH_2-$, $-CH_2CH_2CH_2-$;

$R^1$=H, $C_{1-6}$ alkyl, $C_{3-6}$cycloalkyl or aryl;

$R^2$ and $R^3$ is hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, (C1-C4 alkyl)$_3$Si, N—($C_{1-6}$alkyl)amino, N,N—($C_{1-6}$alkyl)$_2$-amino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, cyano, $C_{1-6}$alkyl, $C_{1-6}$alkoxy or;

$R^4$ is hydrogen, $C_{1-6}$ alkyl, or aryl$C_{1-6}$ alkyl;

wherein $R^3$ and $R^2$ may form a ring with 3-7 carbon atoms and wherein $R^4$ and $R^2$ may form a ring with 2-6 carbon atoms;

$R^5$ is selected from halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl; and wherein n is 0, 1, 2 or 3.

According to embodiments of the invention X can be —$CH_2$—, $CH_2CH_2$—, or —$CH_2CH_2CH_2$—.

Further the invention provides for a compound of formula (I2):

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include benzyl, 1-phenylethyl and 2-phenylethyl. The term "halo" refers to fluoro, chloro, bromo and iodo.

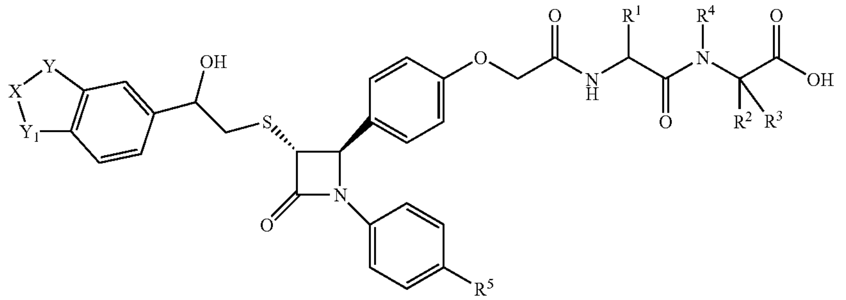

(I2)

The substituents in the compound according to formula (I2) is the same as for the compound according to formula (I) as described above.

According to an embodiment of the invention $R^1$ is hydrogen;

$R^2$ and $R^3$ are hydrogen or a branched or unbranched $C_{1-6}$alkyl; wherein said $C_{1-6}$alkyl is substituted by $C_{3-6}$cycloalkyl, aryl or amino; and $R^4$ is hydrogen.

According to an embodiment of the invention $R^1$ is hydrogen;

$R^2$ and $R^3$ are hydrogen or a branched or unbranched $C_{1-6}$alkyl; wherein said $C_{1-6}$alkyl is substituted by $C_{3-6}$cycloalkyl;

$R^4$ is hydrogen.

According to an embodiment of the invention, $R^2$ is hydrogen and $R^3$ is tert-butyl.

According to an embodiment of the invention, $R^2$ is hydrogen and $R^3$ is methyl; wherein said methyl is substituted by cyclohexyl.

According to an embodiment of the invention, $R^5$ is selected from chlorine or fluorine.

The invention further provides for a compound chosen from:

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-D-lysine;

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-b,b-dimethyl-D-phenylalanine; and N-({4-[(2R,3R)-3-{[(2R or S)-2-(2,3-Dihydro-1-benzofuran-5-yl)-2-hydroxyethyl]thio}-1-(4-fluorophenyl)-4-oxoazetidin-2-yl]phenoxy}acetyl)glycyl-3-cyclohexyl-D-alanine ammoniate.

Where optional substituents are chosen from "one or more" groups it is to be understood that this definition includes all substituents being chosen from one of the specified groups or the substituents being chosen from two or more of the specified groups.

The term "aryl" refers to a 4-10 membered aromatic mono or bicyclic ring containing 0 to 5 heteroatoms independently selected from nitrogen, oxygen or sulphur. Examples of aryls include phenyl, pyrrolyl, furanyl, imidazolyl, triazolyl, tetrazolyl, pyrazinyl, pyrimidinyl, pyridazinyl, pyridyl, isoxazolyl, oxazolyl, 1,2,4 oxadiazolyl, isothiazolyl, thiazolyl, 1,2,4-triazolyl, thienyl, naphthyl, benzofuranyl, benzimidazolyl, benzthienyl, benzthiazolyl, benzisothiazolyl, benzoxazolyl, benzisoxazolyl, 1,3-benzodioxolyl, indolyl, pyridoimidazolyl, pyrimidoimidazolyl, quinolyl, isoquinolyl, quinoxalinyl, quinazolinyl, phthalazinyl, cinnolinyl and naphthyridinyl. Particularly "aryl" refers to phenyl, thienyl, pyridyl, imidazolyl or indolyl. The term"aryl" includes both unsubstituted and substituted aromatic rings.

Examples of "$C_{1-6}$alkoxy" include methoxy, ethoxy and propoxy. Examples of "$C_{1-6}$alkylS(O)$_a$ wherein a is 0 to 2" include methylthio, ethylthio, methylsulphinyl, ethylsulphinyl, mesyl and ethylsulphonyl. Examples of "N—($C_{1-6}$alkyl)amino" include methylamino and ethylamino. Examples of "N,N—($C_{1-6}$alkyl)$_2$-amino" include di-N-methylamino, di-(N-ethyl)amino and N-ethyl-N-methylamino. "$C_{3-6}$cycloalkyl" refers to cyclopropyl, cyclobutyl, cyclopentyl and cyclohexyl.

A suitable pharmaceutically acceptable salt of a compound of the invention, or other compounds disclosed herein, is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I), or other compounds disclosed herein, may be administered in the form of a pro-drug which is broken down in the human or animal body to give a compound of the formula (I). Examples of pro-drugs include in vivo hydrolysable esters and in vivo hydrolysable amides of a compound of the formula (I).

An in vivo hydrolysable ester of a compound of the formula (I), or other compounds disclosed herein, containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I), or other compounds disclosed herein, containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I), or other compounds disclosed herein, containing a carboxy group is, for example, a N—$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess cholesterol absorption inhibitory activity.

The invention relates to any and all tautomeric forms of the compounds of the formula (I) that possess cholesterol absorption inhibitory activity.

It is also to be understood that certain compounds of the formula (I) can exist in solvated as well as unsolvated forms such as, for example, hydrated forms. It is to be understood that the invention encompasses all such solvated forms, which possess cholesterol absorption inhibitory activity.

Preferred aspects of the invention are those, which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1) Reacting a Compound of Formula (II):

(II)

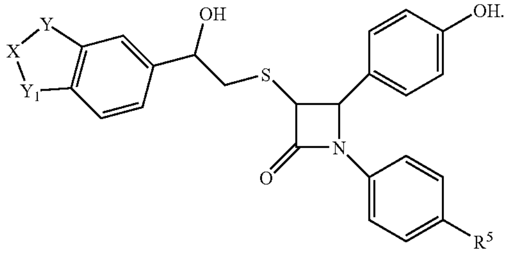

with a compound of formula (III):

(III)

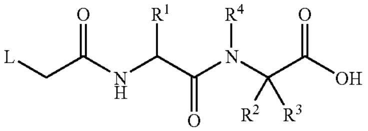

wherein L is a displaceable group;

Process 2) Reacting an Acid of Formula (IV):

(IV)

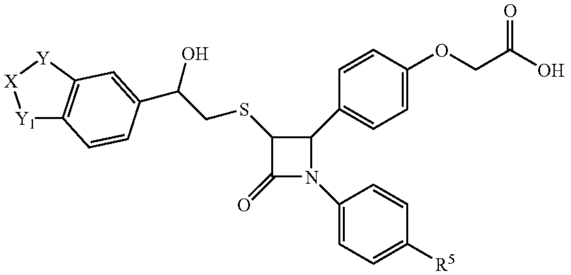

or an activated derivative thereof; with an amine of formula (V):

(V)

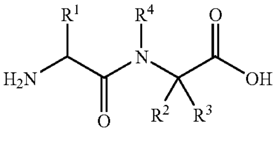

Process 3): Reacting an Acid of Formula (VI):

(VI)

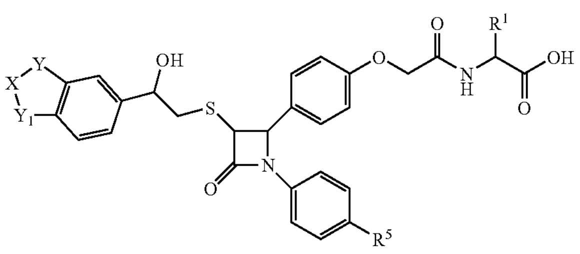

or an activated derivative thereof, with an amine of formula (VII):

(VII)

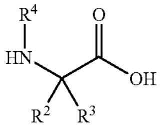

Process 4): Reducing a Compound of Formula (VIII):

with a compound of formula (X):

(X)

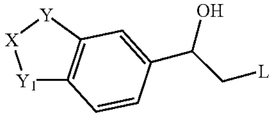

wherein L is a displaceable group;

Process 6): Reacting a Compound of Formula (XI):

(XI)

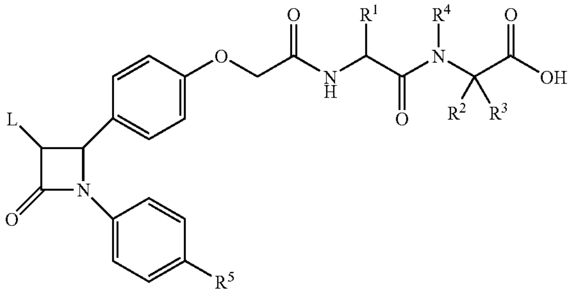

(VIII)

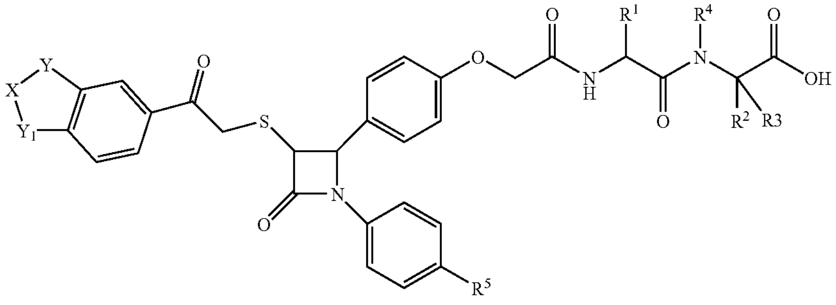

Process 5): Reacting a Compound of Formula (IX):

(IX)

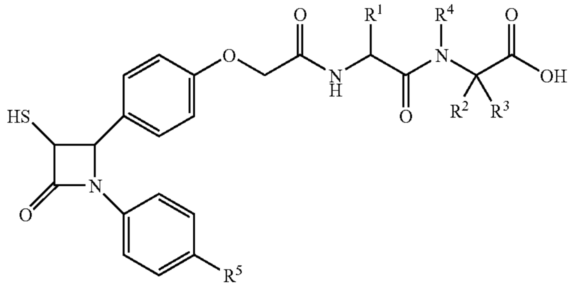

wherein L is a displaceable group; with a compound of formula (XII):

(XII)

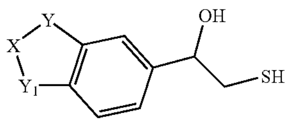

Process 7): De-Esterifying a Compound of Formula (XIII)

(XIII)

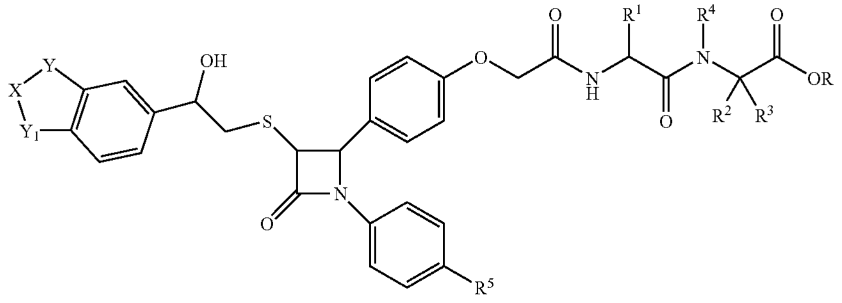

wherein the group C(O)OR is an ester group;

and thereafter if necessary or desirable:

i) converting a compound of the formula (I) into another compound of the formula (I);

ii) removing any protecting groups;

iii) forming a pharmaceutically acceptable salt, solvate, solvate of such a salt or a prodrug; or iv) separating two or more enantiomers.

L is a displaceable group, suitable values for L are for example, a halogeno or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B1. Alternatively they can be prepared by the following reactions.

Process 1): Alcohols of formula (II) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (II) may be prepared according to the following scheme:

Scheme 1

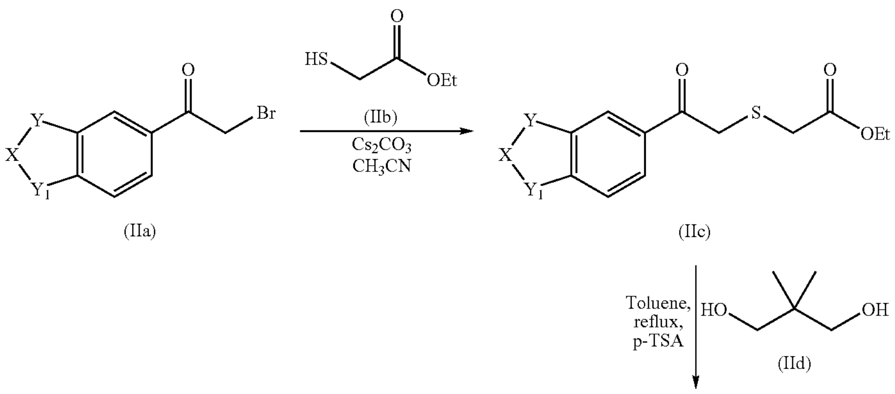

(IIa) (IIc) (IId)

-continued
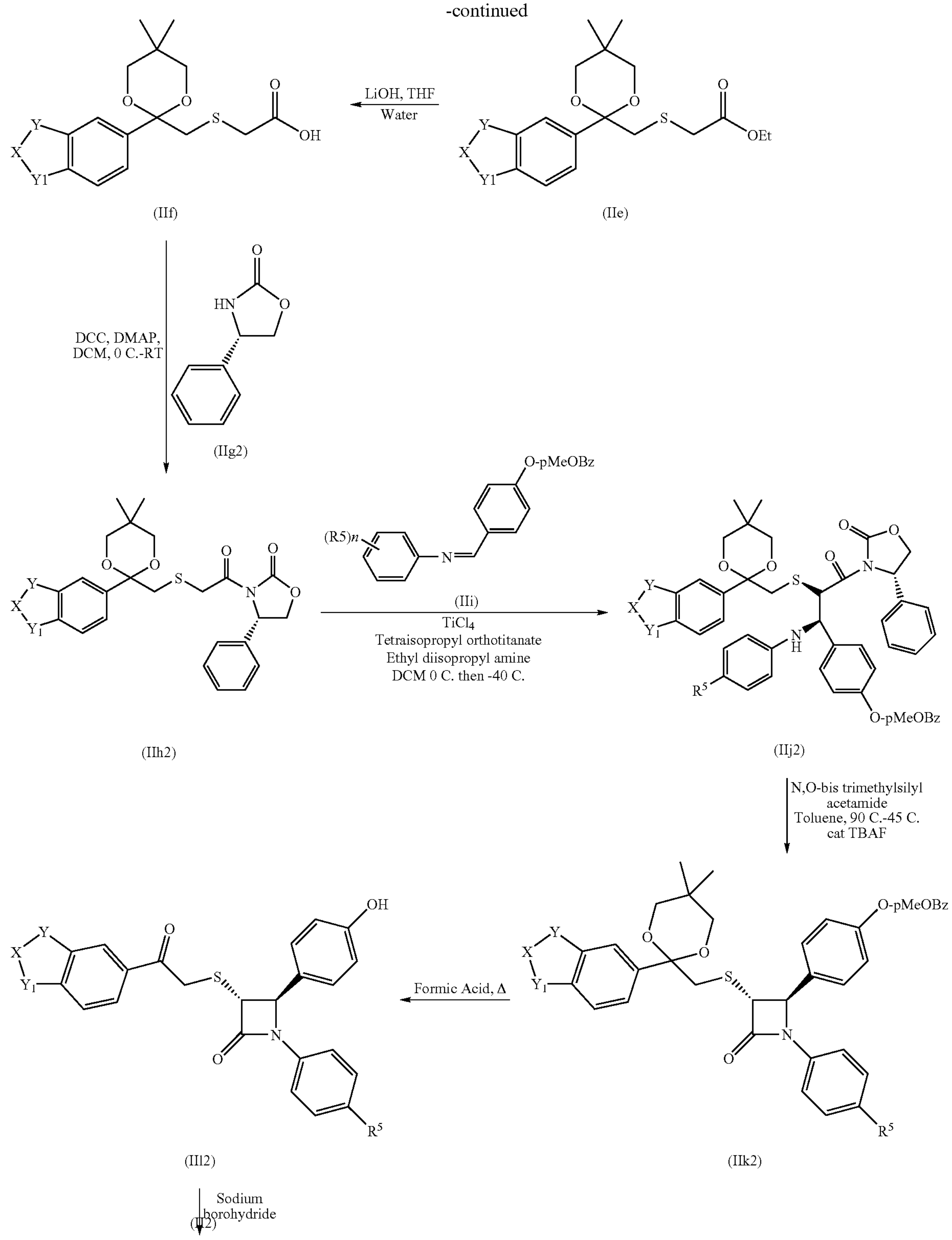
(IIf) (IIe) (IIg2) (IIh2) (IIj2) (IIk2) (III2) (I2)
wherein pMeOBz is para methoxy benzyl.
Compounds of formula (IIb), (IId), (IIg) and (III) are commercially available compounds, or they are known in the literature, or they are prepared by standard processes known in the art.
Another aspect of the present invention provides a process for preparing a compound of formula (I2)

(I2)

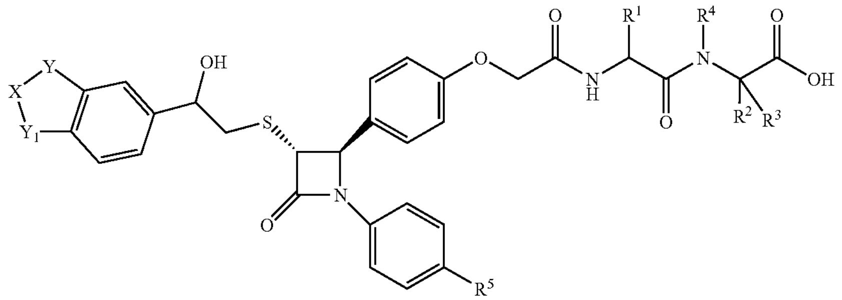

or a pharmaceutically acceptable salt, solvate, solvate of such a salt or a prodrug thereof which process (wherein variable groups are, unless otherwise specified, as defined in formula (I)) comprises of:

Process 1) Reacting a Compound of Formula (II2):

(II2)

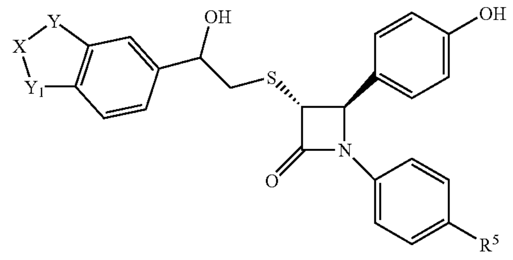

with a compound of formula (III):

(III)

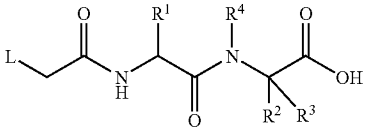

wherein L is a displaceable group;

Process 2) Reacting an Acid of Formula (IV2):

(IV2)

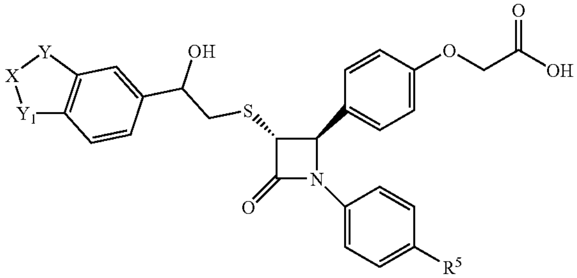

or an activated derivative thereof; with an amine of formula (V):

(V)

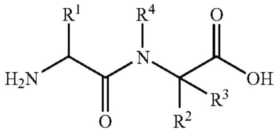

Process 3): Reacting an Acid of Formula (VI2):

(VI2)

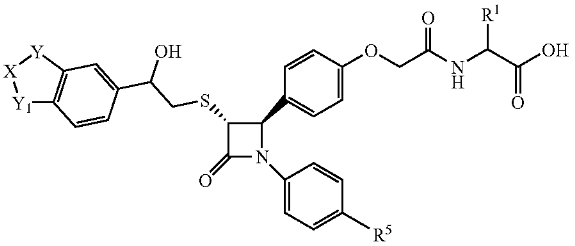

or an activated derivative thereof, with an amine of formula (VII):

(VII)

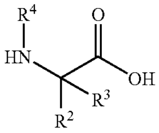

Process 4): Reducing a Compound of Formula (VIII2):
(VIII2)
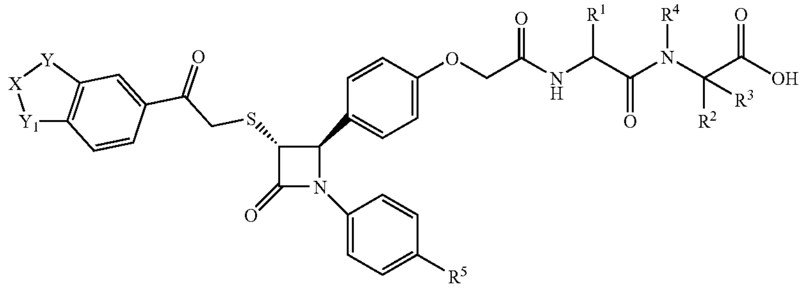
Process 5): Reacting a Compound of Formula (IX2):
(IX2)
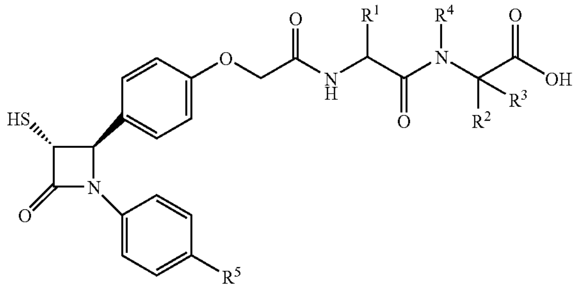
with a compound of formula (X):
(X)
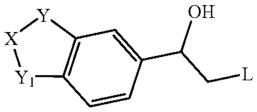
wherein L is a displaceable group;
Process 6): Reacting a Compound of Formula (XI2):
(XI2)
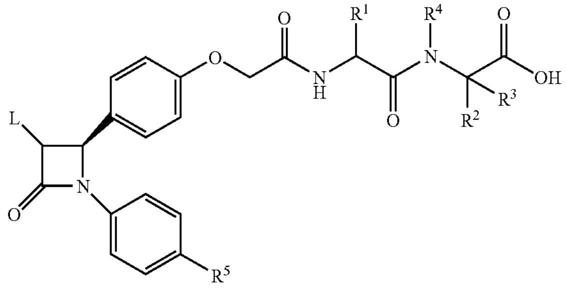
wherein L is a displaceable group; with a compound of formula (XII):
(XII)
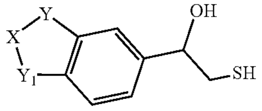
Process 7): De-Esterifying a Compound of Formula (XIII2)
(XIII2)
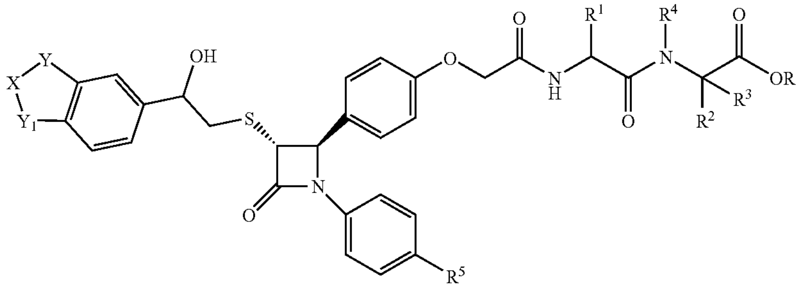

wherein the group C(O)OR is an ester group;

and thereafter if necessary or desirable:

i) converting a compound of the formula (I2) into another compound of the formula (I2);

ii) removing any protecting groups;

iii) forming a pharmaceutically acceptable salt, solvate, solvate of such a salt or a prodrug; or iv) separating two or more enantiomers.

L is a displaceable group, suitable values for L are for example, a halogeno or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B1. Alternatively they can be prepared by the following reactions.

Process 1): Alcohols of formula (II2) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (II2) may be prepared according to the following scheme:

Scheme 1

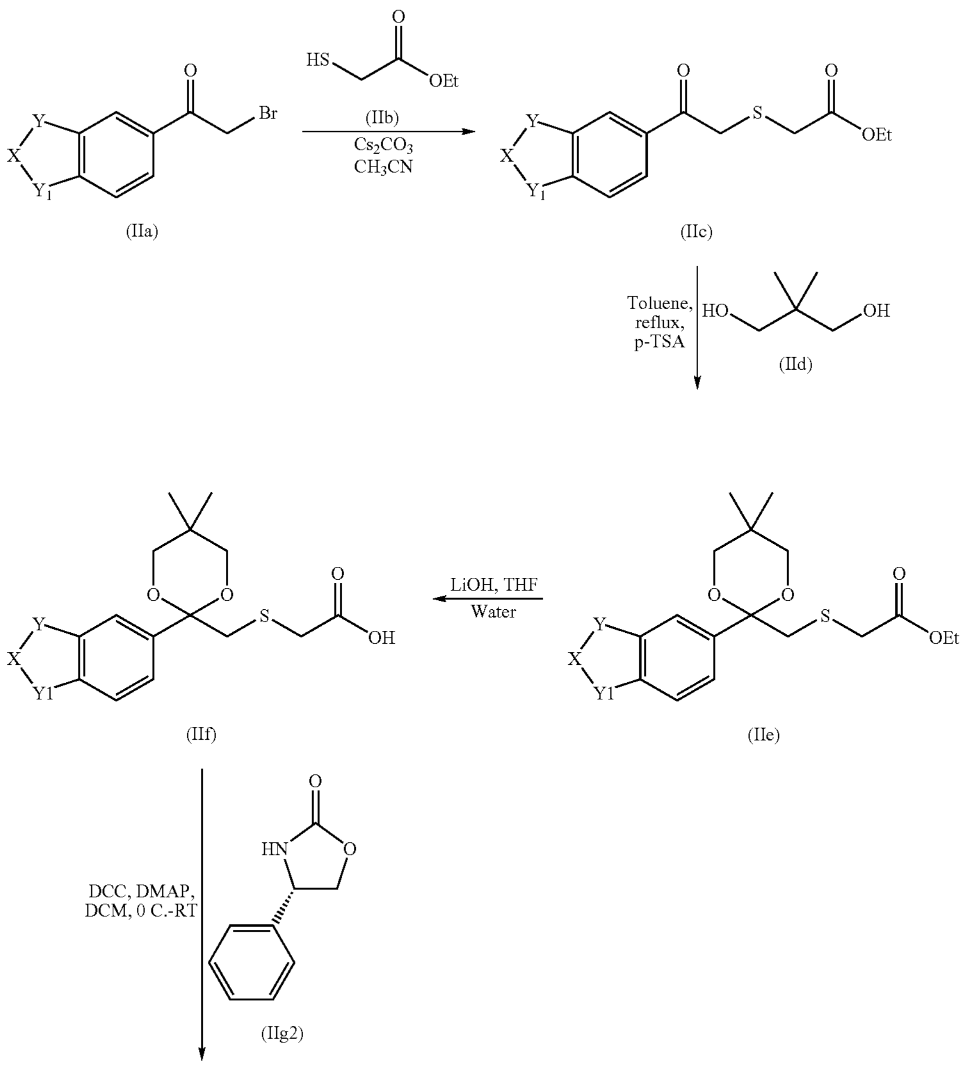

-continued
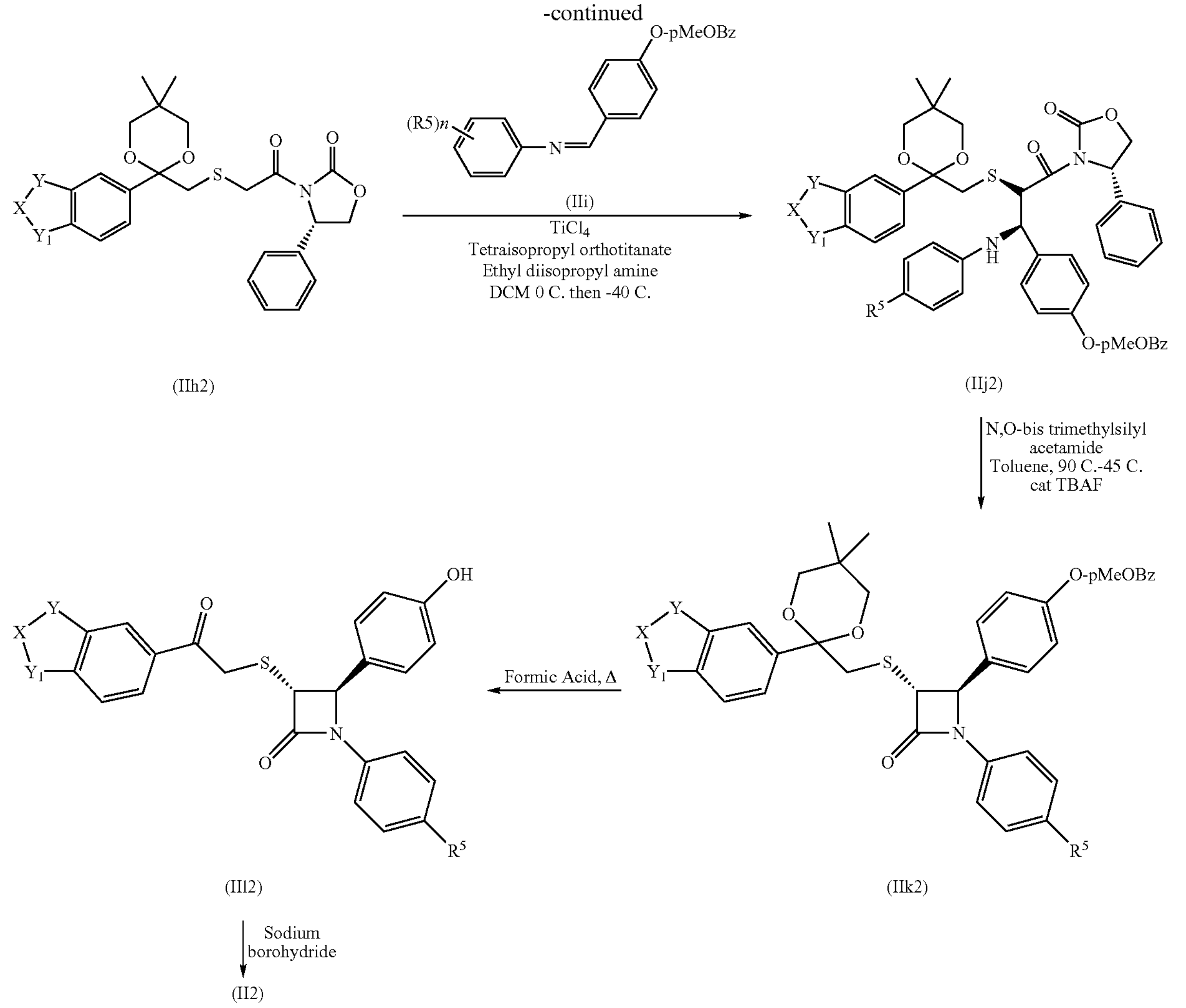
(IIh2) (IIj2) (IIk2) (III2) (II2)
wherein pMeOBz is para methoxy benzyl.
Compounds of formula (IIb), (IId), (Iig2) and (III2) are commercially available compounds, or they are known in the literature, or they are prepared by standard processes known in the art.
A compound of formula (V) may also be reacted with a compound of formula (XIV).
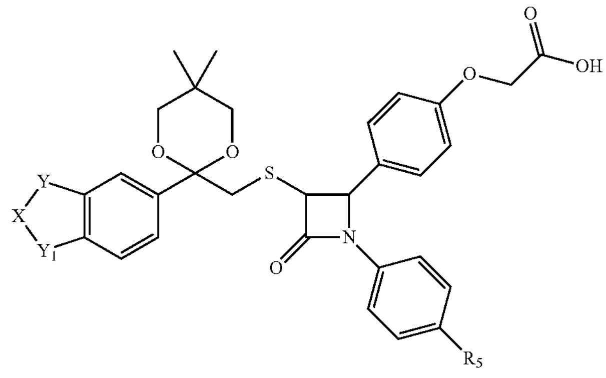
(XIV)

-continued
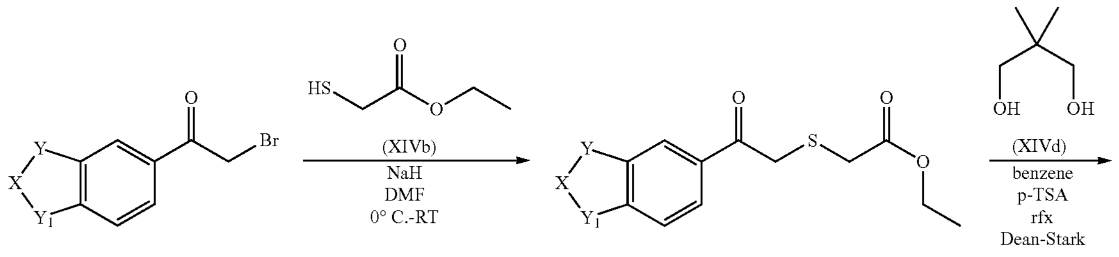
(XIVa) (XIVc)
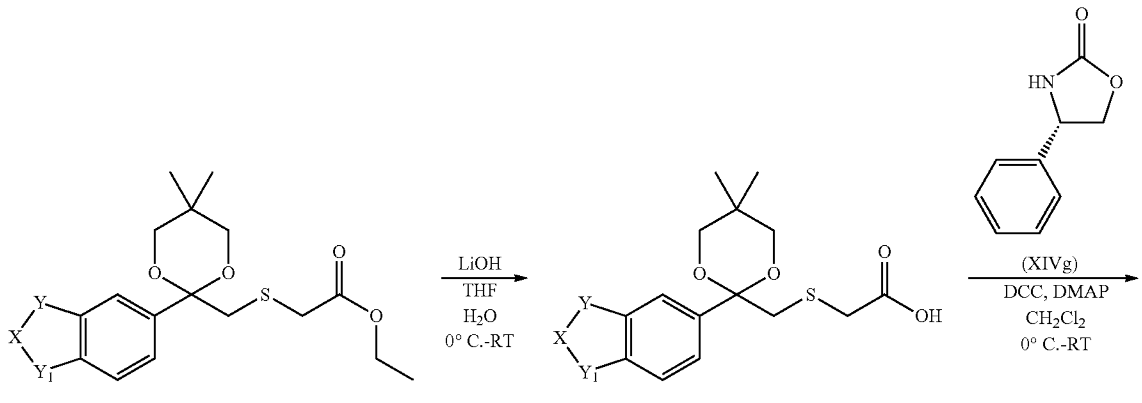
(XIVe) (XIVf)
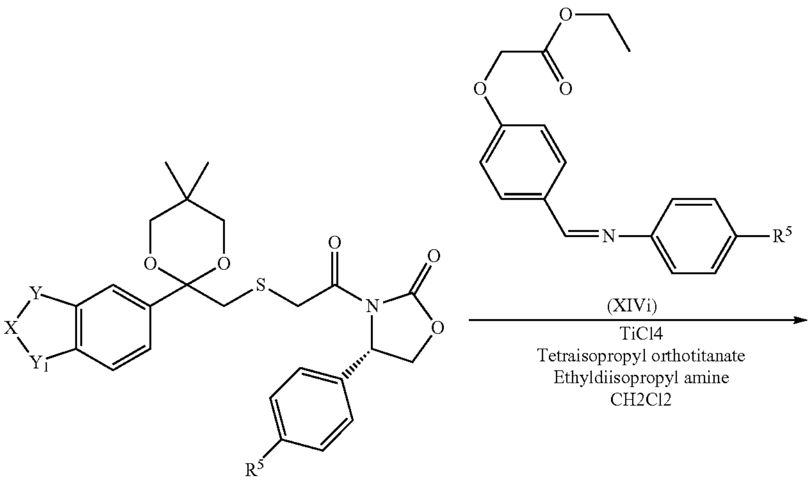
(XIVh)

-continued
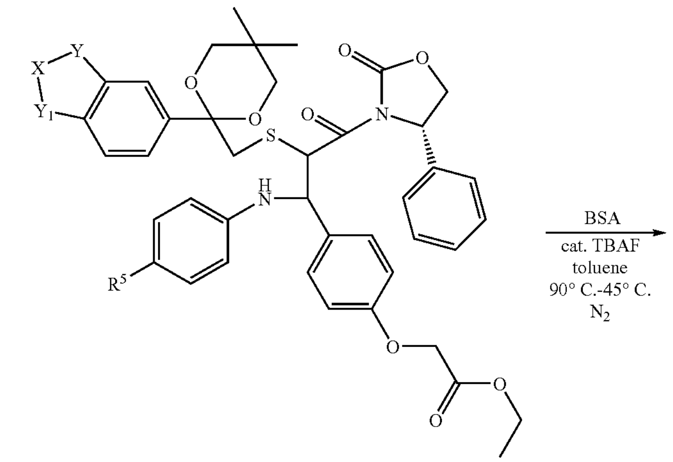
(XIVj)
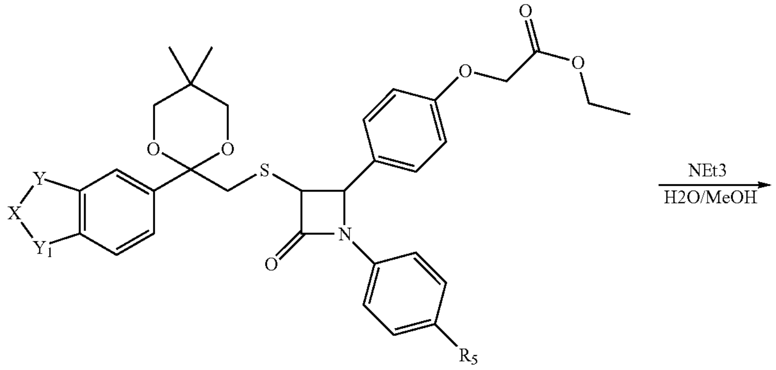
(XIVk)
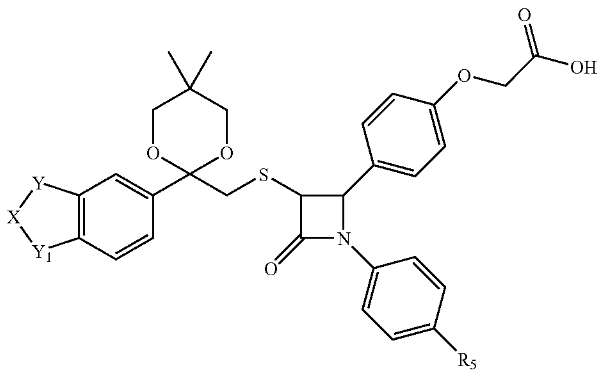
(XIV)

Compounds of formula XIVi may be prepared by the following route:
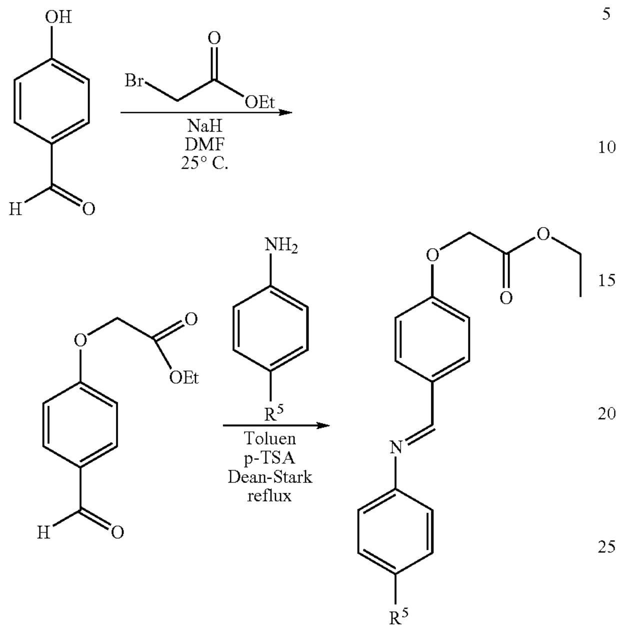
(XIVi)
A compound of formula (III2) may also be reacted with a compound of formula (XIV2).
Compounds of formula (XIV2) may be prepared according to the following route:
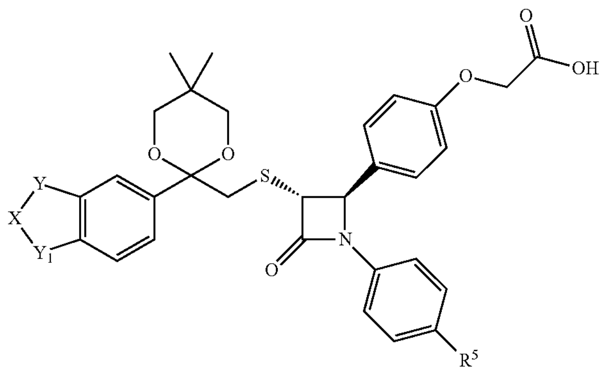
(XIV2)
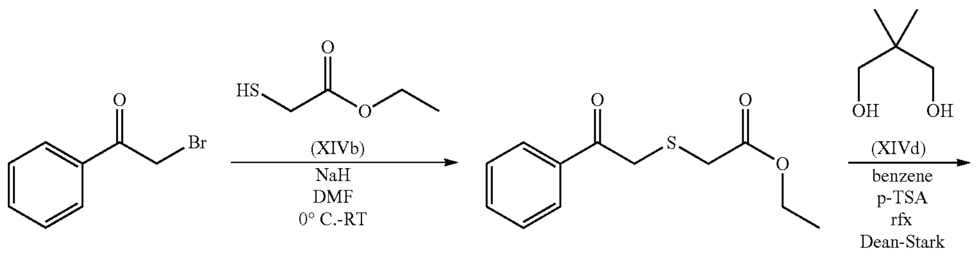
(XIVa)
(XIVc)

-continued
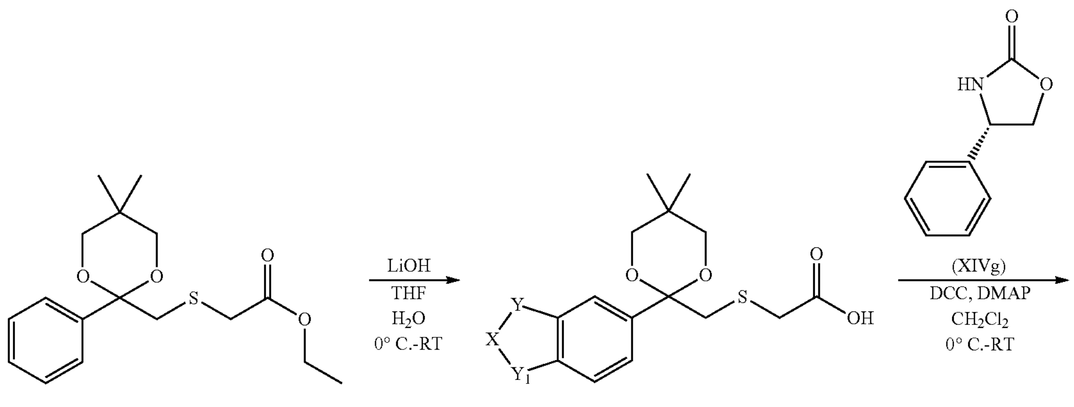
(XIVe) (XIVf)
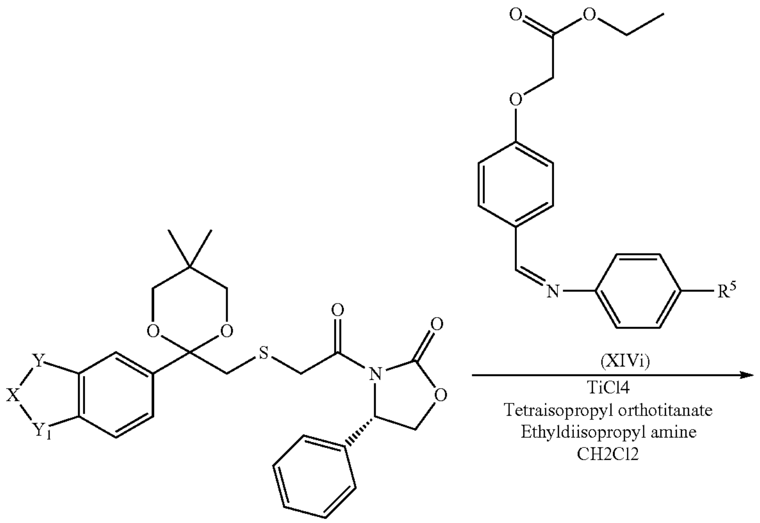
(XIVh)
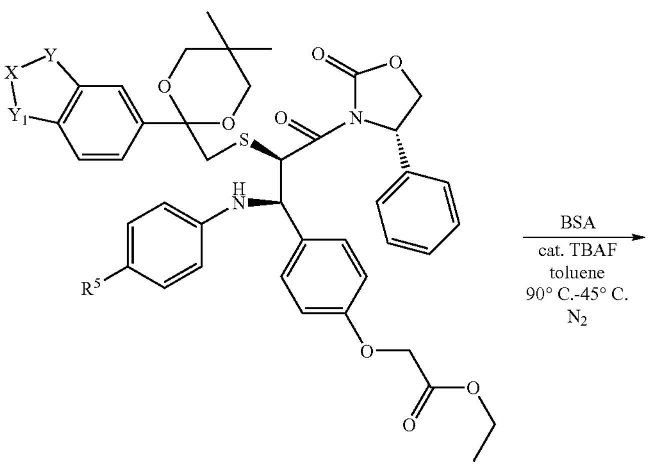
(XIVj2)

-continued

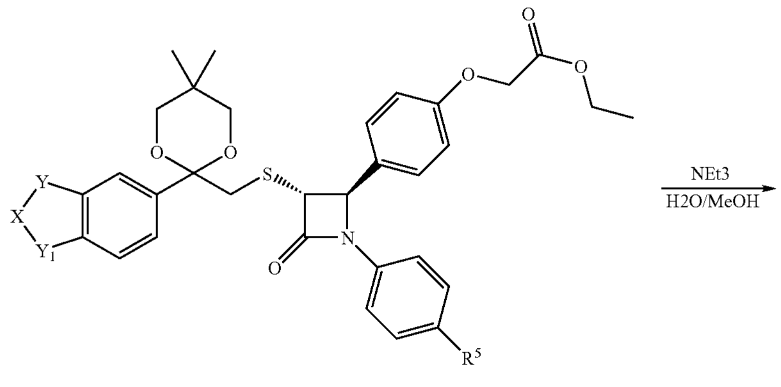

(XIVh2)

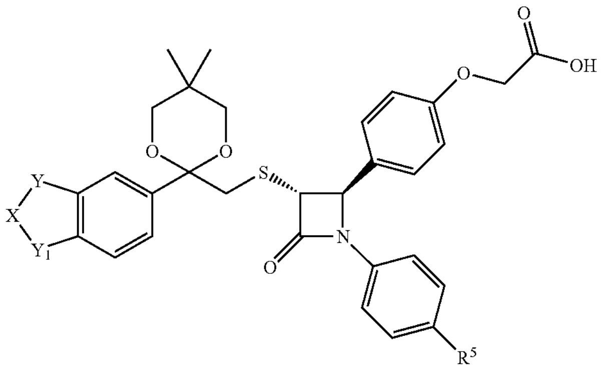

(XIV2)

A compound of formula (XV) may be reduced to a compound of formula (IV) or a compound of formula (XV) may be reacted with a compound of formula (V):

(XV)

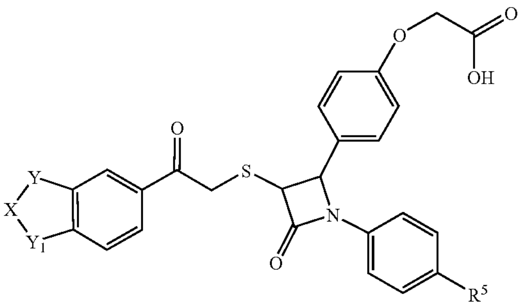

A compound of formula (XV2) may be reduced to a compound of formula (IV2) or a compound of formula (XV2) may be reacted with a compound of formula (V)

(XV2)

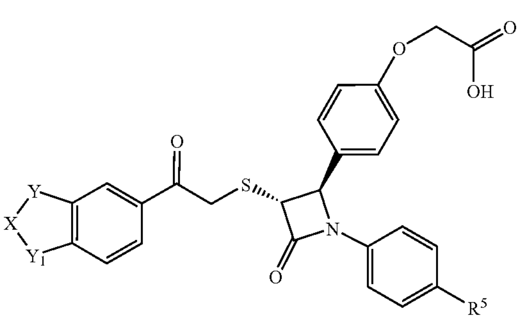

Compounds of formula (XV2) may be prepared according to the following route:

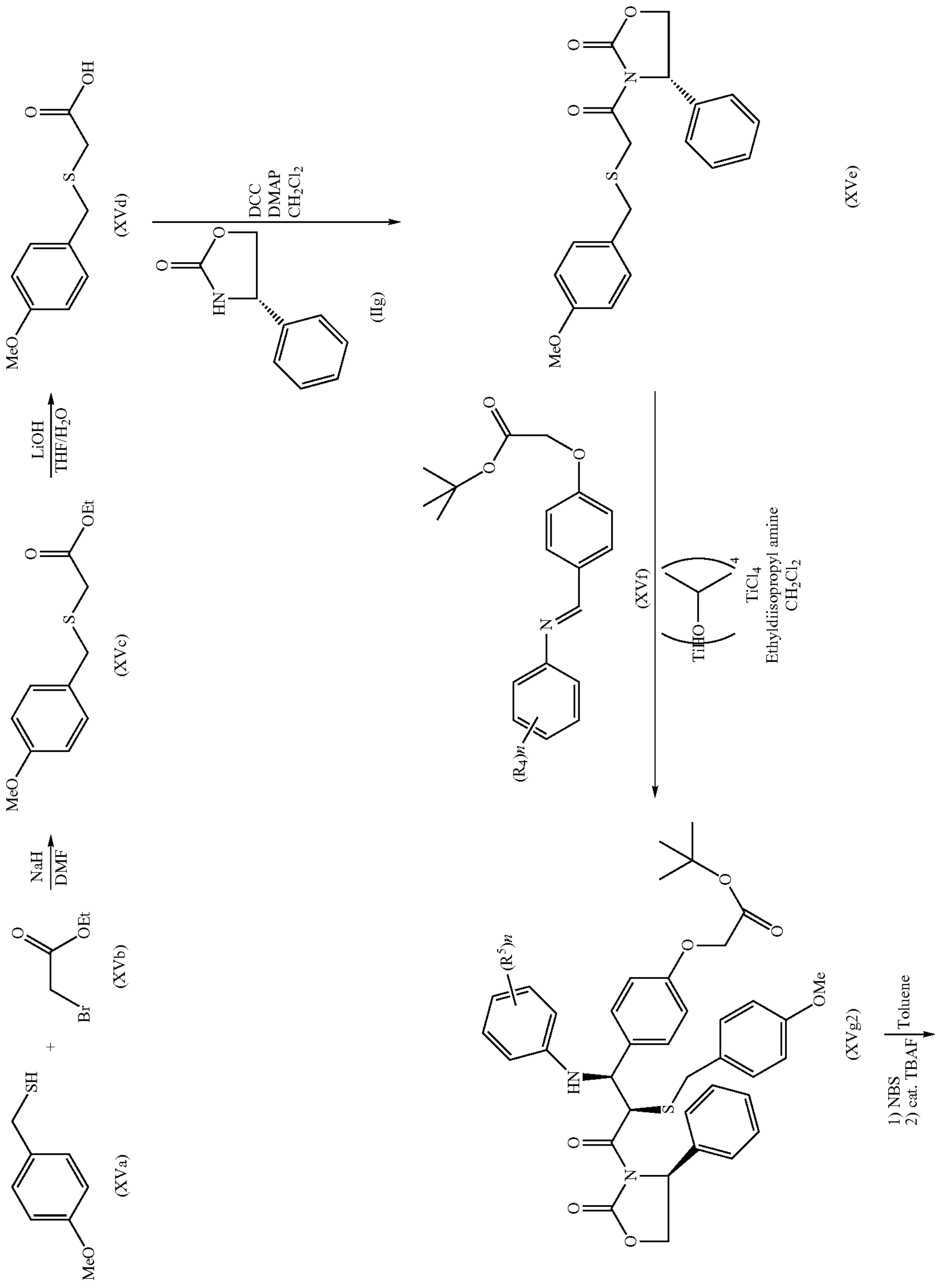
(XVa) (XVb) (XVc) (XVd) (IIg) (XVe) (XVf) (XVg2)

-continued
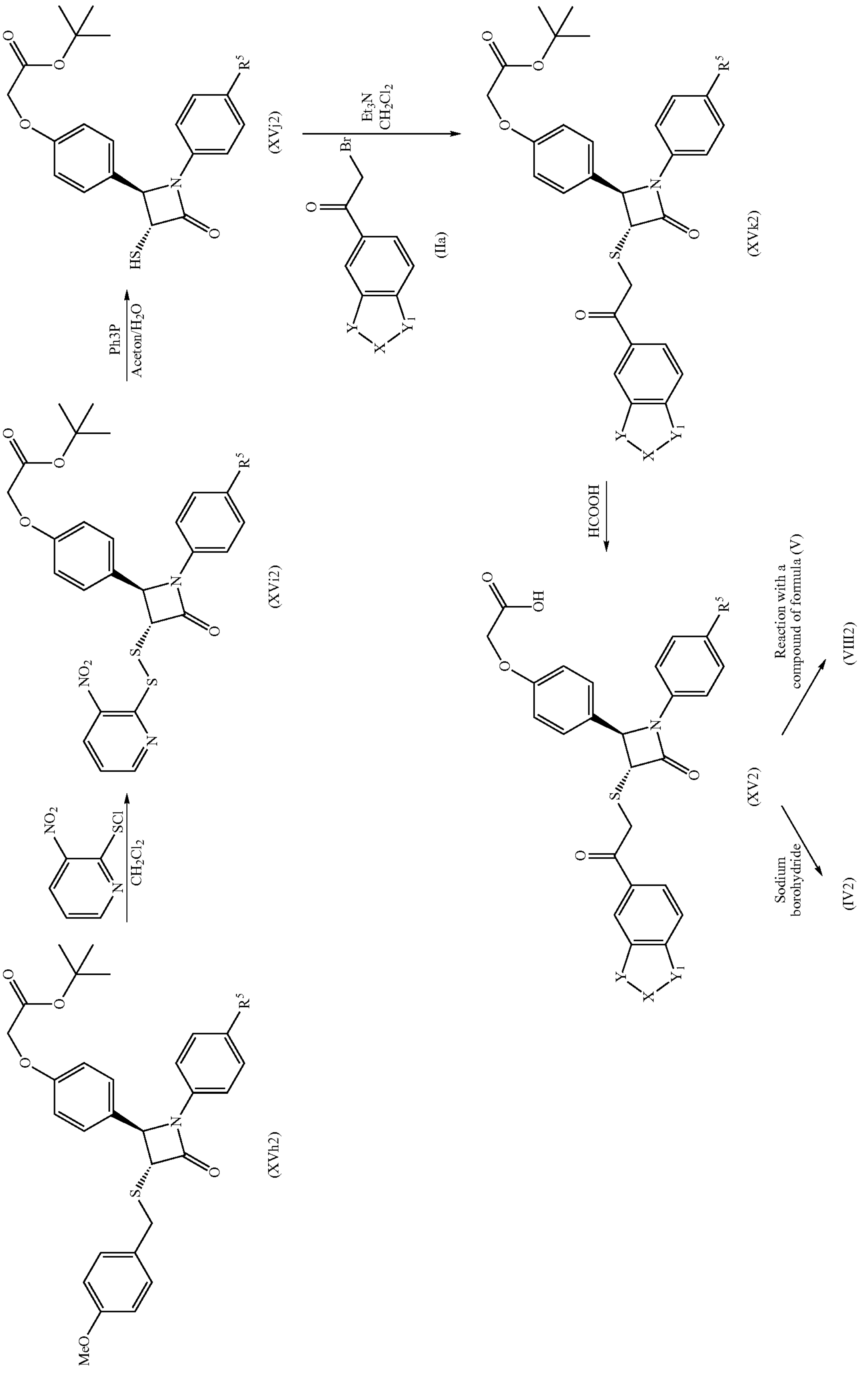

The steps in this scheme are not restricted to the reagents, conditions or protecting groups mentioned.
Compounds of formula (XV2) may be prepared according to the following scheme:
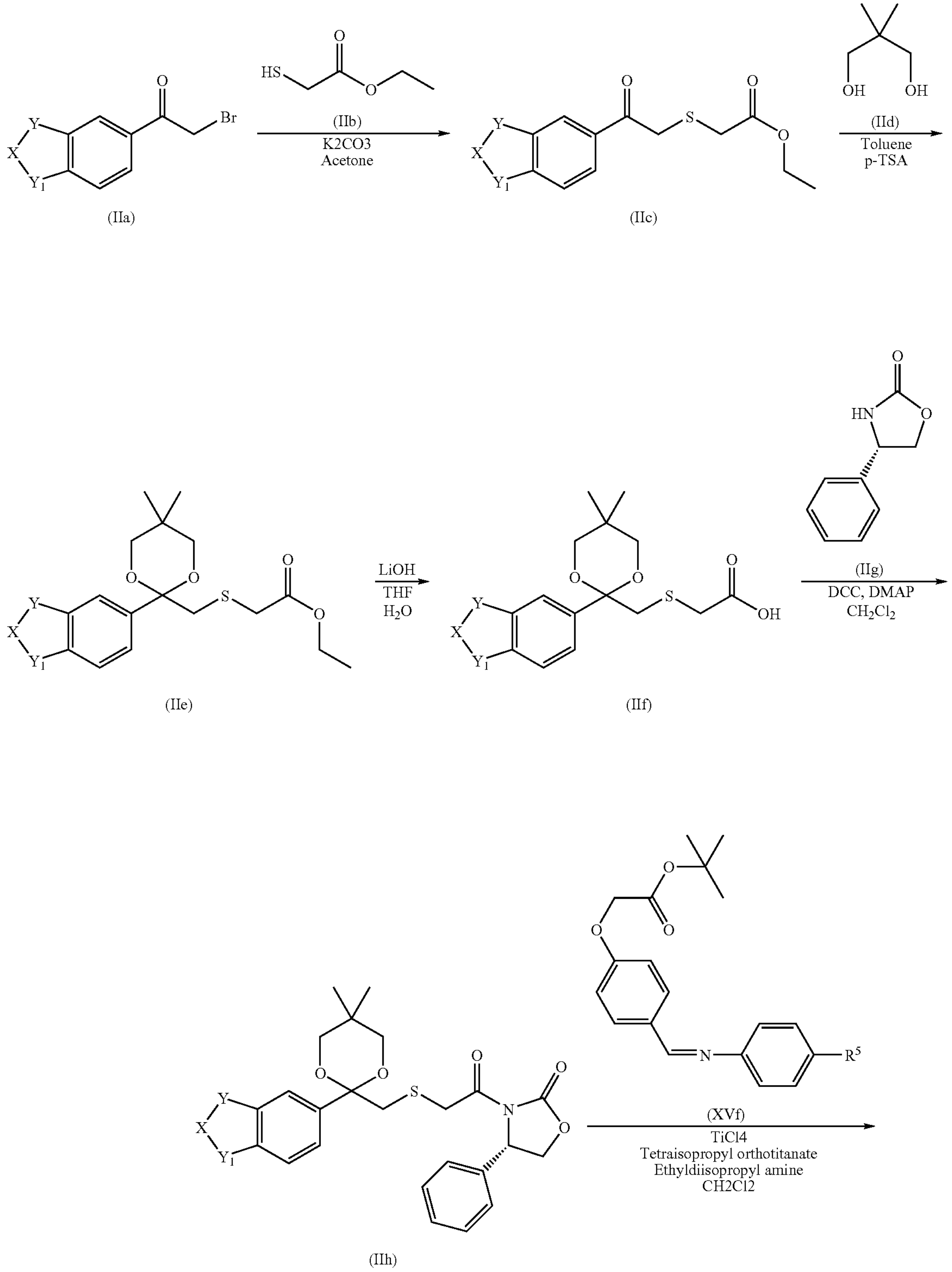

-continued

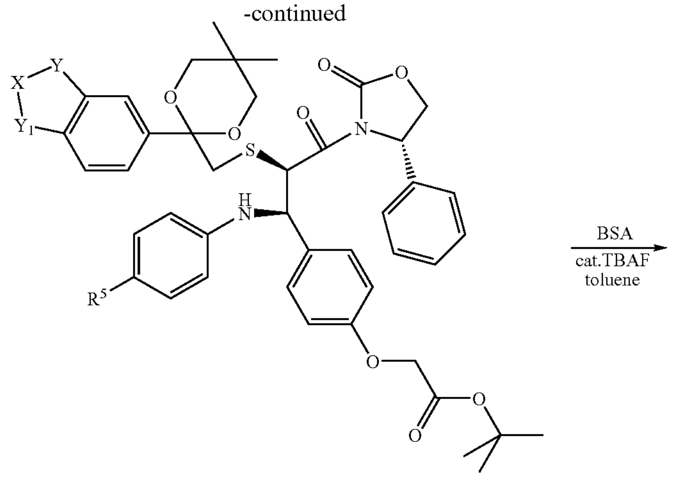

(XVm2)

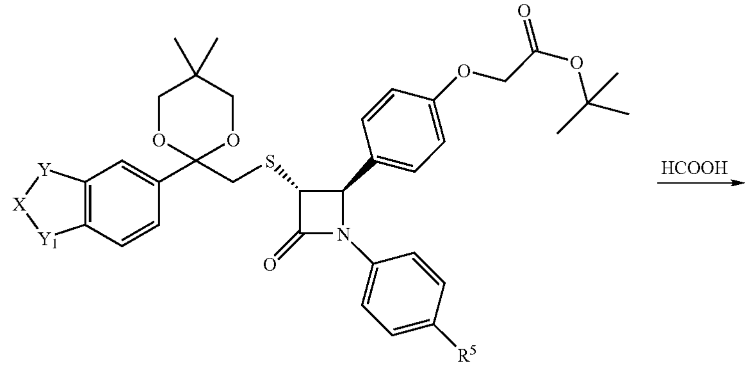

(XVn2)

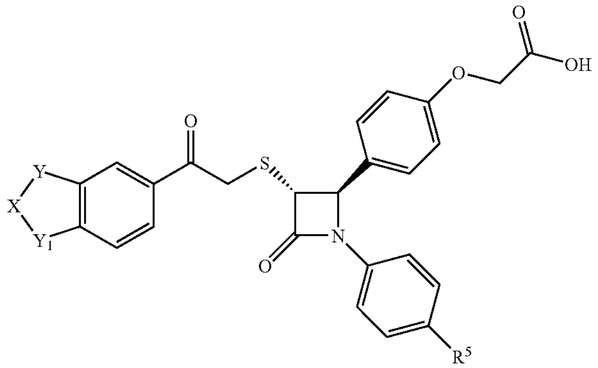

(XV2)

The steps in this scheme are not restricted to the reagents, conditions or protecting groups mentioned.

For XIV and (XV), and in an analogous manner for XIV2 and (XV2) both the following applies:

Process 2) and Process 3): Acids and amines may be coupled together in the presence of a suitable coupling reagent. Standard peptide coupling reagents known in the art can be employed as suitable coupling reagents, for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may, conveniently be performed at a temperature in the range of −40 to 40° C.

Acids of formula (IV) and (VI) may be prepared from compounds of formula (II) by reacting them with the appropriate, optionally protected, side chain using the conditions of Process 1). Alternatively, acids of formula (IV) and (VI) may be prepared by a modification of Scheme I.

Amines of formula (V) and (VII) are commercially available compounds, or they are known in the literature, or they are prepared by standard processes known in the art.

Process 4): Reduction of compounds of formula (VIII) could be performed with a hydride reagent such as sodium borohydride in a solvent such as methanol at temperatures suitable between −20-40° C.

Compounds of formula (VIII) can be prepared from compounds of formula (III), by deprotecting the benzyl group and performing Process 1. Alternatively compound (IIk) could be debenzylated, Process 1 could be performed and the resulting compound deprotected to reveal the ketone.

Process 5) and Process 6): these compounds may be reacted together in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (IX) and (XI) may be prepared by an appropriate modification of Scheme 1.

Compounds of formula (X) and (XII) are commercially available compounds, or they are known in the literature, or they, are prepared by standard processes known in the art.

Process 7): Esters of formula (XIII) may be deprotected under standard conditions such as those described below, for example a methyl or ethyl ester may be deprotected with sodium hydroxide in methanol at room temperature.

Compounds of formula (XIII) may be prepared by a modification of any of the processes described herein for the preparation of compounds of formula (I).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkyltliio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

The invention further provides for a compound of the formula (XVI) or hydrolysable esters or amides thereof:

(XVI)

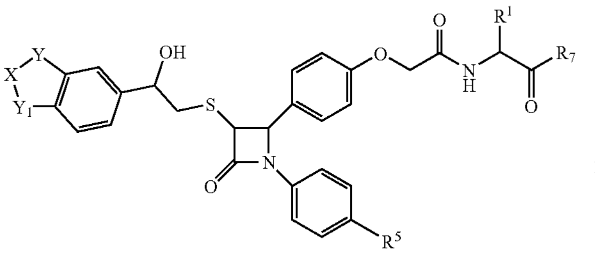

wherein $R^7$ is an hydroxy group or a $C_{1-4}$ alkoxy group. $R^1$, is as defined above regarding formula (I). A compound of formula (XVI) may be an intermediate to formula (I).

The invention further provides for a compound of the formula (XVI2) or hydrolysable esters or amides thereof:

(XVI2)

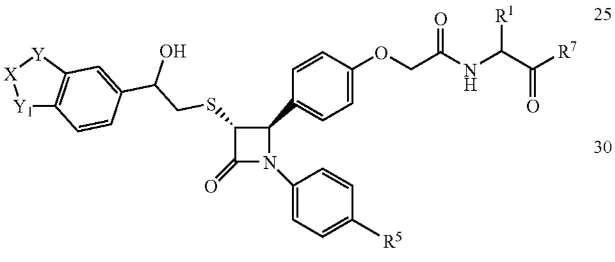

wherein $R^7$ is an hydroxy group or a $C_{1-3}$ alkoxy group. $R^1$ is as defined above regarding formula (I). A compound of formula (XVI2) may be an intermediate to formula (I2).

As stated hereinbefore the compounds defined in the present invention possess cholesterol absorption inhibitory activity. These properties may be assessed, using the following biological tests.

In Vivo Testing of Cholesterol Absorption Inhibitors (A)

C57BL/6 female mice were maintained on regular chow diet and housed in individual cages to collect faeces. Mice were fasted for 3 hours and then gavaged with vehicle or compound. Half an hour later the mice were gavaged with radiolabelled cholesterol. Six hours after the $^{14}$C-cholesterol gavage blood samples were taken via the tail and plasma prepared to determine how much cholesterol were absorbed. 24 hours after the gavage of $^{14}$C-cholesterol the mice were bled and plasma were prepared for analysis. Faeces were collected for 24 hours to assess absorption efficiency.

In Vivo Testing of Cholesterol Absorption Inhibitors (B).

C57BL/6 female mice were maintained on regular chow diet and housed in individual cages to collect faeces. Mice were fasted for 3 hours and then gavaged with vehicle or compound. One to ten hours later the mice were gavaged with radiolabelled cholesterol. Six hours after the $^{14}$C-cholesterol gavage blood sample was taken via the tail and plasma prepared to determine how much cholesterol was absorbed. 24 hours after the gavage of $^{14}$C-cholesterol the mice were bled and plasma analysed for radioactivity. Faeces were also collected for 24 hours to assess absorption efficiency.

REFERENCES

1. E. A. Kirk, G. L. Moe, M. T. Caldwell, J. Å. Lernmark, D. L. Wilson, R. C. LeBoeuf. Hyper- and hypo-responsiveness to dietary fat and cholesterol among inbred mice: searching for level and variability genes. J. Lipid Res. 1995 36:1522-1532.
2. C. P. Carter, P. N. Howles, D. Y. Hui. Genetic variation in cholesterol absorption efficiency among inbred strains of mice. J. Nutr. 1997 127:1344-1348.
3. C. D. Jolley, J. M. Dietschy, S. D. Turley. Genetic differences in cholesterol absorption in 129/Sv and C57BL/6 mice: effect on cholesterol responsiveness. Am. J. Physiol. 1999 276:G1117-G1124.

Administration of 0.2 μmol/kg of Example 3 gave 59% inhibition of $^{14}$C-cholesterol absorption (procedure A). Administration of 0.2 μmol/kg of Example 4 gave 53% inhibition of $^{14}$C-cholesterol absorption (procedure A).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range of approximately 0.02-100 mg/kg, preferably 0.02-50 mg/kg, and this normally provides a therapeutically-effective dose. Preferably a daily dose in the range of 1-50 mg/kg, particularly 0.1-10 mg/kg is employed. In another aspect a daily dose in the rage of 0.01-20 mg/kg is employed. In one aspect of the invention the daily dose of a compound of formula (I) is less than or equal to 100 mg. However the daily dose will necessarily be varied depending upon the host treated, the particular route of administration, and the severity of the illness being treated. Accordingly the optimum dosage may be determined by the practitioner who is treating any particular patient. A unit dose form such as a tablet or capsule will usually contain, for example 1-250 mg of active ingredient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective cholesterol absorption inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of a cholesterol absorption inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the production of a cholesterol absorption inhibitory effect in a warm-blooded animal, such as man.

Herein, where the production of a cholesterol absorption inhibitory effect or a cholesterol lowering effect is stated, suitably this relates to the treatment of hyperlipidaemic conditions in a warm-blooded animal, such as man. Additionally is relates to the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronernia, hypolipoproteinemia, hypercholesterolemia, hyperlipoproteinemia and hypoalphalipoproteinemia (low HDL) in a warm-blooded animal, such as man. Furthermore it relates to the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man. It also relates to the treatment of atherosclerosis, coronary heart diseases, myocardial infarction, angina pectoris, peripheral vascular diseases, stroke and transient ischaemic attacks in a warm-blooded animal, such as man.

The production of a cholesterol absorption inhibitory effect or a cholesterol lowering effect also relates to a method of treating and/or preventing atherosclerotic lesions, a method of preventing plaque rupture and a method of promoting lesion regression. Furthermore it relates to a method of inhibiting monocytes-macrophage accumulation in atherosclerotic lesions, a method of inhibiting expression of matrix metalloproteinases in atherosclerotic lesions, a method of inhibiting the destabilization of atherosclerotic lesions, a method for preventing atherosclerotic plaque rupture and a method of treating unstable angina.

The production of a cholesterol absorption inhibitory effect or a cholesterol lowering effect also relates to a method of treating sitosterolemia.

Compounds of formula (I), or a pharmaceutically acceptable salt, solvate, solvate of such a salt or a prodrug thereof may also have value in the treatment or prevention of Alzheimer's Disease (see for example WO 02/096415). Therefore in a further aspect of the invention, there is provided a compound of formula (I), or a pharmaceutically acceptable salt, solvate, solvate of such a salt or a prodrug thereof, for use in the treatment or prevention of Alzheimer's Disease.

Compounds of formula (I), or a pharmaceutically acceptable salt, solvate, solvate of such a salt or a prodrug thereof may also have value in the treatment or prevention cholesterol associated tumors. Therefore in a further aspect of the invention, there is provided a compound of formula (I), or a pharmaceutically acceptable salt, solvate, solvate of such a salt or a prodrug thereof, for use in the treatment or prevention of cholesterol associated tumors.

Compounds of formula (I), or a pharmaceutically acceptable salt, solvate, solvate of such a salt or a prodrug thereof may also have value in the treatment or prevention of vascular inflammation (see for example WO 03/026644). Therefore in a further aspect of the invention, there is provided a compound of formula (I), or a pharmaceutically acceptable salt, solvate, solvate of such a salt or a prodrug thereof, for use in the treatment or prevention of vascular inflammation.

According to a further feature of this aspect of the invention there is provided a method for producing a cholesterol absorption inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

The cholesterol absorption inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional cholesterol absorption inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with cholesterol biosynthesis inhibitors, or pharmaceutically acceptable salts, solvates, solvates of such salts or prodrugs thereof. Suitable cholesterol biosynthesis inhibitors include HMG Co-A reductase inhibitors, squalene synthesis inhibitors and squalene epoxidase inhibitors. Suitable squalene synthesis inhibitors are e.g. squalestatin 1, TAK 475 and compounds described in WO2005012284. A suitable squalene epoxidase inhibitor is NB-598.

In this aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and rosuvastatin, or a pharmaceutically acceptable salt, solvate, solvate of such a salt or a prodrug thereof. A further particular statin is pitavastatin, or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is rosuvastatin, or a pharmaceutically acceptable salt, solvate, solvate of such a salt or a prodrug thereof. A preferable particular statin is rosuvastatin calcium salt.

Therefore in an additional feature of the invention, there is provided a combination of a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) an HMG Co-A reductase inhibitor, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) an HMG Co-A reductase inhibitor, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of a cholesterol lowering effect.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a matrix metalloproteinase inhibitor.

In another aspect of the invention, the compound of formula (I), or a pharmaceutically acceptable salt, solvate, solvate of such a salt or a prodrug thereof, may be administered in association with an ileal bile acid (IBAT) inhibitor or a pharmaceutically acceptable salt, solvate, solvate of such a salt or a prodrug thereof. Suitable compounds possessing IBAT inhibitory activity for use in combination with compounds of the present invention have been described, see for instance the compounds described in WO 93/16055, WO 94/18183, WO 94/18184, WO 94/24087, WO 96/05188, WO 96/08484, WO 96/16051, WO 97/33882, WO 98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 00/35889, WO 01/34570, WO 00/38725, WO 00/38726, WO 00/38727, WO 00/38728, WO 00/38729, WO 00/47568, WO 00/61568, WO 01/66533, WO 01/68096, WO 01/68637, WO 02/08211, WO 02/50051, WO 03/018024, WO 03/040127, WO 03/043992, WO 03/061604, WO 04/020421, WO 04/076430, DE 19825804, JP 10072371, U.S. Pat. No. 5,070, 103, EP 251 315, EP 417 725, EP 489 423, EP 549 967, EP 573 848, EP 624 593, EP 624 594, EP 624 595, EP 864 582, EP 869 121 and EP 1 070 703, WO 03/020710, WO 03/022825, WO 03/022830, WO 03/022286, WO 03/091232, WO 03/106482, and EP 597 107 and the contents of these patent applications are incorporated herein by reference. Particularly the named examples of these patent applications are incorporated herein by reference. More particularly claim 1 of these patent application are incorporated herein by reference.

Other suitable classes of IBAT inhibitors for use in combination with compounds of the present invention are the benzothiepines, 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity for use in combination with compounds of the present invention is (3R,5R)-3-butyl-3-ethyl-1,1-dioxido-5-phenyl-2,3,4,5-tetrahydro-1,4-benzothiazepin-8-yl beta-D-glucopyranosiduronic acid (EP 864 582).

A further suitable compound possessing IBAT inhibitory activity for use in combination with compounds of the present invention is S-8921 (EP 597 107) and BARI-1741.

A further suitable BAT inhibitor for use in combination with compounds of the present invention is the compound:

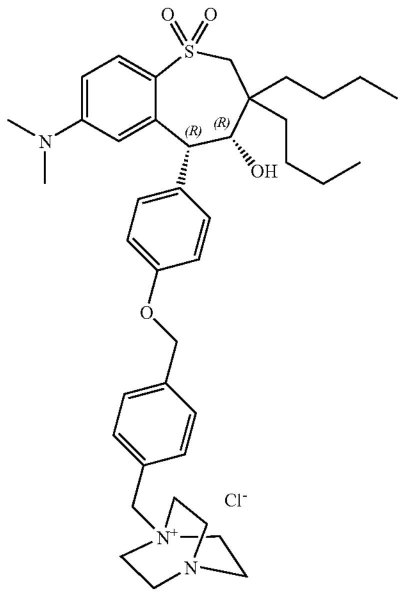

WO 99/32478

A particular IBAT inhibitor for use in combination with compounds of the present invention is selected from any one of Examples 1-120 of WO 02/50051, or a pharmaceutically acceptable salt, solvate, solvate of such a salt or a prodrug thereof, and the compounds of Examples 1-120 are incorporated herein by reference. Claims 1-15 of WO 02/50051 are also incorporated herein by reference. A particular BAT inhibitor selected from WO 02/50051 for use in combination with compounds of the present invention is selected from any one of:

1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N—{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'-(5-carboxypentyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'—(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N—[(R)-α-(N'-{(R)-1-[N"-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphorylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N—[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N—{(R)-α-[N'-(2-methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N—[(R)-α-(N'-{2-[(methyl)(ethyl) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N—[(R)-α-(N'-{2-[(methyl)(hydroxy) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N—{(R)-α-[(R)—N'-(2-methylsulphinyl-1-carboxyethyl)carbamoyl]benzyl}carbamoylmethoxy)-2,3,4,5-tetrahydro-1,5-benzothiazepine; and 1,1-dioxo-3,3-dibutyl-5-phenyl-7-methoxy-8-[N—{(R)-α-[N'-(2-sulphoethyl)carbamoyl]-4-hydroxybenzyl}carbamoylmethoxy]-2,3,4,5-tetrahydro-1,5-benzothiazepine;

or a pharmaceutically acceptable salt, solvate, solvate of such a salt or a prodrug thereof.

A particular IBAT inhibitor for use in combination with compounds of the present invention is selected from any one of Examples 1-44 of WO 03/020710, or a pharmaceutically acceptable salt, solvate, solvate of such a salt or a prodrug thereof, and the compounds of Examples 1-44 are incorporated herein by reference. Claims 1-10 of WO 03/020710 are also incorporated herein by reference. A particular IBAT inhibitor selected from WO 03/020710 for use in combination with compounds of the present invention is selected from any one of:

1,1-dioxo-3,3-dibutyl-5-phenyl-7-methylthio-8-(N—{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'—((S)-1-carbamoyl-2-hydroxyethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'-(hydroxycarbamoylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N—((R)-α-{N'[2-(N'-pyrimidin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-[N—((R)-α-{N'[2-(N'-pyridin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-(N—{(R)-α-[N'-(1-t-butoxycarbonylpiperidin-4-ylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'-(2,3-dihydroxypropyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N—((R)-α-{N'-[2-(3,4-dihydroxyphenyl)-2-methoxyethyl]carbamoyl}benzyl)carbamoylmethoxy]-2,3,4,5-tetrahydro-1,5-benzothiazepine 1,1-dioxo-3-butyl-3-ethyl-5-phenyl-7-methylthio-8-(N—{(R)-α-[N'-(2-aminoethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'-(piperidin-4-ylmethyl) carbamoyl]benzyl}carbamoylmethoxy)-2,3,4,5-tetrahydro-1,5-benzothiazepine; or 1,1-dioxo-3-butyl-3-ethyl-5-phenyl-7-methylthio-8-(N—{(R)-α-[N'-(2-N,N-dimethylaminosulphamoylethyl)carbamoyl]benzyl}carbamoylmethoxy)-2,3,4,5-tetrahydro-1,5-benzothiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/022825, or a pharmaceutically acceptable salt, solvate, solvate of such a salt or a prodrug thereof, and the compounds of Examples 1-7 are incorporated herein by reference. Claims 1-8 of WO 03/022825 are also incorporated herein by reference. A particular IBAT inhibitor selected from WO 03/022825 for use in combination with compounds of the present invention is selected from any one of:

1,1-dioxo-3(R)-3-butyl-3-ethyl-5-(R)-5-phenyl-8-[N—((R)-α-carboxybenzyl) carbamoylmethoxy]-2,3,4,5-tetrahydro-1,4-benzothiazepine;

1,1-dioxo-3(S)-3-butyl-3-ethyl-5-(S)-5-phenyl-8-[N—((R)-α-carboxybenzyl) carbamoylmethoxy]-2,3,4,5-tetrahydro-1,4-benzothiazepine;

1,1-dioxo-3(R)-3-butyl-3-ethyl-5-(R)-5-phenyl-8-(N—{(R)-α-[N-(carboxymethyl)carbamoyl]benzyl}carbamoylmethoxy)-2,3,4,5-tetrahydro-1,4-benzothiazepine;

1,1-dioxo-3(S)-3-butyl-3-ethyl-5-(S)-5-phenyl-8-(N—{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-bromo-8-(N—{(R)-α-[N-(carboxymethyl)carbamoyl]benzyl}carbamoylmethoxy)-2,3,4,5-tetrahydro-1,4-benzothiazepine;

3,5-trans-1,1-dioxo-3-(S)-3-ethyl-3-butyl-4-hydroxy-5-(S)-5-phenyl-7-bromo-8-(N—{(R)-α-[N-(carboxymethyl)carbamoyl]benzyl}carbamoylmethoxy)-2,3,4,5-tetrahydro-1,4-benzothiazepine 3,5-trans-1,1-dioxo-3-(R)-3-ethyl-3-butyl-4-hydroxy-5-(R)-5-phenyl-7-bromo-8-(N—{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N—{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,4-benzothiazepine ammonia salt;

1,1-dioxo-3-(S)-3-ethyl-3-butyl-5-(S)-5-phenyl-7-methylthio-8-(N—{(R)-α-[N-(carboxymethyl)carbamoyl]benzyl}carbamoylmethoxy)-2,3,4,5-tetrahydro-1,4-benzothiazepine diethylamine salt; and 1,1-dioxo-3-(R)-3-ethyl-3-butyl-5-(R)-5-phenyl-7-methylthio-8-(N—{(R)-α-[N-(carboxymethyl)carbamoyl]benzyl}carbamoylmethoxy)-2,3,4,5-tetrahydro-1,4-benzothiazepine diethylamine salt;

or a pharmaceutically acceptable salt, solvate, solvate of such a salt or a prodrug thereof.

A particular IBAT inhibitor for use in combination with compounds of the present invention is selected from any one of Examples 1-4 of WO 03/022830, or a pharmaceutically acceptable salt, solvate, solvate of such a salt or a prodrug thereof, and the compounds of Examples 1-4 are incorporated herein by reference. Claims 1-8 of WO 03/022830 are also incorporated herein by reference. A particular IBAT inhibitor selected from WO 03/022830 for use in combination with compounds of the present invention is selected from any one of:

1,1-dioxo-3-butyl-3-ethyl-4-hydroxy-5-phenyl-7-(N—{(R)-α-[N-(carboxymethyl)carbamoyl]benzyl}carbamoylmethylthio)-2,3,4,5-tetrahydrobenzothiepine 1,1-dioxo-3-butyl-3-ethyl-4-hydroxy-5-phenyl-7-(N—{(R)-α-[N-(2-sulphoethyl)carbamoyl]-4-hydroxybenzyl}carbamoylmethylthio)-2,3,4,5-tetrahydrobenzothiepine ammonia salt 1,1-dioxo-3-butyl-3-ethyl-4-hydroxy-5-phenyl-7-{N-[α-(carboxy)-2-fluorobenzyl]carbamoylmethylthio}-2,3,4,5-tetrahydrobenzothiepine; and 1,1-dioxo-3-butyl-3-ethyl-4-hydroxy-5-phenyl-7-{N-[1-(carboxy)-1-(thien-2-yl)methyl]carbamoylmethylthio}-2,3,4,5-tetrahydrobenzothiepine or a pharmaceutically acceptable salt, solvate, solvate of such a salt or a prodrug thereof.

A particular IBAT inhibitor for use in combination with compounds of the present invention is selected from any one of Examples 1-39 of WO 03/022286, or a pharmaceutically acceptable salt, solvate, solvate of such a salt or a prodrug thereof, and the compounds of Examples 1-39 are incorporated herein by reference. Claims 1-10 of WO 03/022286 are also incorporated herein by reference. A particular IBAT inhibitor selected from WO 03/022286 for use in combination with compounds of the present invention is selected from any one of:

1,1-dioxo-3,3-dibutyl-5-phenyl-7-methylthio-8-(N—{(R)-α-[N—((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxybutyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxypropyl) carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxyethyl) carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-(R)-hydroxypropyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((R)-1-carboxy-2-methylthioethyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N-{(S)-1-[N—((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-methylpropyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxypropyl) carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-[N—((R)-α-carboxy-4-hydroxybenzyl)carbamoylmethoxy]-2,3,4,5-tetrahydro-1,2,5-benzothiadiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/091232, or a pharmaceutically acceptable salt, solvate, solvate of such a salt or a prodrug thereof, and the compounds of Examples 1-7 are incorporated herein by reference. Claims 1-10 of WO 03/091232 are also incorporated herein by reference. A particular IBAT inhibitor selected from WO 03/091232 for use in combination with compounds of the present invention is selected from any one of:

1,1-Dioxo-3,3-dibutyl-5-phenyl-7-methylthio-8-(N—{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N—{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N—((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-{N—[(R)-α-(N-{2-(S)-[N-(carbamoylmethyl)carbamoyl]pyrrolidin-1-ylcarbonylmethyl}carbamoyl)benzyl]carbamoylmethoxy}-2,3,4,5-tetrahydro-1,2,5-benzothiadiazepine;

1,1-Dioxo-3,3-dibutyl-5-phenyl-7-methylthio-8-[N—((R)-α-{N-[2-(3,4,5-trihydroxyphenyl)ethyl] carbamoyl}benzyl)carbamoylmethoxy]-2,3,4,5-tetrahydro-1,2,5-benzothiadiazepine; and 1,1-Dioxo-3,3-dibutyl-5-phenyl-7-methylthio-8-(N—{(R)-α-[N-(2-(R)-3-(S)-4-(S)-5-(R)-3,4,5,6-tetrahydroxytetrahydropyran-2-ylmethyl)carbamoyl] benzyl}carbamoylmethoxy)-2,3,4,5-tetrahydro-1,2,5-benzothiadiazepine;

or a pharmaceutically acceptable salt, solvate, solvate of such a salt or a prodrug thereof.

Further suitable compounds possessing MAT inhibitory for use in combination with compounds of the present invention are disclosed in WO 03/106482

Suitable IBAT inhibitors having the above structure for use in combination with compounds of the present invention are selected from any one of:

1,1-dioxo-3,3-dibutyl-5-phenyl-7-methylthio-8-(N—{(R)-α-[N'—((S)-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxypropyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxybutyl) carbamoyl] benzyl}carbamoylmethoxy)-2,3,4,5-tetrahydro-1,5-benzothiazepine;

1,1-dioxo-3,3-dibutyl-5-phenyl-7-methylthio-8-(N—{(R)—α-[N'—((S)-1-carboxy-2-methylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-3-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-hydroxypropyl)carbamoyl]benzyl}carbamoylmethoxy)-2,3,4,5-tetrahydro-1,5-benzothiazepine;

1,1-dioxo-3,3-di butyl-5-phenyl-7-methylthio-8-(N—{(R)-α-[N'—((S)-1-carboxy-2-mesylethypcarbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-3-methylsulphonylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-3-mesylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxybutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-methylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-3-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-hydroxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-hydroxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-methylthioethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-methylsulphinylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-mesylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-2-methoxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-3-methylthiopropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-3-methylsulphonylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxy-3-mesylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-α-[N'—((S)-1-carboxypropyl)carbamoyl]-4-hydroxybenzyl}carbamoylmethoxy)-2,3,4,5-tetrahydro-1,5-benzothiazepine; or 1,1-dioxo-3,3-dibutyl-5-phenyl-7-methylthio-8-(N—{(R)-α-[N'—((S)-1-carboxyethyl) carbamoyl]benzyl}carbamoylmethoxy)-2,3,4,5-tetrahydro-1,5-benzothiazepine.

or a pharmaceutically acceptable salt, solvate, solvate of such a salt or a prodrug thereof.

Further suitable IBAT inhibitors for use in combination with compounds of the present invention are those disclosed in WO 04/076430.

In a particular aspect of the invention an IBAT inhibitor or a pharmaceutically acceptable salt, solvate, solvate of such a salt or a prodrug thereof is an IBAT inhibitor or a pharmaceutically acceptable salt thereof.

Therefore in an additional feature of the invention, there is provided a combination of a compound of formula (I), or a pharmaceutically acceptable salt, solvate, solvate of such a salt or a prodrug thereof and an IBAT inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an MAT inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) an MAT inhibitor, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) an MAT inhibitor, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in the manufacture of a medicament for use in the production of a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an MAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an IBAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, the compound of formula (I), or a pharmaceutically acceptable salt, solvate, solvate of such a salt or a prodrug thereof, may be administered in association with a PPAR alpha and/or gamma and/or delta agonist, or pharmaceutically acceptable salts, solvates, solvates of such salts or prodrugs thereof. Suitable PPAR alpha and/or gamma and/or delta agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO 01/40172, WO 02/085844, WO 02/096863, WO03/051821, WO03/051822, WO03/051826, WO 04/000790, WO04/000295, WO04/000294, PCT/GB03/02584, PCT/GB03/02591, PCT/GB03/02598, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma and/or delta agonist refers to muraglitazar (BMS 298585), rivoglitazone (CS-011), netoglitazone (MCC-555), balaglitazone (DRF-2593, N,N-2344), clofibrate, fenofibrate, bezafibrate, gemfibrozil, ciprofibrate, beclofibrate, etofibrate, gemcabene, pioglitazone, rosiglitazone, edaglitazone, LY-293111, MBX-2044, AVE-0847, AVE-8134, CLX-0921, DRF-10945, DRF-4832, LY-518674, naveglitazar (LY-818), LY-929, 641597, GW-590735, GW-677954, GW-501516, metaglidazen (MBX-102), T-131, SDX-101 E-3030, PLX-204, ONO-5129, KRP-101, R-483 (BM131258), TAK-559, K-111 (BM170744), netoglitazone (MCC-555; RWJ-241947; isaglitazone), FK-614 or TAK-654

Particularly a PPAR alpha and/or gamma and/or delta agonist refers to (S)-2-ethoxy-3-[4-(2-{4-methanesulphonyloxyphenyl}ethoxy)phenyl]propanoic acid (tesaglitazar) and pharmaceutically acceptable salts thereof.

Therefore in an additional feature of the invention, there is provided a combination of a compound of formula (I), or a pharmaceutically acceptable salt, solvate, solvate of such a salt or a prodrug thereof and a PPAR alpha and/or gamma agonist, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma and/or delta agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) a PPAR alpha and/or gamma and/or delta agonist, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) a PPAR alpha and/or gamma and/or delta agonist, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof, in the manufacture of a medicament for use in producing a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma and/or delta agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an -agonists to the receptor HM74A (nicotinic acid receptor). HM74A receptor agonists may be nicotine acid derivates. As used herein "nicotinic acid derivative" means a compounds comprising a pyridine-3-carboxylate structure or a pyrazine-2-carboxylate structure. Examples of nicotinic acid derivatives include nicotinic acid, niceritrol, nicofuranose, NIASPAN® and acipimox.

HM74A receptor agonists may be anthranilic acid derivatives described in WO-2005016867 and WO-2005016870.

Other nicotinic receptor agonists are for example compounds described in WO2005011677, WO2004032928 and WO2004033431.

Therefore, in an additional feature of the invention, there is provided a combination of a compound of formula (I), or a pharmaceutically acceptable salt, solvate, solvate of such a salt or a prodrug thereof and a HM74A receptor agonists or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a HM74A receptor agonists, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a HM74A receptor agonists, or a pharmaceutically acceptable salt, solvate, solvate of such a salt or a prodrug thereof, in association with a pharmaceutically acceptable diluent or carrier.

In another aspect of the invention, there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a mediator of reverse cholesterol transport i.e. a peptide (Apo A-1 mimetic peptides) or small molecule mediator of reverse cholesterol transport e.g. those described in Circ. 2002; 105:290, Circ. 2004.109:3215, Curr. Opinion in Lipidology 2004, 15:645 or in WO2004094471.

In another aspect of the invention, the compound of formula I, or a pharmaceutically acceptable salt or solvate thereof, or a solvate of such a salt, may be administered in association with an anti-obesity compound, or pharmaceutically acceptable salts, solvates, solvates of such salts or prodrugs thereof, for example a pancreatic lipase inhibitor e.g. orlistat (EP 129,748) or an appetite (satiety) controlling substance for example sibutramine (GB 2,184,122 and U.S. Pat. No. 4,929,629), a cannabinoid 1 (CB1) antagonist or inverse agonist, or pharmaceutically acceptable salts, solvates, solvates of such salts or prodrugs thereof, for example rimonabant (EP 656354) and as described in WO01/70700 or a melanin concentrating hormone (MCH) antagonist, or pharmaceutically acceptable salts, solvates, solvates of such salts or prodrugs thereof, for example as described in WO 04/004726.

According to another feature of the invention there is provided the use of a compound of the formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula (I), or a pharmaceutically acceptable salt, solvate, solvate of such a salt or a prodrug thereof, may be administered in association with a bile acid sequestrant or a pharmaceutically acceptable salt, solvate, solvate of such a salt or a prodrug thereof. Suitable bile acid sequestrants include cholestyramine, cholestipol and cosevelam hydrochloride.

Therefore, in an additional feature of the invention, there is provided a combination of a compound of formula (I), or a pharmaceutically acceptable salt, solvate, solvate of such a salt or a prodrug thereof and a bile acid sequestrant or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid sequestrant, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula I, or a pharmaceutically acceptable salt or solvate thereof, or a solvate of such a salt, may be administered in association with a cholesteryl ester transfer protein (CETP) inhibitor, or pharmaceutically acceptable salts, solvates, solvates of such salts or prodrugs thereof, for example JTT-705, torcetrapib (CP-529414), Bay 194789 and those referenced and described in WO05033082 or WO 00/38725 page 7 line 22-page 10, line 17 which are incorporated herein by reference.

In another aspect of the invention, the compound of formula I, or a pharmaceutically acceptable salt or solvate thereof, or a solvate of such a salt, may be administered in association with a acyl coenzymA: cholesterol O-acyltransferase (ACAT) inhibitor, or pharmaceutically acceptable salts, solvates, solvates of such salts or prodrugs thereof, for example pactimibe (CS-505), eflucimibe (F-12511) and SMP-797, avasimibe or K604.

In yet another aspect of the invention, the compound of formula I, association with modulators for example GW-4064 and INT-747 of nuclear receptors such as farnesoid or a pharmaceutically acceptable salt or solvate thereof, or a solvate of such a salt, may be administered in X receptor (FXR), or pharmaceutically acceptable salt, solvate, solvate of such a salt or a prodrug thereof.

In another aspect of the invention, the compound of formula I, or a pharmaceutically acceptable salt or solvate thereof, or a solvate of such a salt, may be administered in association with a phytosterol compound, or pharmaceutically acceptable salts, solvates, solvates of such salts or prodrugs thereof, for example stanols. An example of phytosterol analogs is FM-VP4.

In another aspect of the invention, the compound of formula I, or a pharmaceutically acceptable salt or solvate thereof, or a solvate of such a salt, may be administered in association with other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt or solvate thereof, or a solvate of such a salt, may be administered in association with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from Group X:

an antihypertensive compound (for example althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzemine hydrochloride, prazosin hydrochloride, primidolol, quinapril hydrochloride, quinaprilat, ramipril, terazosin hydrochloride, candesartan, candesartan cilexetil, tehnisartan, amlodipine besylate, amlodipine maleate and bevantolol hydrochloride);

an angiotensin converting enzyme inhibitor (for example alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat);

an angiotensin II receptor antagonist (for example candesartan, candesartan cilexetil, losartan, valsartan, irbesartan, tasosartan, telmisartan and eprosartan);

an andrenergic blocker (for example bretylium tosylate, dihydroergotamine so mesylate, phentolamine mesylate, solypertine tartrate, zolertine hydrochloride, carvedilol or labetalol hydrochloride); an alpha andrenergic blocker (for example fenspiride hydrochloride, labetalol hydrochloride, proroxan and alfuzosin hydrochloride); a beta andrenergic blocker (for example acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate and nebivolol); or a mixed alpha/beta andrenergic blocker;

an andrenergic stimulant (for example combination product of chlorothiazide and methyldopa, the combination product of methyldopa hydrochlorothiazide and methyldopa, clonidine hydrochloride, clonidine, the combination product of chlorthalidone and clonidine hydrochloride and guanfacine hydrochloride);

channel blocker, for example a calcium channel blocker (for example clentiazem maleate, amlodipine besylate, isradipine, nimodipine, felodipine, nilvadipine, nifedipine, teludipine hydrochloride, diltiazem hydrochloride, belfosdil, verapamil hydrochloride or fostedil);

a diuretic (for example the combination product of hydrochlorothiazide and spironolactone and the combination product of hydrochlorothiazide and triamterene);

anti-anginal agents (for example amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen or verapamil hydrochloride);

vasodilators for example coronary vasodilators (for example fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol and verapamil);

anti-coagulants (selected from argatroban, bivalirudin, dalteparin sodium, desirudin, dicumarol, Iyapolate sodium, nafamostat mesylate, phenprocoumon, tinzaparin sodium and warfarin sodium);

antithrombotic agents (for example anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab and zolimomab aritox);

fibrinogen receptor antagonists (for example roxifiban acetate, fradafiban, orbofiban, lotrafiban hydrochloride, tirofiban, xemilofiban, monoclonal antibody 7E3 and sibrafiban)> platelet inhibitors (for example cilostezol, clopidogrel bisulfate, epoprostenol, epoprostenol sodium, ticlopidine hydrochloride, aspirin, ibuprofen, naproxen, sulindae, indomethacin, mefenamate, droxicam, diclofenac, sulfinpyrazone and piroxicam, dipyridamole);

platelet aggregation inhibitors (for example acadesine, beraprost, beraprost sodium, ciprostene calcium, itezigrel, lifarizine, lotrafiban hydrochloride, orbofiban acetate, oxagrelate, fradafiban, orbofiban, tirofiban and xemilofiban)> hemorrheologic agents (for example pentoxifylline);

lipoprotein associated coagulation inhibitors;

Factor Vila inhibitors;

Factor Xa inhibitors;

low molecular weight heparins (for example enoxaparin, nardroparin, dalteparin, certroparin, pamaparin, reviparin and tinzaparin);

squalene synthase inhibitors;

liver X receptor (LXR) agonists for example GW-3965 and those described in WO00224632, WO00103705, WO02090375 and WO00054759 (claim 1 and the named examples of these four application are incorporated herein by reference);

microsomal triglyceride transfer protein inhibitors for example implitapide, CP-346086, JTT-130, BMS-201038, R-103757 and those described in WO05/021486, WO03004020, WO03002533, WO02083658 and WO 00242291 (claim 1 and the named examples of these four application are incorporated herein by reference);

ApoA1 expression inducer for example those described in WO2005032559 or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Therefore, in an additional feature of the invention, there is provided a combination of a compound of formula (I), or a pharmaceutically acceptable salt, solvate, solvate of such a salt or a prodrug thereof and a compound from Group X or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a compound from Group X, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in the manufacture of a medicament for use in the production of a cholesterol lowering effect in a warm-blooded animal, such as man.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of cholesterol absorption in laboratory animals such as cats, dogs, rabbits, monkeys, rats and mice, as part of the search for new therapeutic agents.

What has been described above regarding the combination therapy with a compound of formula (I), and the use of a compound of formula (I) for the treatment or prophylaxis of various diseases and conditions also apply for compound (I2).

Many of the intermediates described herein are novel and are thus provided as a further feature of the invention. For example compounds of formula (XVI) show cholesterol absorption inhibitory activity when tested in the above referenced in vitro test assay and are thus claimed as a further feature of the invention.

Thus in a further feature of the invention, there is provided a compound of formula (XVI), or a pharmaceutically acceptable salt, solvate, solvate of such a salt or a prodrug thereof.

Therefore according to a further aspect of the invention there is provided a pharmaceutical composition which comprises a compound of formula (XVI), or a pharmaceutically acceptable salt, solvate, solvate of such a salt or a prodrug thereof in association with a pharmaceutically-acceptable diluent or carrier.

According to an additional aspect of the present invention there is provided a compound of the formula (XVI), or a pharmaceutically acceptable salt, solvate, solvate of such a salt or a prodrug thereof, for use in a method of prophylactic or therapeutic treatment of a warm-blooded animal, such as man.

Thus according to this aspect of the invention there is provided a compound of the formula (VI), or a pharmaceutically acceptable salt, solvate, solvate of such a salt or a prodrug thereof, for use as a medicament.

According to another feature of the invention there is provided the use of a compound of the formula (XVI), or a pharmaceutically acceptable salt, solvate, solvate of such a salt or a prodrug thereof, in the manufacture of a medicament for use in the production of a cholesterol absorption inhibitory effect in a warm-blooded animal, such as man.

According to another feature of the invention there is provided the use of a compound of the formula (XVI) or a pharmaceutically acceptable salt, solvate, solvate of such a salt or a prodrug thereof, in the manufacture of a medicament for use in the treatment of hyperlipidaemic conditions in a warm-blooded animal, such as man.

According to a further feature of this aspect of the invention there is provided a method for producing a cholesterol absorption inhibitory effect in a warm-blooded animal, such as man, in need of such treatment which comprises administering to said animal an effective amount of a compound of formula (XVI), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (XVI), or a pharmaceutically acceptable salt, solvate, solvate of such a salt or a prodrug thereof.

In the above other pharmaceutical composition, process, method, use and medicament manufacture features, the alternative and preferred embodiments of the compounds of the invention described herein also apply.

EXAMPLES

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18-25° C., with solvents of HPLC grade under anhydrous conditions, unless otherwise stated;

(iii) column chromatography (by the flash procedure) was performed on Silica gel 40-63 μm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated $CDCl_3$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer unless otherwise stated data was recorded at 400 MHz; and peak multiplicities are shown as follows:

s, singlet; d, doublet; dd, double doublet; t, triplet; tt, triple triplet; q, quartet; tq, triple quartet; m, multiplet; br, broad; ABq, AB quartet; ABd, AB doublet, ABdd, AB doublet of doublets; dABq, doublet of AB quartets;

Mass spectra were recorded on one of the following instruments: LCT, QTOF, ZQ Mass spectrometer, all from Waters.

LC-MS:

Separation was performed using Agilent 1100 Series Modules or Waters 1525 pump on a Synergi MAX-RP (Phenomenex) C12 3×50 mm 4 μm with gradient elution.

Samples were injected using Waters 2700 Sample Manager.

Mobile Phases:

Generic gradients were applied from 5% to 95% acetonitrile.

Buffers containing 10 mM ammonium acetate or 5 mM ammonium formiate/5 mM formic acid were used.

The mass spectra were recorded with a Waters ZQ2000 or Waters ZMD equipped with an electrospray interface, swithing positive and negative ionization mode. UV spectra were collected by a Aglent 1100 PDA or Waters 2996 DAD and the evaporative light scattering (ELS) signal by a Sedere Sedex 55 or 75.

Data collection and evaluation were performed using the MassLynx software.

Accurate mass data were determined using either a LCT or QTOF MS (Waters) with leucine enkephalin (m/z 556.2771) as lockmass. Unless otherwise stated the mass ion quoted is ($MH^+$).

Unless further details are specified in the text, analytical high performance liquid chromatography (HPLC) was performed on Prep LC 2000 (Waters), Cromasil $C_8$, 7 μm, (Akzo Nobel); MeCN and de-ionised water 10 mM ammonium acetate as mobile phases, with suitable composition;

(vii) intermediates were not generally fully characterised and purity was assessed by thin layer chromatography (TLC), HPLC, infra-red (IR), MS or NMR analysis;

(viii) where solutions were dried sodium sulphate was the drying agent; and (ix) the following abbreviations may be used hereinbefore or hereinafter:—

DCM dichloromethane;

DMF N,N-dimethylformamide;

TBTU o-Benzotriazol-1-yl-N,N,N',N'-tetramethyluronium tetrafluoroborate;

EtOAc ethyl acetate;

MeCN acetonitrile;

TFA trifluoroacetic acid;

DMAP 4-(dimethylamino)pyridine;

BSA N,O-Bis(trimethylsilypacetamide; and

TBAF tetrabutylammonium fluoride;

NMM N-methyl morpholine;

TEA triethylamine;

DBN 1,5-diazabicyclo-[4,3,0]-non-5-ene.

Example 1

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-3-cyclohexyl-D-alanine To a stirred solution of {4-[(2R,3R)-3-{[2-(2,3-dihydro-1-benzofuran-5-yl)-2-oxoethyl]thio}-1-(4-fluorophenyl)-4-oxoazetidin-2-yl]phenoxy}acetic acid (Method 2) (15.7 mg, 0.031 mmol) in DMF (2 ml, dry) was added N-methylmorpholine (10 μl, 0.091 mmol). TBTU (13.1 mg, 0.041 mmol) and additional DMF (2 ml) were added and the reaction mixture was stirred under at 30° C. for 25 minutes. Glycyl-3-cyclohexyl-D-alanine (7.1 mg, 0.031 mmol) (Method 7) was added and the reaction mixture was stirred for 2 hours. The formation of the ketone of the title compound was confirmed. M/z: 716.57 (M−1). Without further purification, methanol (6 ml) and sodium borohydride (16.1 mg, 0.043 mmol) were added and the reaction mixture was stirred for 20 minutes. Ammonium acetate (85.5 mg) was added. The methanol was removed under reduced pressure and the remaining DMF-solution was purified with preparative HPLC on a C8 column. A gradient from 20 to 55% MeCN in 0.1M $NH_4OAc$ was used as eluent. The pure fractions were collected and the MeCN was removed under reduced pressure. The residue was extracted between EtOAc and water, the water phase was acidified to pH 2 with $KHSO_4$ (2M). The phases were separated and the organic phase was passed through a phase separator. The solvent was removed under reduced pressure. The residue was dissolved in ACN and water. After lyophilisation, the title compound was obtained. H-NMR (400 MHz, DMSO-$d_6$): 0.69-1.67 (m, 13H), 2.76-2.91 (m, 2H), 2.98-311 (m, 2H), 3.75 (d, 2H), 4.15-4.25 (m, 2H), 4.40-4.47 (m, 2H), 4.49 (s, 2H), 4.55-4.64 (m, 1H), 5.00 (b, 1H), 5.54 (b, 1H), 6.61 (dd, 1H), 6.96 (d, 3H), 7.08-7.16 (m, 3H), 7.18-7.24 (m, 2H), 7.34 (d, 2H), 8.07 (d, 1H), 8.19 (t, 1H), 12.51 (b, 1H). M/z: 718.57 (M−1).

Example 2

N-({4-[(2R,3R)-3-{[2-(2,3-dihydro-1H-inden-5-yl)-2-hydroxyethyl]thio}-1-(4-fluorophenyl)-4-oxoazetidin-2-yl]phenoxy}acetyl)glycyl-3-cyclohexyl-D-alanine To a solution of {4-[(2R,3R)-3-{[2-(2,3-dihydro-1H-inden-5-yl)-2-oxoethyl]thio}-1-(4-fluorophenyl)-4-oxoazetidin-2-yl]phenoxy}acetic acid (0.020 g, 0.040 mmol in DMF (1 ml) was added N-methylmorpholine (0.010 g, 0.099 mmol) followed by the addition of 3,4-dichlorophenol (0.008 g, 0.051 mmol) and TBTU (0.013 g, 0.040 mmol). After 2 h, the intermediate 3,4-dichlorophenylester (3,4-dichlorophenyl {4-[(2R,3R)-3-{[2-(2,3-dihydro-1H-inden-5-yl)-2-oxoethyl]thio}-1-(4-fluorophenyl)-4-oxoazetidin-2-yl]phenoxy}acetate) had been formed. Glycyl-3-cyclohexyl-D-alanine (0.011 g, 0.048 mmol) and lithium chloride (0.025 g, 0.593 mmol) were added and the mixture was allowed to stir at room temperature for 2 h. Methanol (1 ml) was added followed by the addition of $NaBH_4$ (0.022 g, 0.593 mmol). Full conversion to the corresponding alcohol had been obtained within 5 minutes. The mixture was purified through preparative HPLC using an eluent of 10-50% $CH_3CN$ in 0.1M $NH_4OAc$ buffer. Freeze drying of pure fractions afforded the desired compound. $^1H$ NMR [$(CD_3)_2SO$), 400 MHz] δ 0.72-1.66 (m, 13H), 1.89-1.98 (m, 2H), 2.69-2.89 (m, 6H), 3.73 (d, 2H), 4.09-4.15 (m, 1H), 4.22 (d, 1H), 4.48 (s, 2H), 4.59-4.67 (m, 1H), 4.98 (d, 1H), 6.95-7.34 (m, 11H), 7.88-7.95 (m, 1H), 8.22 (t, 1H).

Example 3

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-D-lysine To a stirred solution of N-({4-[(2R,3R)-3-{[2-(2,3-dihydro-1-benzofuran-5-yl)-2-oxoethyl]thio}-1-(4-fluorophenyl)-4-oxoazetidin-2-yl]phenoxy}acetyl) (53.4 mg, 0.095 mmol) in DCM (2 ml) were added EDC (24.2 mg, 0.13 mmol) and tert-butyl $N^6$-(tert-butoxycarbonyl)-D-lysinate hydrochloride (38.8 mg, 0.11 mmol). DMAP (12.5 mg, 0.10 mmol) was added and the reaction mixture was stirred for 1 hour. The formation of the intermediate was confirmed; M/z: 849.58 (M+1) and 847.69 (M−1). Additional DCM (3 ml) and TFA (2 ml) were added and the reaction mixture was stirred for 1.5 hours. Analysis with LC-MS showed complete hydrolysis, M/z: 693.46 (M+1). The solvent was removed under reduced pressure and the residue was dissolved in methanol (4 ml). Sodium borohydride (38.8 mg, 1.03 mmol) was added and the reaction mixture was stirred for 30 minutes. Ammonium acetate (80 mg) was added. The solvent was removed under reduced pressure and the residue was purified with preparative HPLC on a C8 column. A gradient from 20 to 60% MeCN in 0.1M $NH_4OAc$ buffer was used as eluent. The pure fractions were collected and lyophilised to give the title compound. H-NMR (400 MHz, DMSO-$d_6$): 1.07-1.65 (m, 8H), 2.54-2.72 (m, 2H), 2.75-2.96 (m, 2H), 3.01-3.10 (m, 2H), 3.64-3.72 (m, 2H), 3.72-3.78 (m, 1H), 4.24 (bd, 1H), 4.44 (t, 2H), 4.49 (s, 2H), 4.55-4.61 (m, 1H), 5.00 (b, 1H), 5.74 (b, 1H), 6.58-6.64 (m, 1H), 6.93-7.00 (m, 3H), 7.08-7.16 (m, 3H), 7.17-7.24 (m, 2H), 7.34 (d, 1H), 7.46 (d, 1H), 8.38 (t, 1H). M/z: 693.52 (M−1).

Example 4

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-3-methyl-D-valine To a stirred solution of N-({4-[(2R,3R)-3-{[2-(2,3-dihydro-1-benzofuran-5-yl)-2-oxoethyl]thio}-1-(4-fluorophenyl)-4-oxoazetidin-2-yl]phenoxy}acetyl)glycine (53.4 mg, 0.095 mmol) in DMF (5 ml) were added N-methylmorpholine (35 μl, 0.32 mmol) and 3,4-dichlorophenol (19 mg, 0.12 mmol). TBTU (35 mg, 0.11 mmol) was added and the reaction mixture was stirred overnight. 3-methyl-D-valine (14.4 mg, 0.11 mmol) and lithium chloride (35.7 mg, 0.84 mmol) were added and the reaction mixture was stirred for 2.5 hours. The formation of the ketone of the title compound was confirmed, M/z: 678.24 (M+1) and 676.26 (M−1). Methanol (4 ml) and sodium borohydride (94.7 mg, 2.5 mmol) were added and the reaction mixture was stirred for 30 minutes. Ammonium acetate (115 mg) was added and some of the solvent was removed under reduced pressure. The remaining DMF-solution was purified with preparative HPLC on a C8 column. A gradient from 20 to 60% MeCN in 0.1M $NH_4OAc$ was used as eluent. The pure fractions were collected and the MeCN was removed under reduced pressure. The remaining water solution was diluted with DCM. The water phase was acidified with $KHSO_4$ (2M) to pH ca 2. The phases were separated and the organic phase was passed through a phase separator. The solvent was removed under reduced pressure. The residue was dissolved in MeCN and water. After lyophilisation the title compound was obtained. 1H-NMR (400 MHz, DMSO-$d_6$): 0.84-0.89 (s, 9H), 2.75-2.92 (m, 2H), 2.97-3.11 (m, 2H), 3.79 (d, 2H), 4.01 (bd, 1H), 4.21-4.27 (m, 1H), 4.44 (t, 2H), 4.49 (s, 2H), 4.55-4.65 (m, 1H), 5.00 (b, 1H), 5.48 (b, 1H), 6.58-6.64 (m, 1H), 6.92-7.00 (m, 3H), 7.08-7.16 (m, 3H), 7.17-7.24 (m, 2H), 7.34 (d, 2H), 7.57-7.91 (m, 1H), 8.24 (bt, 1H). M/z: 678.31 (M−1).

Example 5

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-b,b-dimethyl-D-phenylalanine To a stirred solution of N-({4-[(2R,3R)-3-{[2-(2,3-dihydro-1-benzofuran-5-yl)-2-oxoethyl]thio}-1-(4-fluorophenyl)-4-oxoazetidin-2-yl]phenoxy}acetyl) (55.6 mg, 0.098 mmol) in DMF (4 ml) were added N-methylmorpholine (45 μl, mmol) and 3,4-dichlorophenol (21 mg, 0.13 mmol). TBTU (39 mg, 0.12 mmol) was added and the reaction mixture was stirred overnight. β,β-dimethyl-D-phenylalanine trifluoroacetate (37.4 mg, 0.12 mmol) and lithium chloride (45 mg, 1.06 mmol) were added and the reaction mixture was stirred for 3 hours. The formation of the ketone of the title compound was confirmed; M/z: 740.25 (M+1) and 738.32 (M−1). Methanol (4 ml) and sodium borohydride (94.7 mg, 2.5 mmol) were added and the reaction mixture was stirred for 1 hour. Ammonium acetate (115 mg) was added and some of the solvent was removed under reduced pressure. The remaining DMF-solution was purified with preparative HPLC on a C8 column. A gradient from 20 to 70% MeCN in 0.1M $NH_4OAc$ buffer was used as eluent. The pure fractions were collected and the MeCN was removed under reduced pressure. The remaining water solution was diluted with DCM. The water phase was acidified with $KHSO_4$ (2M) to pH ca 2. The phases were separated and the organic phase was passed through a phase separator. The solvent was removed under reduced pressure. The residue was dissolved in MeCN and water. After lyophilisation, the title compound was obtained. H-NMR (400 MHz, DMSO-$d_6$): 1.27 (s, 3H), 1.30 (s, 3H), 2.79-2.89 (m, 2H), 2.97-3.11 (m, 2H), 3.58-3.82 (m, 2H), 4.22 (b, 1H), 4.39-4.48 (m, 4H), 4.59 (b, 2H), 5.00 (b, 1H), 5.43 (b, 1H), 6.58-6.63 (m, 1H), 6.91-6.99 (m, 3H), 7.06-7.15 (m, 4H), 7.17-7.25 (m, 4H), 7.27-7.36 (m, 4H), 7.82 (b, 1H), 8.18 (t, 1H). M/z: 740.35 (M−1).

Example 6

N-{[4-((2R,3R)-1-(4-fluorophenyl)-3-{[(2R)-2-hydroxy-2-(5,6,7,8-tetrahydronaphthalen-2-yl)ethyl]thio}-4-oxoazetidin-2-yl)phenoxy]acetyl}glycyl-3-cyclohexyl-D-alanine To a solution of [4-((2R,3R)-1-(4-fluorophenyl)-3-{[(2R or S)-2-hydroxy-2-(5,6,7,8-tetrahydronaphthalen-2-yl)ethyl]thio}-4-oxoazetidin-2-yl)phenoxy]acetic acid (0.021 g, 0.04 mmol) in DMF (0.5 ml) under an atmosphere of nitrogen was added N-methylmorpholine (0.010 g, 0.10 mmol) followed by the addition of 4-chlorophenol (0.007 g, 0.05 mmol) and TBTU (0.013 g, 0.04 mmol). After 1 h, full conversion to the 4-chlorophenylester intermediate (4-chlorophenyl[4-((2R,3R)-1-(4-fluorophenyl)-3-{[(2R)-2-hydroxy-2-(5,6,7,8-tetrahydronaphthalen-2-yl)ethyl]thio}-4-oxoazetidin-2-yl)phenoxy]acetate) had been obtained. Glycyl-3-cyclohexyl-D-alanine (0.012 g, 0.05 mmol) and lithium chloride (0.026 g, 0.60 mmol) were added and the mixture was allowed to stir at room temperature for three days. Full conversion to the desired product had now been obtained. The mixture was purified through preparative HPLC using an eluent of 0-45% $CH_3CN$ in 0.1M $NH_4OAc$ buffer. Freeze drying of pure fractions afforded the desired compound. $^1H$ NMR [$(CD_3)_2SO$), 400 MHz] δ 0.70-1.68 (m, 17H), 2.58-2.66 (m, 4H), 2.82 (dd, 1H), 2.86 (dd, 1H), 3.73 (d, 2H), 4.09-4.15 (m, 1H), 4.23 (d, 1H), 4.48 (s, 2H), 4.56 (t, 1H), 4.98 (d, 1H), 6.90-7.34 (m, 11H), 7.92 (d, 1H), 8.22 (t, 1H).

Example 7

N-({4-[(2R,3R)-3-{[(2R or S)-2-(2,3-dihydro-1H-inden-5-yl)-2-hydroxyethyl]thio}-1-(4-fluorophenyl)-4-oxeazetidin-2-yl]phenoxy}acetyl)glycyl-3-cyclohexyl-D-alanine The titled compound was obtained as a pure diastereomer upon separation from a 50:50 diastereomeric mixture of N-({4-[(2R,3R)-3-{[2-(2,3-dihydro-1H-inden-5-yl)-2-hydroxyethyl]thio}-1-(4-fluorophenyl)-4-oxoazetidin-2-yl]phenoxy}acetyl)glycyl-3-cyclohexyl-D-alanine using the following conditions: Column R,R-Whelk-O1, 250X 21.2 mm, particle size 10 μm, mobile phase Heptane/EtOH/$HCO_2H$ 70/30/0.1, flow 15 ml/min, detection 254 nm, sample concentration 9.5 mg/ml in heptane/ethanol 70/30. The titled diastereomer is the second eluting one in this system. $^1H$ NMR [$(CD_3)_2SO$), 400 MHz]δ 0.72-1.69 (m, 13H), 1.89-1.98 (m, 2H), 2.72-2.90 (m, 6H), 3.75 (d, 2H), 4.14-4.21 (m, 1H), 4.22 (d, 1H), 4.48 (s, 2H), 4.58-4.64 (m, 1H), 4.98 (d, 1H), 6.94-7.34 (m, 11H), 8.02-8.06 (m, 1H), 8.17-8.23 (m, 1H).

Example 8

N-({4-[(2R,3R)-3-{[(2R or S)-2-(2,3-Dihydro-1-benzofuran-5-yl)-2-hydroxyethyl]thio}-1-(4-fluorophenyl)-4-oxoazetidin-2-yl]phenoxy}acetyl)glycyl-3-cyclohexyl-D-alanine ammoniate N-({4-[(2R,3R)-3-{[(2R)-2-{[tert-Butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-3-cyclohexyl-D-alanine (16 mg, 0.020 mmol) was dissolved in 2 ml dry THY under inert atmosphere. HOAc (0.011 ml, 0.19 mmol) and TBAF (1M in THF, 0.200 ml, 0.20 mmol) were added and the mixture was stirred over the weekend. The solvent was evaporated and the residue was purified by preparative HPLC on a C8 column (300×25 mm) using a gradient from 20% to 35% MeCN in 0.1 M $NH_4OAc$ buffer as eluent. The product fraction was lyophilized to yield 13.5 mg. The solid was dissolved in MeOH (1 ml) and run through a cation-exchange column (400 mg ISOLUTE® SCX-column, IST) pre-equilibrated with ammonia in MeOH. MeOH was used as eluent and the product fraction was concentrated, diluted with water and lyophilized. The title compound was obtained. M/z: 718 (M−1). $^1$H-NMR (400 MHz, DMSO-$d_6$): δ 0.70-0.92 (m, 2H), 1.01-1.20 (m, 3H), 1.21-1.44 (m, 2H), 1.46-1.77 (m, 6H), 2.82-2.96 (m, 2H), 3.10 (t, 2H), 3.75 (d, 2H), 3.99-4.09 (m, 1H), 4.27 (d, 1H), 4.48 (t, 2H), 4.53 (s, 2H), 4.62 (t, 1H), 5.04 (d, 1H), 6.65 (d, 1H), 6.97-7.04 (m, 3H), 7.11-7.20 (m, 3H), 7.21-7.28 (m, 2H), 7.38 (d, 2H), 7.70-7.79 (m, 1H), 8.29 (t, 1H).

Example 9

N-({4-[(2R,3R)-3-{[(2R or S)-2-(2,3-dihydro-1-benzofuran-5-yl)-2-hydroxyethyl]thio}-1-(4-fluorophenyl)-4-oxoazetidin-2-yl]phenoxy}acetyl)glycyl-3-methyl-D-valine To a solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-3-methyl-D-valine (8 mg, 0.010 mmol) in THF (2 ml, dry) were added acetic acid (6 μl, 0.104 mmol) and TBAF (1M in THF, 104 μl, 0.104 mmol). The reaction mixture was stirred over the weekend. Additional TBAF (1M in THF 5.4 μl, 0.0054 mmol) was added and the reaction mixture was stirred overnight. The solvent was removed under reduced pressure and the residue was purified with preparative HPLC on a C8 column, UV 235/285 nm. A gradient from 20 to 65% MeCN in 0.1M $NH_4OAc$ buffer was used as eluent. The pure fractions were collected and most of the MeCN was removed under reduced pressure. The residue was lyophilised to give a white solid. The obtained compound was dissolved in MeOH and run through a cation-exchange column (400 mg SCX, SPE-product). The column was pre-equilibrated with 25% ammonia solution: MeOH (1:3, 3 ml), and washed with MeOH (3 ml). This procedure was repeated once more and the solvent was removed under reduced pressure. The residue was dissolved in MeCN and water. After lyophilisation, the title compound was obtained. H-NMR (400 MHz, DMSO-$d_6$): 0.81 (s, 9H), 2.79-2.92 (m, 2H), 3.03-3.10 (m, 2H), 3.63-3.89 (m, 3H), 4.26 (b, 1H), 4.44 (t, 2H), 4.50 (s, 2H), 4.59 (t, 1H), 4.99 (d, 1H), 6.61 (d, 1H), 6.94-6.99 (m, 3H), 7.08-7.16 (m, 3H), 7.17-7.23 (m, 2H), 7.33 (d, 2H), 8.31 (bs, 1H). M/z: 678.34 (M−1).

Example 10

N-({4-[(2R,3R)-3-{[(2R or S)-2-(2,3-dihydro-1-benzofuran-5-yl)-2-hydroxyethyl]thio}-1-(4-fluorophenyl)-4-oxoazetidin-2-yl]phenoxy}acetyl)glycyl-D-valine To a solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-D-valine (20.0 mg, 0.025 mmol) in THF (2 ml, dry) were added acetic acid (10.4 μl, 0.250 mmol) and TBAF (1M in THF, 268 μl, 0.268 mmol). The reaction mixture was stirred overnight. Additional TBAF (25.6 μl, 0.026 mmol) was added and the reaction mixture was stirred overnight. The solvent was removed under reduced pressure. The residue was purified with preparative HPLC on a C8 column, UV 235/285 nm. A gradient from 20 to 60% MeCN in a 0.1M $NH_4OAc$ buffer was used as eluent. The pure fractions were collected and most of the MeCN was removed under reduced pressure. The residue was acidified with $KHSO_4$ (2M) to pH 3 and extracted from DCM. The organic phase was concentrated. The residue was dissolved in MeOH and run through a cation-exchange column (400 mg SCX, SPE-product) The column was pre-equilibrated with 25% ammonia solution:MeOH (1:3; 3 ml) and washed with MeOH (3 ml). The solvent was removed under reduced pressure. The residue was dissolved in MeCN and water and lyophilised to give the title compound. H-NMR (400 MHz, DMSO-$d_6$): 0.72-0.76 (m, 6H), 1.94-2.02 (m, 1H), 2.79-2.91 (m, 2H), 3.01-3.10 (m, 2H), 3.78 (d, 2H), 3.98-4.07 (m, 1H), 4.22 (d, 1H), 4.44 (t, 2H), 4.49 (s, 2H), 4.58 (t, 1H), 5.00, (d, 1H), 5.44 (bs, 1H), 6.62 (d, 1H), 6.93-7.00 (m, 3H), 7.08-7.15 (m, 3H), 7.17-7.24 (m, 2H), 7.34 (d, 2H), 7.84 (d, 1H), 8.23 (t, 1H). M/z: 664.38 (M−1).

Example 11

N-({4-[(2R,3R)-3-{[(2R or S)-2-(2,3-dihydro-1-benzofuran-5-yl)-2-hydroxyethyl]thio}-1-(4-fluorophenyl)-4-oxoazetidin-2-yl]phenoxy}acetyl)glycyl-4-cyano-D-phenylalanine To a solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-4-cyano-D-phenylalanine (22.2 mg, 0.026 mmol) in THF (2 ml, dry) were added acetic acid (15 μl, 0.260 mmol) and TBAF (1M in THF, 273 μl, 0.273 mmol). The reaction mixture was stirred over the weekend. The solvent was removed under reduced pressure. The residue was purified with preparative HPLC on a C8 column, UV 235/285 nm. A gradient from 20 to 75% MeCN in a 0.1M $NH_4OAc$ buffer was used as eluent. The pure fractions were collected. Most of the MeCN was removed under reduced pressure and the residue was lyophilised to give the title compound. H-NMR (500 MHz, DMSO-$d_6$): 2.82-2.98 (m, 4H), 3.05-3.16 (m, 2H), 3.64-3.79 (m, 2H), 4.24 (bd, 1H), 4.42-4.49 (m, 3H), 4.50 (s, 2H), 4.61 (bt, 1H), 5.03 (bd, 1H), 5.46 (bs, 1H), 6.64 (d, 1H), 6.94-7.02 (m, 4H), 7.11-7.17 (m, 2H), 7.20-7.25 (m, 2H), 7.38 (dd, 4H), 7.70 (d, 2H), 8.19-8.24 (m, 2H). M/z: 737 (M−1).

Example 12

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-$N^6$,$N^6$-dimethyl-L-lysine To a solution of N-({4-[(2R,3R)-3-{[(2R)-2-(2,3-dihydro-1-benzofuran-5-yl)-2-hydroxyethyl]thio}-1-(4-fluorophenyl)-4-oxoazetidin-2-yl]phenoxy}acetyl)glycyl-$N^6$,$N^6$-dimethyl-L-lysine (11.0 mg, 0.013 mmol) in MeCN (1 ml) were added scandium tris(trifluoromethanesulfonate) (0.5 mg, 0.00102 mmol) and water (2 μl, 0.131 mmol). The reaction mixture was stirred for 3 hours. Additional $Sc(OTf)_3$ (0.7 mg, 0.00142 mmol) and water (2 μl, 0.131 mmol) were added and the mixture was stirred for 1 hour. Additional Sscandium tris(trifluoromethanesulfonate) (6.0 mg, 0.01219 mmol)) and water (4 μl, 0.262) were added and the reaction mixture was stirred for 1 hour. Ammonium acetate buffer (0.1M, 1 ml) was added. The resulting solution was purified with preparative HPLC on a C8 column, UV 235/285 nm. A gradient from 20 to 43% MeCN was used as eluent. The pure fractions were collected and most of the MeCN was removed under reduced pressure. The residue was lyophilised to give the title compound. H-NMR (500 MHz, DMSO-$d_6$): 1.21-1.31 (m, 2H), 1.33-1.44 (m, 2H), 1.51-1.60 (m, 1H), 1.63-1.71 (m, 1H), 2.16 (s, 6H), 2.25 (bs, 2H), 2.81-2.94 (m, 2H), 3.01-3.15 (m, 2H), 3.78 (d, 2H), 4.07 (bs, 1H), 4.25 (d, 0.5H) 4.26 (d, 0.5H), 4.44-4.50 (m, 2H), 4.52 (s, 2H), 4.59-4.66 (m, 1H), 5.01-5.05 (b, 1H), 6.64 (dd, 1H), 6.97-7.02 (m, 3H), 7.11-7.18 (m, 3H), 7.21-7.26 (m, 2H), 7.37 (d, 2H), 7.98 (bs, 1H), 8.26 (t, 1H). M/z: 721.40 (M−1)

Example 13

N-({4-[(2R,3R)-3-{[(2R or S)-2-(2,3-dihydro-1-benzofuran-5-yl)-2-hydroxyethyl]thio}-1-(4-fluorophenyl)-4-oxoazetidin-2-yl]phenoxy}acetyl)glycyl-3-methyl-D-isovaline To a solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl] phenoxy}acetyl)glycyl-3-methyl-D-isovaline (10.3 mg, 0.013 mmol) in THF (2 ml, dry) were added acetic acid (8 μl, 0.140 mmol) and TBAF (1M in THF, 145 μl, 0.145 mmol) were added and the reaction mixture was stirred over the weekend. Additional acetic acid (4 μl, 0.070 mmol) and TBAF (1M in THF, 73 μl, 0.073 mmol) were added and the reaction mixture was stirred overnight. Additional acetic acid (8 μl, 0.140 mmol) and TBAF (1M in THF, 145 μl, 0.145 mmol) were added and the reaction mixture was stirred overnight. The solvent was removed under reduced pressure. The residue was purified with preparative HPLC on a C8 column, IN 235/285 nm. A gradient from 20 to 70% MeCN in a 0.1M $NH_4OAc$ was used as eluent. The pure fractions were collected and most of the MeCN was removed under reduced pressure. The remaining was acidified with $KHSO_4$ (2M) to pH 3 and extracted from DCM. The organic phase was concentrated. The residue was dissolved in MeOH (1 ml) and run through a cation-exchange column (400 mg SCX, SPE-product). The column was pre-equilibrated with 25% ammonia solution:MeOH (1:3, 3 ml) and washed with MeOH (3 ml). The solvent was removed under reduced pressure. The residue was dissolved in MeCN and water and lyophilised to give the title compound. H-NMR (400 MHz, DMSO-$d_6$): 0.78 (d, 3H), 0.85 (d, 3H), 1.26 (s, 3H) 1.94-2.02 (m, 1H) 2.79-2.90 (m, 2H), 3.03-3.10 (m, 2H), 3.72 (d, 2H), 4.21 (d, 1H), 4.44 (t, 2H), 4.49 (s, 2H), 4.58 (bt, 1H), 5.00 (d, 1H), 5.43 (bs, 1H), 6.61 (d, 1H), 6.93-6.99 (m, 3H), 7.08-7.15 (m, 3H), 7.17-7.23 (2H), 7.34 (d, 2H), 7.77 (bs, 1H), 8.19 (bt, 1H). M/z: 678.32 (M−1).

Example 14

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycylglycine To a stirred solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl] phenoxy}acetyl)glycylglycine (22.0 mg, 0.030 mmol) in MeCN were added scandium tris(trifluoromethanesulfonate) (0.1 mg, 2 μmol)) and water (3 μl). The reaction mixture was stirred for 1 h. Additional (0.5 mg, 10.2 μmol) was added. The reaction mixture was stirred overnight. LC-MS showed complete desilylation. $NH_4OAc$ buffer (0.1M, 1 ml) was added. The solution was purified with preparative HPLC on a C8 column. A gradient from 20 to 70% MeCN in a 0.1 M $NH_4OAc$ buffer was used as eluent. The pure fractions were collected and most of the MeCN was removed under reduced pressure. The residue was extracted from DCM. The water phase was acidified to pH 3 with $KHSO_4$ (2M). The phases were separated and the organic phase was concentrated. The residue was dissolved in ACN and water and lyophilised to give the title compound. H-NMR (400 MHz, DMSO-$d_6$): 2.77-2.92 (m, 2H), 2.99-3.11 (m, 2H), 3.67 (b, 2H), 3.75 (d, 2H), 4.21-4.25 (m, 1H), 4.44 (dt, 2H), 4.49 (s, 2H), 4.55-4.64 (m, 1H), 5.00 (b, 1H), 5.45 (b, 1H), 6.61 (dd, 1H), 6.96 (d, 3H), 7.06-7.16 (m, 3H), 7.17-7.23 (m, 2H), 7.34 (d, 2H), 8.08 (b, 1H), 8.28 (t, 1H). M/z: 622.23 (M−1).

Example 15

(R)-3-Cyclohexyl-2-[2-(2-{4-[(2R,3R)-3-[2-(2,3-dihydro-benzofuran-6-yl)-2-hydroxy-ethylsulfanyl]-1-(4-fluoro-phenyl)-4-oxo-azetidin-2-yl]-phenoxy}-acetylamino)-acetylamino]-propionic acid To a solution of {4-[(2R,3R)-3-[2-(2,3-dihydro-benzofuran-6-yl)-2-oxo-ethylsulfanyl]-1-(4-fluoro-phenyl)-4-oxo-azetidin-2-yl]-phenoxy}-acetic acid (33 mg, 0.065 mmol) in DMF (3 mL) at RT was added N-methylmorpholine (22 μl, 0.198 mmol) and TBTU (22 mg, 0.069 mmol). The mixture was stirred for 30 min before (R)-2-(2-amino-acetylamino)-3-cyclohexyl-propionic acid (15 mg, 0.066 mmol) was added. After 2 h 30 min, the reaction was quenched by the addition of water (1 mL) The mixture was diluted with MeOH (1 mL) and then added NaBH4 (35 mg, 0.925 mmol). After 15 min, the reaction was quenched by the addition of 1M HCl (3 mL) and the resulting solution was purified by preparative HPLC using a gradient of 0-60% MeCN in a 0.1M ammonium acetate buffer as eluent. Freeze-drying of the pure fractions gave the desired product.

$^1$H-NMR (DMSO, 400 MHz): δ 0.71-0.95 (m, 2H), 1.00-1.72 (m, 1H), 2.80-2.90 (m, 2H), δ 3.05-3.15 (m, 2H), 3.77 (d, 2H), 4.12-4.21 (m, 1H), 4.24-4.29 (m, 1H), 4.42-4.55 (m, 4H), 4.59-4.68 (m, 1H), 4.99-5.05 (m, 1H), 6.67-6.77 (m, 2H), 6.95-7.02 (m, 2H), 7.05-7.27 (m, 5H), 7.32-7.41 (m, 2H), 7.94-8.02 (m, 1H), 8.20-8.28 (m, 1H).

The following compounds could be prepared by the procedure of Example 8, but wherein different protecting groups may be used.

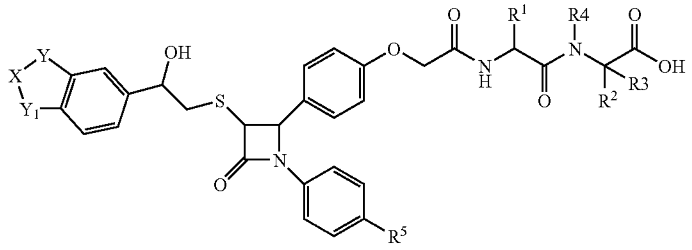

| X | Y | $Y_1$ | $R^1$ | $R^2$ | $R^3$ | $R^4$ | $R^5$ |
|---|---|---|---|---|---|---|---|
| $CH_2CH_2$ | CH2 | O | H | $CH_2C_6H_5$-p-CN | H | H | F |
| $CH_2CH_2$ | CH2 | O | H | cyclohexyl | H | H | F |
| $CH_2CH_2$ | CH2 | O | H | $CH_2$cyclohexyl | H | H | F |
| $CH_2CH_2$ | CH2 | O | H | $CH_2CH_2CH_2NH_2$ | H | H | F |
| $CH_2CH_2$ | CH2 | O | H | $CH_2CH_2CH_2CH_2NH_2$ | H | H | F |
| $CH_2CH_2$ | CH2 | O | H | $C(CH_3)_2C_6H_5$ | H | H | F |
| $CH_2CH_2$ | CH2 | O | H | $CH(CH_3)_2$ | H | H | F |
| $CH_2CH_2$ | CH2 | O | H | $CH_2CH(CH_3)_2$ | H | H | F |
| $CH_2CH_2$ | CH2 | O | H | CH(CH3)2 | $CH_3$ | H | F |
| $CH_2CH_2$ | CH2 | O | H | R2,R4 = $CH_2CH_2CH_2$ | H | R2,R4 = $CH_2CH_2CH_2$ | F |
| $CH_2CH_2$ | CH2 | O | H | $CH_2CH_2CH_2CH_2N(CH_3)_2$ | H | H | F |
| $CH_2CH_2$ | CH2 | O | H | $CH_2SC(CH_3)_3$ | H | H | F |
| $CH_2CH_2$ | CH2 | O | H | $CH_2CH_2CH_2CH_3$ | $CH_2CH_2CH_2CH_3$ | H | F |
| $CH_2CH_2$ | CH2 | O | H | $C(CH_3)_3$ | H | H | F |
| $CH_2CH_2$ | $CH_2$ | O | H | $CH_2C_6H_5$ | H | H | H |
| $CH_2CH_2$ | $CH_2$ | O | H | $CH_2C_6H_5$-p-OH | H | H | H |
| $CH_2CH_2$ | $CH_2$ | O | H | $CH_2C_6H_5$-p-CN | H | H | H |
| $CH_2CH_2$ | $CH_2$ | O | H | cyclohexyl | H | H | H |
| $CH_2CH_2$ | $CH_2$ | O | H | $CH_2$cyclohexyl | H | H | H |
| $CH_2CH_2$ | $CH_2$ | O | H | $CH_2CH_2CH_2NH_2$ | H | H | H |
| $CH_2CH_2$ | $CH_2$ | O | H | $CH_2CH_2CH_2CH_2NH_2$ | H | H | H |
| $CH_2CH_2$ | $CH_2$ | O | H | $C(CH_3)_2C_6H_5$ | H | H | H |
| $CH_2CH_2$ | $CH_2$ | O | H | $CH(CH_3)_2$ | H | H | H |
| $CH_2CH_2$ | $CH_2$ | O | H | $CH_2CH(CH_3)_2$ | H | H | H |
| $CH_2CH_2$ | $CH_2$ | O | H | $CH(CH_3)_2$ | $CH_3$ | H | H |
| $CH_2CH_2$ | $CH_2$ | O | H | R2,R4 = $CH_2CH_2CH_2$ | H | R2,R4 = $CH_2CH_2CH_2$ | H |
| $CH_2CH_2$ | $CH_2$ | O | H | $CH_2CH_2CH_2CH_2N(CH_3)_2$ | H | H | H |
| $CH_2CH_2$ | $CH_2$ | O | H | $CH_2SC(CH_3)_3$ | H | H | H |
| $CH_2CH_2$ | $CH_2$ | O | H | $CH_2CH_2CH_2CH_3$ | $CH_2CH_2CH_2CH_3$ | H | H |
| $CH_2CH_2$ | $CH_2$ | O | H | $C(CH_3)_3$ | H | H | H |
| $CH_2$ | $CH_2$ | O | H | $CH_2C_6H_5$ | H | H | F |
| $CH_2$ | $CH_2$ | O | H | $CH_2C_6H_5$-p-OH | H | H | F |
| $CH_2$ | $CH_2$ | O | H | $CH_2C_6H_5$-p-CN | H | H | F |
| $CH_2$ | $CH_2$ | O | H | $CH_2CH_2CH_2NH_2$ | H | H | F |
| $CH_2$ | $CH_2$ | O | H | $CH_2CH(CH_3)_2$ | H | H | F |
| $CH_2$ | $CH_2$ | O | H | R2,R4 = $CH_2CH_2CH_2$ | H | R2,R4 = $CH_2CH_2CH_2$ | F |
| $CH_2$ | $CH_2$ | O | H | $CH_2SC(CH_3)_3$ | H | H | F |
| $CH_2$ | $CH_2$ | O | H | $CH_2CH_2CH_2CH_3$ | $CH_2CH_2CH_2CH_3$ | H | F |
| $CH_2$ | $CH_2$ | O | H | $CH_2C_6H_5$ | H | H | H |
| $CH_2$ | CH2 | O | H | $CH_2C_6H_5$-p-OH | H | H | H |
| $CH_2$ | CH2 | O | H | $CH_2C_6H_5$-p-CN | H | H | H |
| $CH_2$ | CH2 | O | H | cyclohexyl | H | H | H |
| $CH_2$ | CH2 | O | H | $CH_2$cyclohexyl | H | H | H |
| $CH_2$ | CH2 | O | H | $CH_2CH_2CH_2NH_2$ | H | H | H |
| $CH_2$ | CH2 | O | H | $CH_2CH_2CH_2CH_2NH_2$ | H | H | H |
| $CH_2$ | CH2 | O | H | $C(CH_3)_2C_6H_5$ | H | H | H |
| $CH_2$ | CH2 | O | H | $CH(CH_3)_2$ | H | H | H |
| $CH_2$ | CH2 | O | H | $CH_2CH(CH_3)_2$ | H | H | H |
| $CH_2$ | CH2 | O | H | $CH(CH_3)_2$ | $CH_3$ | H | H |
| $CH_2$ | CH2 | O | H | R2,R4 = $CH_2CH_2CH_2$ | H | R2,R4 = $CH_2CH_2CH_2$ | H |
| $CH_2$ | CH2 | O | H | $CH_2CH_2CH_2CH_2N(CH_3)_2$ | H | H | H |
| $CH_2$ | CH2 | O | H | $CH_2SC(CH_3)_3$ | H | H | H |
| $CH_2$ | CH2 | O | H | $CH_2CH_2CH_2CH_3$ | $CH_2CH_2CH_2CH_3$ | H | H |
| $CH_2$ | CH2 | O | H | $C(CH_3)_3$ | H | H | H |
| $CH_2$ | $CH_2$ | O | H | $CH_2C_6H_5$ | H | H | Cl |
| $CH_2$ | $CH_2$ | O | H | $CH_2C_6H_5$-p-OH | H | H | Cl |
| $CH_2$ | $CH_2$ | O | H | $CH_2C_6H_5$-p-CN | H | H | Cl |
| $CH_2$ | $CH_2$ | O | H | cyclohexyl | H | H | Cl |
| $CH_2$ | $CH_2$ | O | H | $CH_2$cyclohexyl | H | H | Cl |
| $CH_2$ | $CH_2$ | O | H | $CH_2CH_2CH_2NH_2$ | H | H | Cl |

-continued

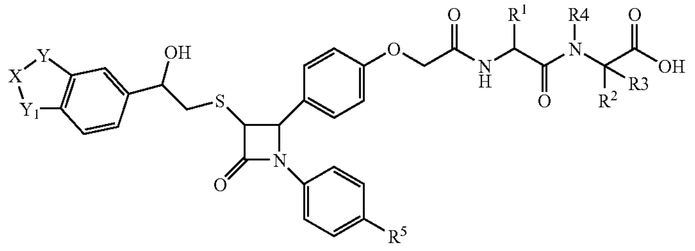

| X | Y | $Y_1$ | $R^1$ | $R^2$ | $R^3$ | $R^4$ | $R^5$ |
|---|---|---|---|---|---|---|---|
| $CH_2$ | $CH_2$ | O | H | $CH_2CH_2CH_2CH_2NH_2$ | H | H | Cl |
| $CH_2$ | $CH_2$ | O | H | $C(CH_3)_2C_6H_5$ | H | H | Cl |
| $CH_2$ | $CH_2$ | O | H | $CH(CH_3)_2$ | H | H | Cl |
| $CH_2$ | $CH_2$ | O | H | $CH_2CH(CH_3)_2$ | H | H | Cl |
| $CH_2$ | $CH_2$ | O | H | $CH(CH_3)_2$ | $CH_3$ | H | Cl |
| $CH_2$ | $CH_2$ | O | H | R2,R4 = $CH_2CH_2CH_2$ | H | R2,R4 = $CH_2CH_2CH_2$ | Cl |
| $CH_2$ | $CH_2$ | O | H | $CH_2CH_2CH_2CH_2N(CH_3)_2$ | H | H | Cl |
| $CH_2$ | $CH_2$ | O | H | $CH_2SC(CH_3)_3$ | H | H | Cl |
| $CH_2$ | $CH_2$ | O | H | $CH_2CH_2CH_2CH_3$ | $CH_2CH_2CH_2CH_3$ | H | Cl |
| $CH_2$ | $CH_2$ | O | H | $C(CH_3)_3$ | H | H | Cl |
| $CH_2$ | $CH_2$ | O | H | $CH_2C_6H_5$ | H | H | $CH_3$ |
| $CH_2$ | $CH_2$ | O | H | $CH_2C_6H_5$-p-OH | H | H | $CH_3$ |
| $CH_2$ | $CH_2$ | O | H | $CH_2C_6H_5$-p-CN | H | H | $CH_3$ |
| $CH_2$ | $CH_2$ | O | H | cyclohexyl | H | H | $CH_3$ |
| $CH_2$ | $CH_2$ | O | H | $CH_2$cyclohexyl | H | H | $CH_3$ |
| $CH_2$ | $CH_2$ | O | H | $CH_2CH_2CH_2NH_2$ | H | H | $CH_3$ |
| $CH_2$ | $CH_2$ | O | H | $CH_2CH_2CH_2CH_2NH_2$ | H | H | $CH_3$ |
| $CH_2$ | $CH_2$ | O | H | $C(CH_3)_2C_6H_5$ | H | H | $CH_3$ |
| $CH_2$ | $CH_2$ | O | H | $CH(CH_3)_2$ | H | H | $CH_3$ |
| $CH_2$ | $CH_2$ | O | H | $CH_2CH(CH_3)_2$ | H | H | $CH_3$ |
| $CH_2$ | $CH_2$ | O | H | $CH(CH_3)_2$ | $CH_3$ | H | $CH_3$ |
| $CH_2$ | $CH_2$ | O | H | R2,R4 = $CH_2CH_2CH_2$ | H | R2,R4 = $CH_2CH_2CH_2$ | $CH_3$ |
| $CH_2$ | $CH_2$ | O | H | $CH_2CH_2CH_2CH_2N(CH_3)_2$ | H | H | $CH_3$ |
| $CH_2$ | $CH_2$ | O | H | $CH_2SC(CH_3)_3$ | H | H | $CH_3$ |
| $CH_2$ | $CH_2$ | O | H | $CH_2CH_2CH_2CH_3$ | $CH_2CH_2CH_2CH_3$ | H | $CH_3$ |
| $CH_2$ | $CH_2$ | O | H | $C(CH_3)_3$ | H | H | $CH_3$ |

Methods for Preparing Starting Materials

N-({4-[(2R,3R)-3-{[2-(2,3-dihydro-1-benzofuran-5-yl)-2-oxoethyl]thio}-1-(4-fluorophenyl)-4-oxoazetidin-2-yl]phenoxy}acetyl)glycine To a stirred solution of {4-[(2R,3R)-3-{[2-(2,3-dihydro-1-benzofuran-5-yl)-2-oxoethyl]thio}-1-(4-fluorophenyl)-4-oxoazetidin-2-yl]phenoxy}acetic acid (166.20 mg, 0.33 mmol) in DCM (10 ml) were added EDC (71.5 mg, 0.37 mmol) and tert-butyl glycinate hydrochloride (65.8 mg, 0.39 mmol). DMAP (21.7 mg, 0.18 mmol) was added and the reaction mixture was stirred for 3.5 hours. The formation of the tert-butyl ester of the title compound was confirmed, M/z: 619 (M−1). TFA (5 ml) was added and the reaction mixture was stirred for 1 hour and 15 minutes. LC-MS showed complete hydrolysis. The solvent was removed under reduced pressure, toluene was used to assist the removal of TFA. The residue was purified with preparative HPLC on a C8 column. A gradient from 20 to 65% MeCN in 0.1M $NH_4OAc$ buffer was used as eluent. The MeCN was removed under reduced pressure and the remaining water solution was diluted with DCM. The water phase was acidified to pH ca 2 with $KHSO_4$ (2M). The phases were separated and the organic phase was passed through a phase separator. The solvent was removed under reduced pressure to give the title compound. H-NMR (400 MHz, DMSO-$d_6$): 3.17 (t, 2H), 3.77 (d, 2H), 4.19-4.28 (m, 2H) 4.29 (d, 1H), 4.48 (s, 2H), 4.60 (t, 2H), 5.13 (d, 1H), 6.81 (d, 1H), 6.95 (d, 2H), 7.06-7.15 (m, 2H), 7.16-7.23 (m, 2H), 7.33 (d, 2H), 7.70-7.76 (m, 1H), 7.79 (s, 1H), 8.34 (t, 1H), 12.55 (bs, 1H). M/z: 565.20 (M+1) and 563.22 (M−1).

{4-[(2R,3R)-3-{[2-(2,3-dihydro-1-benzofuran-5-yl)-2-oxoethyl]thio}-1-(4-fluorophenyl)-4-oxoazetidin-2-yl]phenoxy}acetic acid To a stirred solution of tert-butyl (4-{(2R,3R)-1-(4-fluorophenyl)-3-[(3-nitropyridin-2-yl)dithio]-4-oxoazetidin-2-yl}phenoxy)acetate (50.0 mg, 0.090 mmol) in acetone (6 ml) and water (0.8 ml) was added triphenylphosphine (33.3 mg, 0.013 mmol). The reaction mixture was stirred for 15 minutes. The solvent was removed under reduced pressure and the crude thiol was dissolved in DCM (12 ml). $Et_3N$, (30 pd, 0.22 mmol) was added. After 5 minutes, 2-chloro-1-(2,3-dihydro-1-benzofuran-5-yl)ethanone (37.2 mg, 0.19 mmol) was added and the reaction mixture was stirred overnight. Additional triphenylphosphine (11.6 mg, 0.04 mmol), $Et_3N$ (10 μl, 1, 0.07 mmol) and 2-chloro-1-(2,3-dihydro-1-benzofuran-5-yl)ethanone (7.2 mg, 0.04 mmol) were added and the reaction mixture was stirred for 1 hour. The formation of the tert-butyl ester of the title compound was confirmed. M/z: 564.24 (M+1) and 562.21 (MA). To the DCM solution of the previous reaction was added TFA (6 ml) and the mixture was stirred for 1 hour. The solvent was removed under reduced pressure and the residue was purified with preparative HPLC on a C8 column. A gradient from 20 to 70% ACN in 0.1M $NH_4OAc$ buffer was used as eluent. The pure fractions were collected and the MeCN was removed under reduced pressure. The remaining water solution was diluted with additional water and EtOAc. The water phase was acidified with $KHSO_4$ (2M) to pH 2. The phases were separated and the organic phase was passed through a phase separator and concentrated. The oily residue was dissolved in MeCN and water. After lyophilisation, the title compound was obtained. H-NMR (400 MHz, DMSO-$d_6$): 3.17 (t, 2H), 4.23 (ABq, 2H), 4.28 (d, 1H), 4.52 (b, 2H), 4.59 (t, 2H), 5.11 (d, 1H), 6.78-6.88 (m, 3H), 7.09-7.15 (m, 2H) 7.16-7.22 (m, 2H), 7.30 (d, 2H), 7.71-7.76 (m, 1H), 7.79 (s, 1H). M/z: 508.13 (M+1) and 506.22 (M−1).

(4S)-3-{[(4-Methoxybenzyl)thio]acetyl}-4-phenyl-1,3-oxazolidin-2-one

[(4-Methoxybenzyl)thio]acetic acid (1.3 g, 6.1 mmol) was dissolved in dry $CH_2Cl_2$ (40 ml) and given 0° C. N,N'-Dicyclohexylcarbodiimide (DCC, 6.1 g, 6.1 mmol) and 4-(dimethylamino)pyridine (DMAP, 1.6 g, 12.9 mmol) were added and the mixture was stirred for 30 minutes. (S)-(+)-4-Phenyl-2-oxazolidinone (1.0 g, 6.1 mol) was added and the mixture was stirred at room temperature for 24 hours. The mixture was filtrated, concentrated under reduced pressure and purified by flash-chromatography (Hex:EtOAc 8:2 then 1:1). This afforded the title compound as a white solid.

$^1$H-NMR ($CDCl_3$, 200 MHz): δ 3.46-3.59 (m, 3H), 3.74-3.76 (m, 4H), 4.23-4.28 (m, 1H), 4.68 (t, J=8.8 Hz, 1H), 5.38-5.42 (m, 1H), 6.78 (d, J=8.6 Hz, 2H), 7.14 (d, J=8.6 Hz, 2H), 7.32-7.40 (m, 5H).

tert-Butyl (4-{(1R)-1-[(4-fluorophenyl)amino]-2-[(4-methoxybenzyl)thio]-3-oxo-3-[(4S)-2-oxo-4-phenyl-1,3-oxazolidin-3-yl]propyl}phenoxy)acetate $TiCl_4$ (1M in $CH_2Cl_2$, 12.6 mL, 12.6 mmol) was added to a solution of tetraisopropyl orthotitanate (1.24 mL, 4.2 mmol) in $CH_2Cl_2$ (80 mL) held at 0° C. under inert atmosphere. The mixture was stirred for 15 minutes, then (4S)-3-{[(4-methoxybenzyl)thio]acetyl}-4-phenyl-1,3-oxazolidin-2-one (6.0 g, 16.8 mmol) in dry $CH_2Cl_2$ (60 mL) was added dropwise over 30 minutes and the mixture was stirred for ten minutes. Then tert-butyl (4-{(E)-[(4-fluorophenyl)imino]methyl}phenoxy)acetate (11.1 g, 33.6 mmol) in dry $CH_2Cl_2$ (60 mL) was added dropwise over 30 minutes, the mixture was given −40° C. and stirred for 20 minutes. Ethyl diisopropyl amine (5.8 mL, 33.6 mmol) in 20 mL $CH_2Cl_2$ was added dropwise over 20 minutes and the mixture was stirred at −40° C. for 90 minutes. The mixture was then given −78° C., added isopropanol (50 mL) and slowly given room temperature over two hours. $H_2O$ (100 mL) was added and the mixture was stirred for 20 minutes at room temperature and then extracted twice with diethyl ether. The combined organic layer was washed with water, dried ($MgSO_4$) and concentrated under reduced pressure. The crude product was dissolved in methanol and a precipitate formed. Filtration and drying the title compound.

$^1$H-NMR ($CDCl_3$, 200 MHz): δ 1.5 (s, 9H), 3.65 (s, 1H), 3.8 (s, 3H), 4.1 (m, 1H), 4.4-4.6 (m, 4H), 5.0-5.2 (m, 2H), 5.4 (m, 1H), 6.4-6.6 (m, 2H), 6.7-7-4 (m, 15H).

tert-Butyl (4-{(2R,3R)-1-(4-fluorophenyl)-3-[(4-methoxybenzyl)thio]-4-oxoazetidin-2-yl}phenoxy) acetate tert-Butyl (4-{(1R)-1-[(4-fluorophenyl)amino]-2-[(4-methoxybenzyl)thio]-3-oxo-3-[(4S)-2-oxo-4-phenyl-1,3-oxazolidin-3-yl]propyl}phenoxy)acetate (9.3 g, 13.5 mmol) was dissolved in dry toluene (500 mL) and heated to 90° C. under inert atmosphere. N,O-Bis(trimethylsilyl)acetamide (BSA, 9.9 mL, 40.6 mmol) was added and the mixture was stirred at 90° C. for one hour. The mixture was then given 45° C. and tetrabutylammonium fluoride (TBAF, 1 g) was added. The mixture was stirred at 45° C. for 24 hours. After cooling, the mixture was concentrated under reduced pressure and purified by flash-chromatography (Hex:EtOAc 6:1 then 5:1 then 4:1). This afforded the title compound.

$^1$H-NMR. ($CDCl_3$, 200 MHz): δ 1.5 (s, 9H), 3.7 (s, 3H), 3.9 (m, 3H), 4.5 (m, 3H), 6.7 (d, 2H), 6.8-7.0 (m, 4H), 7.0-7.2 (m, 6H).

tert-Butyl (4-{(2R,3R)-1-(4-fluorophenyl)-3-[(3-nitropyridin-2-yl)dithio]-4-oxoazetidin-2-yl}phenoxy)acetate tert-Butyl (4-{(2R,3R)-1-(4-fluorophenyl)-3-[4-methoxybenzyl)thio]-4-oxoazetidin-2-yl}phenoxy)acetate (2.54 g, 4.86 mmol) was dissolved in $CH_2Cl_2$ (60 mL) and given 0° C. under inert atmosphere. 3-nitro-2-pyridinesulfenyl chloride (1.11 g, 5.82 mmol) was added and the mixture was stirred for two hours at 0° C., the one hour at room temperature. Concentration under reduced pressure and purification by flash-chromatography (Hex:EtOAc 2:1) afforded the title compound.

$^1$H-NMR ($CDCl_3$, 200 MHz): δ 1.6 (s. 9H), 4.3 (d, 1H), 4.5 (s, 2H), 5.2 (d, 1H), 6.8-7.0 (m, 4H), 7.1-7.3 (m, 4H), 7.4 (m, 1H) 8.5 (d, 1H), 8.9 (d, 1H).

Glycyl-3-cyclohexyl-D-alanine

N-(tert-butoxycarbonyl)glycine (2.0 g, 11.4 mmol) and DIPEA (4.0 g, 31 mmol) were dissolved in methylene chloride (25 ml). TBTU (4.1 g, 12.8 mmol) was added and the mixture was stirred for 15 min at room temperature. 3-cyclohexyl-D-alanine (2.1 g, 12.2 mmol) was added and the reaction mixture was stirred over night at room temperature. The reaction mixture was transferred to a separation funnel and was then extracted with a water/acetic acid solution (100 ml 5% acetic acid). The organic layer was separated and evaporated under reduced pressure. The residue was dissolved in formic acid (20 ml) and the mixture was stirred over night at 40° C. The formic acid was removed under reduced pressure. The residue was washed with water (50 ml) and then stirred in aceton (25 ml) for 1 h at room temperature. The solid material was filtered off and washed with aceton (20 ml). The title compound was obtained.

$^1$H-NMR, 300 MHz, CD3COOD): 0.8-1.9 (m, 1H), 3.9-4.1 (m, 2H), 4.55-4.65 (m, 1H)

tert-butyl (4-{(E)-[(4-fluorophenyl)imino] methyl}phenoxy)acetate tert-Butyl (4-formylphenoxy)acetate (93.7 g, 0.40 mol) was dissolved in dry toluene (200 mL), added 4-fluoroaniline (38.1 mL, 0.40 mol) and p-toluene sulfonic acid (cat, ±1 g). The mixture was refluxed in a Dean-Stark apparatus for 2 hours, cooled at an icebath and a precipitate was formed. The precipitate was filtered, washed with cold heptane and dried to afford the title compound.

$^{1}$H-NMR ($CDCl_3$, 200 MHz): δ 1.6 (s, 9H), 4.8 (s, 2H), 7.0-7.4 (m, 6H), 7.9 (d, 2H), 8.4 (s, 1H).

{4-[(2R,3R)-3-{[2-(2,3-dihydro-1H-inden-5-yl)-2-oxoethyl]thio}-1-(4-fluorophenyl)-4-oxoazetidin-2-yl]phenoxy}acetic acid To a solution of tert-butyl (4-{(2R,3R)-1-(4-fluorophenyl)-3-[(3-nitropyridin-2-yl)dithio]-4-oxoazetidin-2-yl}phenoxy)acetate (0.100 g, 0.179 mmol) in acetone (2 ml) and water (0.5 ml) was added triphenylphosphine (0.047 g, 0.179 mmol). After 30 minutes, the mixture was concentrated. To the residue was added dichloromethane (3 ml) followed by the addition of triethylamine (0.073 g, 0.717 mmol) and 2-bromo-1-(2,3-dihydro-1H-inden-5-yl)ethanone (0.107 g, 0.448 mmol). After 30 minutes, full conversion of the thiol had been achieved. The mixture was concentrated and to the residue was added formic acid (2 g) and trifluoroacetic acid (0.2 g). The mixture was allowed to stir at room temperature for 3 h. The crude product was purified through preparative HPLC using an eluent of 10-50% $CH_3CN$ in 0.1M $NH_4OAc$ buffer. Freeze drying of pure fractions afforded the desired compound. $^{1}$H NMR [$(CD_3)_2SO$), 400 MHz] δ1.96-2.04 (m, 2H), 2.83-2.89 (m, 4H), 4.23-4.34 (m, 5H), 5.09 (d, 1H), 6.76-7.74 (m, 11H).

[4-((2R,3R)-1-(4-fluorophenyl)-4-oxo-3-{[2-oxo-2-(5,6,7,8-tetrahydronaphthalen-2-yl)ethyl]thio}azetidin-2-yl)phenoxy]acetic acid The titled compound above was prepared using the same procedure as that used for the synthesis of {4-[(2R,3R)-3-{[2-(2,3-dihydro-1H-inden-5-yl)-2-oxoethyl]thio}-1-(4-fluorophenyl)-4-oxoazetidin-2-yl]phenoxy}acetic acid but using 2-bromo-1-(5,6,7,8-tetrahydronaphthalen-2-yl)ethanone instead of 2-bromo-1-(2,3-dihydro-1H-inden-5-yl)ethanone. $^{1}$H NMR [$(CD_3)_2SO$), 400 MHz]δ 1.66-1.75 (m, 4H), 2.66-2.77 (m, 4H), 4.22-4.31 (m, 3H), 4.62 (s, 2H), 5.11 (d, 1H), 6.86-7.61 (m, 11H).

[4-((2R,3R)-1-(4-fluorophenyl)-3-{[(2R or S)-2-hydroxy-2-(5,6,7,8-tetrahydronaphthalen-2-yl)ethyl]thio}-4-oxoazetidin-2-yl)phenoxy]acetic acid To a solution of [4-((2R,3R)-1-(4-fluorophenyl)-4-oxo-3-{[2-oxo-2-(5,6,7,8-tetrahydronaphthalen-2-yl)ethyl]thio}azetidin-2-yl)phenoxy]acetic acid (0.105 g, 0.20 mmol) in MeOH (3 ml) was added $NaBH_4$ (0.015 g, 0.40 mmol). After 5 minutes, the resulting two diastereomeric alcohols (50:50 mixture) were separated through preparative HPLC using a C-8 column and $CH_3CN$ in 0.1M $NH_4OAc$ buffer (0-40%) as eluent. Freeze drying of pure fractions afforded the desired pure diastereomer (the first eluting one. $^{1}$H NMR [$(CD_3)_2SO$), 400 MHz] δ 1.62-1.70 (M, 4H), 2.56-2.67 (m, 4H), 2.80-2.89 (m, 2H), 4.22 (d, 1H), 4.53-4.59 (d, 1H), 4.62 (s, 2H), 4.98 (d, 1H), 5.43 (d, 1H), 6.88-7.32 (m, 11H).

N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycine To a stirred solution of {4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetic acid (317.0 mg, 0.51 mmol) and methyl glycinate hydrochloride (77.5 mg, 0.62 mmol) in DCM (3 ml, dry) was added N-methylmorpholine (168 μl, 1.52 mmol). The reaction mixture was stirred for five minutes. TBTU (194 mg, 0.604 mmol) was added and the reaction mixture was stirred for 2 hours. The formation of the methylester of the title compound was confirmed; M/z: 693 (M−1). The solvent was removed under reduced pressure. The residue was suspended in MeCN (6 ml). Triethylamine (750 μl, 5.39 mmol), water (0.5 ml) and LiCl (478.0 mg, 11.28 mmol) were added. The reaction mixture was stirred over the weekend. Water was added and the resulting solution was purified with preparative HPLC on a C8 column, UV 235/285 nm. A gradient from 20 to 100% MeCN in 0.1 M $NH_4OAc$ buffer was used as eluent. The pure fractions were collected and the MeCN was removed under reduced pressure. The remaining water solution was acidified to pH 3 with $KHSO_4$ (2M) and extracted from DCM. The organic phase was passed through a phase separator and the solvent was removed under reduced pressure. The residue was dissolved in MeCN and water. After lyophilisation, the title compound was obtained. H-NMR (400 MHz, DMSO-$d_6$): −0.18 (s, 3H), −0.04 (s, 3H), 0.78 (s, 9H), 2.79-2.87 (m, 1H), 2.90-2.99 (m, 1H) 3.11 (t, 2H), 3.78 (d, 2H), 4.26 (d, 1H), 4.49 (t, 2H), 4.52 (s, 2H), 4.81 (t, 1H), 5.07 (d, 1H), 6.68 (d, 1H), 6.97-7.07 (m, 3H), 7.12-7.20 (m, 3H), 7.22-7.28 (m, 2H), 7.38 (d, 2H), 8.33 (bt, 1H). M/z: 679.36 (M−1).

N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-3-methyl-D-valine To a stirred solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycine (20.4 mg, 0.030 mmol) and N-methylmorpholine (10 μl, 0.090 mmol) in DCM (2 ml, dry) was added TBTU (11.6 mg, 0.036 mmol). The reaction mixture was stirred at 30° C. for 1.5 hours. 3-methyl-D-valine (5.8 mg, 0.044 mmol) was added and the reaction mixture was stirred overnight. Water (1 ml) was added to the reaction mixture. The solvent was removed under reduced pressure and the residue was purified with preparative HPLC on a C8 column, UV 235/285 nm. A gradient from 20 to 100% ACN in 0.1M $NH_4OAc$ buffer was used as eluent. The pure fractions were collected and most of the MeCN was removed under reduced pressure. The residue was lyophilised to give the title compound as a white solid (8.5 mg, 36%). M/z: 793.49 (M−1).

N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-D-valine To a stirred solution of {4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetic acid (23.0 mg, 0.037 mmol) and N-methylmorpholine (12 μl, 0.111 mmol) in DMF (1 ml, dry) was added TBTU (16.6 mg, 0.052 mmol). The reaction mixture was stirred for 45 minutes at 30° C. Glycyl-D-valine hydrochloride (10.2 mg, 0.052 mmol) was added and the reaction mixture was stirred for 3.5 hours. The solution was purified with preparative HPLC on a C8 column, UV 235/285 nm. A gradient from 10 to 95% MeCN in 0.1M $NH_4OAc$ buffer was used as eluent. The pure fractions were collected and most of the MeCN was removed under reduced pressure. After lyophilisation, the title compound was obtained. M/z: 779.47 (M−1).

N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-4-cyano-D-phenylalanine To a stirred solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycine (20.8 mg, 0.031 mmol) and N-methylmorpholine (10 μl, 0.092 mmol) in DMF (1 ml, dry) at 30° C. was added TBTU (13.8 mg, 0.043 mmol). The reaction mixture was stirred at 30° C. 1 hour. 4-cyano-D-phenylalanine hydrochloride (9.6 mg, 0.042 mmol) was added and the reaction mixture was stirred overnight. Water (1 ml) was added to the reaction mixture. The solution was purified with preparative HPLC on a C8 column, UV 235/285 nm. A gradient from 20 to 100% MeCN in a 0.1M $NH_4OAc$ buffer was used as eluent. Most of the MeCN was removed under reduced. The residue was lyophilised to give the title compound. M/z: 851 (M−1).

N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-$N^6$,$N^6$-dimethyl-L-lysine To a stirred solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycine (21 mg, 0.031 mmol) and N-methylmorpholine (10 μl, 0.093 mmol) in DMF (1 ml, dry) was added TBTU (14 mg, 0.044 mmol). The reaction mixture was stirred at 30° C. for 45 minutes. $N^6$,$N^6$-dimethyl-L-lysine hydrochloride (10.0 mg, 0.047 mmol) was added and the reaction mixture was stirred for 2 hours. Water (1 ml) was added to the reaction mixture. The solution was purified with preparative HPLC on a C8 column, UV 235/285 nm. A gradient from 10 to 100% MeCN in 0.1 M $NH_4OAc$ buffer was used as eluent. Most of the MeCN was removed under reduced pressure and the residue was diluted with water. After lyophilisation, the title compound was obtained. M/z: 836 (M−1).

N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-3-methyl-D-isovaline To a stirred solution of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-3-methyl-D-isovaline (20.8 mg, 0.031 mmol) in DMF (1 ml, dry) was added N-methylmorpholine (10 μl, 0.088 mmol). The reaction mixture was stirred at 30° C. for five minutes. TBTU (14.2 mg, 0.044 mmol) was added and the reaction mixture was stirred for 1 hour. 3-methyl-D-isovaline (6.0 mg, 0.046 mmol) was added and the reaction mixture was stirred at 30° C. for 2 hours. Water (1 ml) was added to the reaction mixture. The solution was purified with preparative HPLC on a C8 column, UV 235/285 nm. A gradient from 10 to 100% MeCN in 0.1M $NH_4OAc$ buffer was used as eluent. The pure fractions were collected and most of the MeCN was removed under reduced pressure. The residue was lyophilised to give the title compound. M/z: 793 (M−1).

N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycylglycine To a stirred suspension of N-({4-[(2R,3R)-3-{[(2R or S)-2-{[tert-butyl(dimethyl)silyl]oxy}-2-(2,3-dihydro-1-benzofuran-5-yl)ethyl]thio}-1-(4-fluorophenyl)-4-oxoazetidin-2-yl]phenoxy}acetyl)glycyl-3-methyl-D-isovaline (51.6 mg, 0.082 mmol) and methyl glycinate hydrochloride (54.2 mg, 0.43 mmol) in DCM were added N-methylmorpholine (119 μl, 1.07 mmol) and TBTU (139 mg, 0.43 mmol). The reaction mixture was stirred overnight. Water (0.5 ml) was added and the solvent was removed under reduced pressure. The residue as dissolved in MeCN (3 ml). Triethylamine (500μ, 3.59 mmol), water (20 μl, 1.11 mmol) and LiCl (330 mg, 7.78 mmol) were added and the reaction mixture was stirred overnight. Additional triethylamine (50 μl, 0.36 mmol) was added and the reaction mixture was stirred overnight. The reaction mixture was diluted with water and MeCN and the solution was purified with preparative HPLC on a C8 column. A gradient from 20 to 92% MeCN in 0.1 M $NH_4OAc$ was used as eluent. The MeCN was removed under reduced pressure. The fractions containing the desired product were partitioned between water and DCM. The water phase was acidified to pH ca 3 with $KHSO_4$ (2M). The phases were separated and the organic phase was concentrated. The residue was diluted with MeCN and water and lyophilised to give the title compound. H-NMR (400 MHz, DMSO-$d_6$): −0.18 (s, 3H), −0.05 (s, 3H), 0.77 (s, 9H), 2.80-2.96 (dm, 2H), 3.11 (t, 2H), 3.68 (b, 2H), 3.78 (d, 2H), 4.26 (d, 1H), 4.46-4.51 (m, 2H), 4.52 (s, 2H), 4.79-4.83 (m, 1H), 5.06 (d, 1H), 6.67 (d, 1H), 6.97-7.05 (m, 3H), 7.12-7.19 (m, 3H), 7.21-7.27 (m, 2H), 7.37 (d, 2H), 8.09 (b, 1H), 8.31 (t, 1H). M/z: 736.39 (M−1).

1-(2,3-Dihydro-benzofuran-6-yl)-ethanone

A solution of bromo(2,3-dihydro-1-benzofuran-6-yl)magnesium (prepared from 6-bromo-2,3-dihydro-benzofuran (2.50 g, 12.56 mmol) and Mg (0.336 g, 13.8 mmol)) in THF (10 mL) was dropwise added to a solution of acetic anhydride (2.40 mL, 25.4 mmol) in Et2O (10 mL) held at −78° C. The reaction mixture was stirred at −78° C. for 1 h before the temperature was allowed to reach −10° C. over a period of 1 h. The reaction mixture was quenched by the addition of NH4Cl (aq, saturated, 20 mL) and the resulting mixture was extracted twice with Et2O (2×10 mL). The organic extracts were pooled, washed with NaOH (aq, 5%, 10 mL) and brine (10 mL), dried over MgSO4 and concentrated under reduced pressure. The residue was purified by preparative HPLC using a gradient of 20-50% MeCN in a 0.1M ammonium acetate buffer as eluent. Freeze-drying of the pure fractions gave the desired product.

$^1$H-NMR (CDCl3, 400 MHz): δ 2.5 (s, 3H), 3.2 (t, 2H), 4.6 (t, 2H), 7.5-7.7 (m, 3H).

2-Bromo-1-(2,3-dihydro-benzofuran-6-yl)-ethanone $Br_2$ (0.36 ml, 7.01 mmol) was added dropwise to a stirring solution of 1-(2,3-dihydro-benzofuran-6-yl)-ethanone (1.13 g, 6.97 mmol) in MeOH (20 mL) held at 0° C. The reaction mixture was slowly allowed to reach room temperature. After 3 h, the reaction was quenched by the addition of NaHCO3

(aq, saturated)(until pH=8). Most of the methanol was removed under reduced pressure and the residue was extracted twice with EtOAc (2×20 mL). The organic extracts were pooled, washed with brine (10 mL), dried over $MgSO_4$ and concentrated under reduced pressure. The residue was purified by preparative HPLC using a gradient of 40-70% MeCN in a 0.1M ammonium acetate buffer as eluent. The fractions containing the desired product were pooled and most of the MeCN was removed under reduced pressure. The residue was extracted with EtOAc (2×20 mL) and the combined organic layers was washed with brine, dried over $MgSO_4$ and concentrated. The obtained was finely washed MeOH to give the title compound.

$^1$H-NMR ($CDCl_3$, 400 MHz): δ 3.25 (t, 2H), 4.39 (s, 2H), 4.61 (t, 2H), 7.24-7.36 (m, 2H), 7.45-7.52 (m, 1H).

{4-[(2R,3R)-3-[2-(2,3-Dihydro-benzofuran-6-yl)-2-oxo-ethylsulfanyl]-1-(4-fluoro-phenyl)-4-oxo-azetidin-2-yl]-phenoxy}-acetic acid tert-butyl ester Triphenyl phosphine (50 mg, 0.191 mmol) was added to a solution of {4-[(2R,3R)-1-(4-fluoro-phenyl)-3-(3-nitro-pyridin-2-yldisulfanyl)-4-oxo-azetidin-2-yl]-phenoxy}-acetic acid tert-butyl ester (100 mg, 0.179 mmol) in acetone/water (3 mL/0.5 mL) at room temperature. The mixture was stirred for 15 min. The solvent was removed under reduced pressure and the residue was dissolved in DCM (3 mL). $Et_3N$ (75 μL, 0.534 mmol) and 2-bromo-1-(2,3-dihydro-benzofuran-6-yl)-ethanone (91 mg, 0.377 mmol) were added and the solution was stirred at room temperature for 16 h. The solvent was removed under reduced pressure and the residue was purified by preparative HPLC using a gradient of 40-80% MeCN in a 0.1M ammonium acetate buffer as eluent. The pure fractions were pooled and most of the MeCN was removed under reduced pressure. The residue was extracted with EtOAc and the organic layer was washed with brine, dried over MgSO4 and concentrated. The title compound was obtained.

$^1$H-NMR (CDCl3, 400 MHz): δ 1.4 (s, 9H), 3.2 (t, 2H), 4.0 (d, 1H), 4.1 (s, 2H), 4.4 (s, 2H), 4.6 (t, 2H), 4.8 (d, 1H), 6.7-6.9 (m, 4H), 7.1-7.3 (m, 6H), 7.3-7.4 (m, 1H).

{4-[(2R,3R)-3-[2-(2,3-Dihydro-benzofuran-6-yl)-2-oxo-ethylsulfanyl]-1-(4-fluoro-phenyl)-4-oxo-azetidin-2-yl]-phenoxy}-acetic acid {4-[(2R,3R)-3-[2-(2,3-Dihydro-benzofuran-6-yl)-2-oxo-ethylsulfanyl]1-(4-fluoro-phenyl)-4-oxo-azetidin-2-yl]-phenoxy}-acetic acid tert-butyl ester (77 mg, 0.137 mmol) was dissolved in formic acid (3 mL) and the solution was stirred for 1 h at room temperature. The solvent was removed under reduced pressure and the residue was dissolved in DCM. The solution was washed with water and then concentrated under reduced pressure. The residue was freeze-dried from MeCN/water to give the title compound.

$^1$H-NMR (DMSO, 500 MHz): δ 3.23 (t, 2H), 4.24-4.36 (m, 3H), 4.57 (t, 2H), 4.65 (s, 2H), 5.15 (d, 1H), 6.86-6.93 (m, 2H), 7.11-7.27 (m, 5H), 7.30-7.37 (m, 3H), 7.42-7.47 (m, 1H).

It will be appreciated by those skilled in the art that the examples may be modified within the realms of the invention, why the invention is not limited to particular embodiments.

Absorption

Absorption of the compounds of formula (I) was tested in a Caco-2 cells model (Gastroenterology 1989, 96, 736):

| Compound (I) | Caco value ($10^{-6}$ cm/sec) |
|---|---|
| Example 1 | 0.05 |

The invention claimed is:

1. A compound of formula (I):

(I)

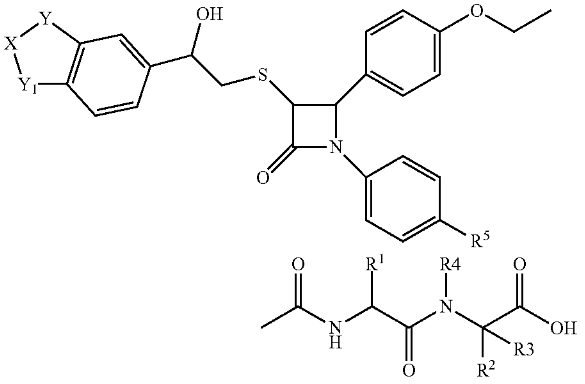

wherein:

X is —$CH_2$—, —$CH_2CH_2$—, or —$CH_2CH_2CH_2$—;

Y is —$CH_2$— or O;

$Y_1$ is —$CH_2$— or O;

wherein at least one of Y and $Y_1$ is —$CH_2$—;

$R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N—($C_{1-6}$alkyl)amino, N,N—($C_{1-6}$alkyl)$_2$ amino, $C_1$-$C_6$alkylcarbonylamino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl and $C_{1-6}$alkoxy;

$R^2$ and $R^3$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, ($C_1$-$C_4$ alkyl)$_3$Si, N—($C_{1-6}$alkyl)amino, N,N—($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, cyano, $C_{1-6}$alkyl and $C_{1-6}$alkoxy;

$R^4$ is hydrogen, $C_{1-6}$ alkyl, or aryl$C_{1-6}$ alkyl;

wherein $R^3$ and $R^2$ may form a ring with 3-7 carbon atoms and wherein $R^4$ and $R^2$ may form a ring with 2-6 carbon atoms; and $R^5$ is selected from halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

or a pharmaceutically acceptable salt, or a prodrug thereof.

2. A compound of formula (I2):

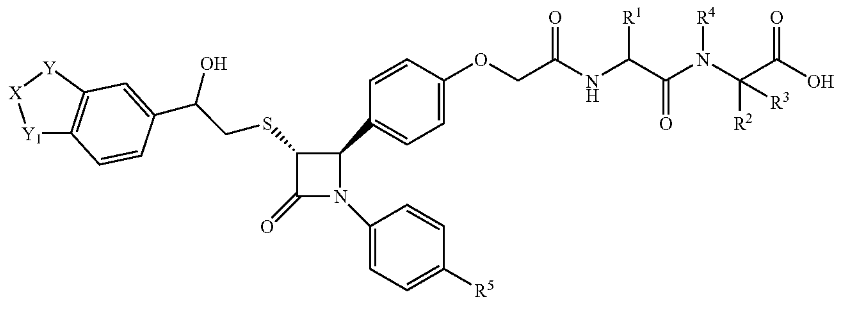

(I2)

wherein:

X is —$CH_2$—, —$CH_2CH_2$—, or —$CH_2CH_2CH_2$—;

Y is —$CH_2$— or O;

$Y_1$ is —$CH_2$— or O;

wherein at least one of Y and $Y_1$ is —$CH_2$—;

$R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N—($C_{1-6}$alkyl)amino, N,N—($C_{1-6}$alkyl)$_2$ amino, $C_1$-$C_6$alkylcarbonylamino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl and $C_{1-6}$alkoxy;

$R^2$ and $R^3$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl$C_{1-6}$alkoxy, ($C_1$-$C_4$ alkyl)$_3$Si, N—($C_{1-6}$alkyl)amino, N,N—($C_{1-6}$alkyl)$_2$amino, $C_{1-6}$alkylS(O)$_a$, $C_{3-6}$cycloalkyl, aryl or aryl $C_{1-6}$alkylS(O)$_a$, wherein a is 0-2; and wherein any aryl group may be optionally substituted by one or two substituents selected from halo, hydroxy, cyano, $C_{1-6}$alkyl and $C_{1-6}$alkoxy;

$R^4$ is hydrogen, $C_{1-6}$ alkyl, or aryl$C_{1-6}$ alkyl;

wherein $R^3$ and $R^2$ may form a ring with 3-7 carbon atoms and wherein $R^4$ and $R^2$ may form a ring with 2-6 carbon atoms; and $R^5$ is selected from halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$ alkyl)sulphamoyl and N,N—($C_{1-6}$alkyl)$_2$sulphamoyl;

or a pharmaceutically acceptable salt, or a prodrug thereof.

3. A compound according to claim 1, wherein X is —$CH_2$—.

4. A compound according to claim 1, wherein X is —$CH_2CH_2$—.

5. A compound according to claim 1, wherein X is —$CH_2CH_2CH_2$—.

6. A compound according to claim 1, wherein, $R^1$ is hydrogen;

$R^2$ and $R^3$ are, independently, hydrogen or a branched or unbranched $C_{1-6}$alkyl; wherein said $C_{1-6}$alkyl is substituted by $C_{3-6}$cycloalkyl, aryl or amino; and $R^4$ is hydrogen.

7. A compound according to claim 1 wherein, $R^1$ is hydrogen;

$R^2$ and $R^3$ are, independently, hydrogen or a branched or unbranched $C_{1-6}$alkyl; wherein said $C_{1-6}$alkyl is substituted by $C_{3-6}$cycloalkyl; and $R^4$ is hydrogen.

8. A compound according to claim 7, wherein, $R^2$ is hydrogen and $R^3$ is tert-butyl.

9. A compound according to claim 7, wherein, $R^2$ is hydrogen and $R^3$ is methyl; wherein said methyl is substituted by cyclohexyl.

10. A compound according to claim 1, wherein, $R^5$ is chlorine or fluorine.

11. One or more compounds selected from:

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-D-lysine;

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-b,b-dimethyl-D-phenylalanine; and N-({4-[(2R,3R)-3-{[(2R or S)-2-(2,3-Dihydro-1-benzofuran-5-yl)-2-hydroxyethyl]thio}-1-(4-fluorophenyl)-4-oxoazetidin-2-yl]phenoxy}acetyl)glycyl-3-cyclohexyl-D-alanine ammoniate;

N-({4-[(2R,3R)-3-{[(2R or S)-2-(2,3-dihydro-1-benzofuran-5-yl)-2-hydroxyethyl]thio}-1-(4-fluorophenyl)-4-oxoazetidin-2-yl]phenoxy}acetyl)glycyl-3-methyl-D-valine;

N-({4-[(2R,3R)-3-{[(2R or S)-2-(2,3-dihydro-1-benzofuran-5-yl)-2-hydroxyethyl]thio}-1-(4-fluorophenyl)-4-oxoazetidin-2-yl]phenoxy}acetyl)glycyl-D-valine;

N-({4-[(2R,3R)-3-{[(2R or S)-2-(2,3-dihydro-1-benzofuran-5-yl)-2-hydroxyethyl]thio}-1-(4-fluorophenyl)-4-oxoazetidin-2-yl]phenoxy}acetyl)glycyl-4-cyano-D-phenylalanine;

N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycyl-$N^6$,$N^6$-dimethyl-L-lysine;

N-({4-[(2R,3R)-3-{[(2R or S)-2-(2,3-dihydro-1-benzofuran-5-yl)-2-hydroxyethyl]thio}-1-(4-fluorophenyl)-4-oxoazetidin-2-yl]phenoxy}acetyl)glycyl-3-methyl-D-isovaline; and N-({4-[(2R,3R)-3-{[2-(2,3-dihydro-1-benzofuran-5-yl)-2-hydroxyethyl]thio}-1-(4-fluorophenyl)-4-oxoazetidin-2-yl]phenoxy}acetyl)glycylglycine.

12. A compound of the (XVI):

(XVI)

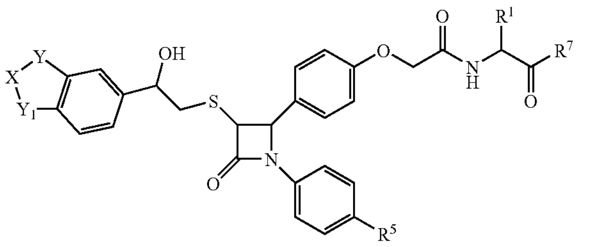

wherein:

X is —$CH_2$—, —$CH_2CH_2$—, or —$CH_2CH_2CH_2$—;

Y is —$CH_2$— or O;

$Y_1$ is —$CH_2$— or O;

wherein at least one of Y and $Y_1$ is —$CH_2$—;

$R^1$ is hydrogen, $C_{1-6}$ alkyl, $C_{3-6}$cycloalkyl or aryl;

$R^5$ is selected from halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$ alkyl)sulphamoyl and N,N—($C_{1-6}$alkyl)$_2$sulphamoyl; and $R^7$ is an hydroxy group or a $C_{1-4}$alkoxy group.

13. A method of treating or preventing hyperlipidemic conditions comprising the administration of an effective amount of a compound according to claim 1 to a mammal in need thereof.

14. A method of treating or preventing atherosclerosis comprising the administration of an effective amount of a compound according to claim 1 to a mammal in need thereof.

15. A pharmaceutical formulation comprising a compound according to claim 1 in admixture with a pharmaceutically acceptable adjuvant, diluent and/or carrier.

16. A combination of a compound according to formula (I) or (I2)

(I)

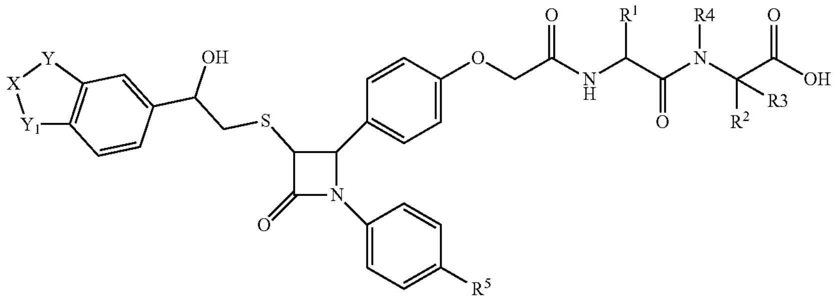

(I2)

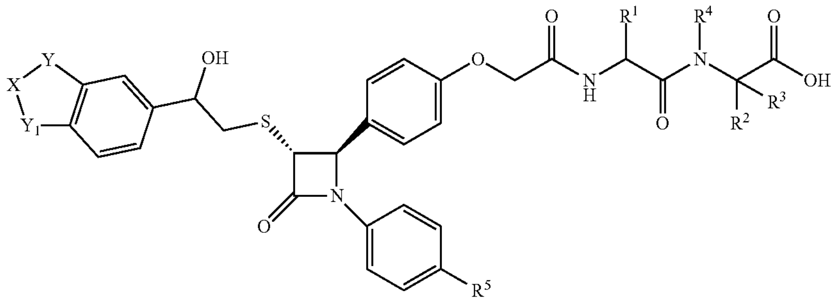

wherein:

X is $-CH_2-$, $-CH_2CH_2-$, or $-CH_2CH_2CH_2-$;

Y is $-CH_2-$ or O;

$Y_1$ is $-CH_2-$ or O;

wherein at least one of Y and $Y_1$ is $-CH_2-$;

$(O)_a$ wherein a is 0 to 2, $C_{1-6}$alkoxycarbonyl, N—($C_{1-6}$ alkyl)sulphamoyl and N,N—($C_{1-6}$alkyl)$_2$sulphamoyl;

with a PPAR alpha and/or gamma agonist.

17. A combination of a compound according to formula (I) or (I2)

(I)

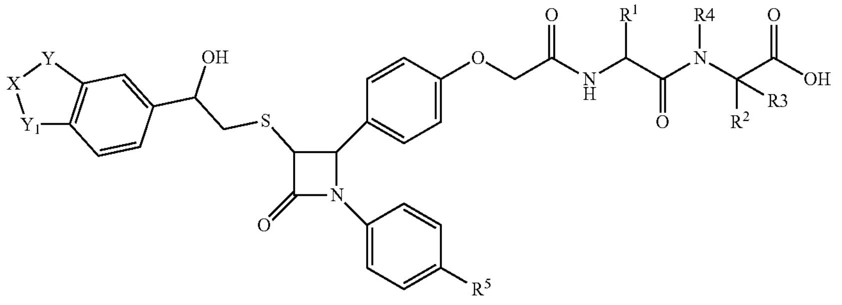

(I2)

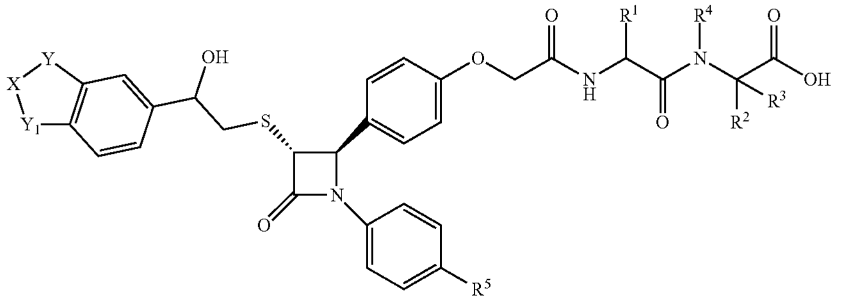

$R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N—($C_{1-6}$alkyl)amino, N,N—($C_{1-6}$alkyl)$_2$ amino, $C_1$-$C_6$alkylcarbonylamino, $C_{1-6}$alkylS$(O)_a$ wherein a is 0-2, $C_{3-6}$cycloalkyl or aryl; and wherein any aryl group may be optionally substituted by one or two substituents selected from halo, hydroxy, $C_{1-6}$alkyl and $C_{1-6}$alkoxy;

$R^2$ and $R^3$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl$C_{1-6}$alkoxy, ($C_1$-$C_4$ alkyl)$_3$Si, N—($C_{1-6}$alkyl)amino, N,N—($C_{1-6}$alkyl)$_2$amino, $C_{1-6}$alkylS$(O)_a$, $C_{3-6}$cycloalkyl, aryl or aryl$C_{1-6}$alkylS$(O)_a$, wherein a is 0-2; and wherein any aryl group may be optionally substituted by one or two substituents selected from halo, hydroxy, cyano, $C_{1-6}$alkyl, and $C_{1-6}$alkoxy;

$R^4$ is hydrogen, $C_{1-6}$ alkyl, or aryl$C_{1-6}$ alkyl;

wherein $R^3$ and $R^2$ may form a ring with 3-7 carbon atoms and wherein $R^4$ and $R^2$ may form a ring with 2-6 carbon atoms; and $R^5$ is selected from halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl) carbamoyl, N,N—($C_{1-6}$alkyl)$_2$carbamoyl, $C_{1-6}$alkylS wherein:

X is $-CH_2-$, $-CH_2CH_2-$, or $-CH_2CH_2CH_2-$;

Y is $-CH_2-$ or O;

$Y_1$ is $-CH_2-$ or O;

wherein at least one of Y and $Y_1$ is $-CH_2-$;

$R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N—($C_{1-6}$alkyl)amino, N,N—($C_{1-6}$alkyl)$_2$ amino, $C_1$-$C_6$alkylcarbonylamino, $C_{1-6}$alkylS$(O)_a$ wherein a is 0-2, $C_{3-6}$cycloalkyl or aryl; and wherein any aryl group may be optionally substituted by one or two substituents selected from halo, hydroxy, $C_{1-6}$alkyl, and $C_{1-6}$alkoxy;

$R^2$ and $R^3$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl$C_{1-6}$alkoxy, ($C_1$-$C_4$ alkyl)$_3$Si, N—($C_{1-6}$alkyl)amino, N,N—($C_{1-6}$alkyl)$_2$amino, $C_{1-6}$alkylS$(O)_a$, $C_{3-6}$cycloalkyl, aryl or aryl$C_{1-6}$alkylS$(O)_a$, wherein a is 0-2; and wherein any aryl group may be optionally substituted by one or two substituents selected from halo, hydroxy, cyano, $C_{1-6}$alkyl, and $C_{1-6}$alkoxy;

$R^4$ is hydrogen, $C_{1-6}$ alkyl, or aryl$C_{1-6}$ alkyl;

wherein $R^3$ and $R^2$ may form a ring with 3-7 carbon atoms and wherein $R^4$ and $R^2$ may form a ring with 2-6 carbon atoms; and $R^5$ is selected from halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$ alkyl)sulphamoyl and N,N—($C_{1-6}$alkyl)$_2$sulphamoyl;

with an HMG Co-A reductase inhibitor.

18. A process for preparing a compound of formula (I)

(I)

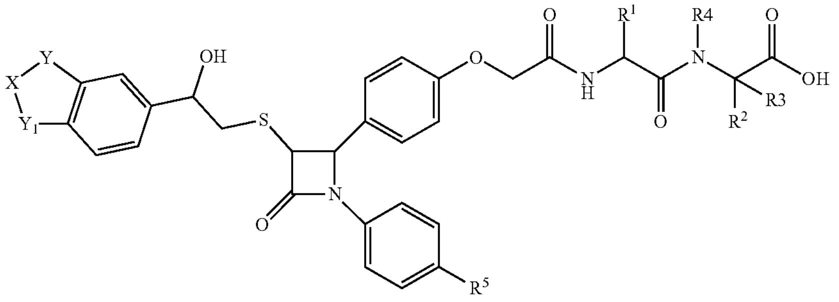

wherein:

X is —$CH_2$—, —$CH_2CH_2$—, or —$CH_2CH_2CH_2$—;

Y is —$CH_2$— or O;

$Y_1$ is —$CH_2$— or O;

wherein at least one of Y and $Y_1$ is —$CH_2$—;

$R^1$ is hydrogen, $C_{1-6}$alkyl, $C_{3-6}$cycloalkyl or aryl; wherein said $C_{1-6}$alkyl may be optionally substituted by one or more hydroxy, amino, guanidino, carbamoyl, carboxy, $C_{1-6}$alkoxy, N—($C_{1-6}$alkyl)amino, N,N—($C_{1-6}$alkyl)$_2$ amino, $C_1$-$C_6$alkylcarbonylamino, $C_{1-6}$alkylS(O)$_a$ wherein a is 0-2, $C_{3-6}$cycloalkyl or aryl; and wherein any aryl group may be optionally substituted by one or two substituents selected from halo, hydroxy, $C_{1-6}$alkyl, and $C_{1-6}$alkoxy;

$R^2$ and $R^3$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl$C_{1-6}$alkoxy, ($C_1$-$C_4$ alkyl)$_3$Si, N—($C_{1-6}$alkyl)amino, N,N—($C_{1-6}$alkyl)$_2$amino, $C_{1-6}$alkylS(O)$_a$, $C_{3-6}$cycloalkyl, aryl or aryl$C_{1-6}$alkylS(O)$_a$, wherein a is 0-2; and wherein any aryl group may be optionally substituted by one or two substituents selected from halo, hydroxy, cyano, $C_{1-6}$alkyl, and $C_{1-6}$alkoxy;

$R^4$ is hydrogen, $C_{1-6}$ alkyl, or aryl$C_{1-6}$ alkyl;

wherein $R^3$ and $R^2$ may form a ring with 3-7 carbon atoms and wherein $R^4$ and $R^2$ may form a ring with 2-6 carbon atoms; and $R^5$ is selected from halo, nitro, cyano, hydroxy, carboxy, carbamoyl, sulphamoyl, $C_{1-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$ alkyl)sulphamoyl and N,N—($C_{1-6}$alkyl)$_2$sulphamoyl;

or a pharmaceutically acceptable salt, or a prodrug thereof which process (wherein variable groups are, unless otherwise specified, as defined in formula (I)) comprising any of the steps of:

Process 1) reacting a compound of formula (II):

(II)

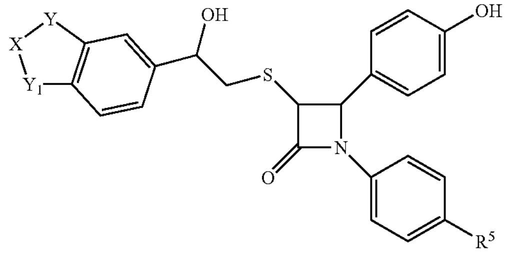

with a compound of formula (III):

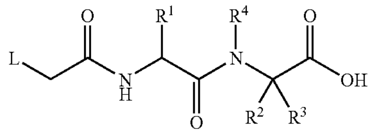

wherein L is a displaceable group; or

Process 2) reacting an acid of formula (IV):

(IV)

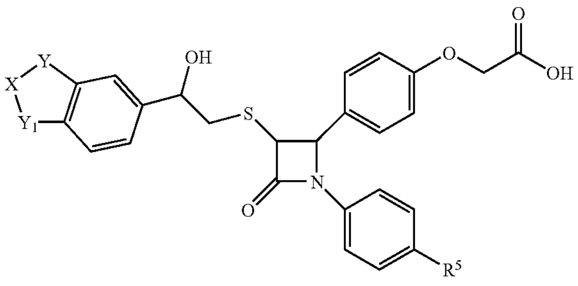

or an activated derivative thereof; with an amine of formula (V):

(V)

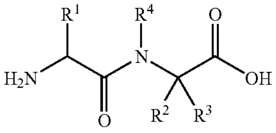

or

Process 3): reacting an acid of formula (VI):

(VI)

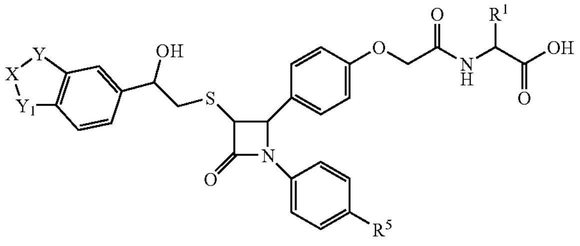

or an activated derivative thereof, with an amine of formula (VII):

(VII)

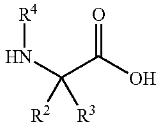

or

Process 4): reducing a compound of formula (VIII):

(VIII)

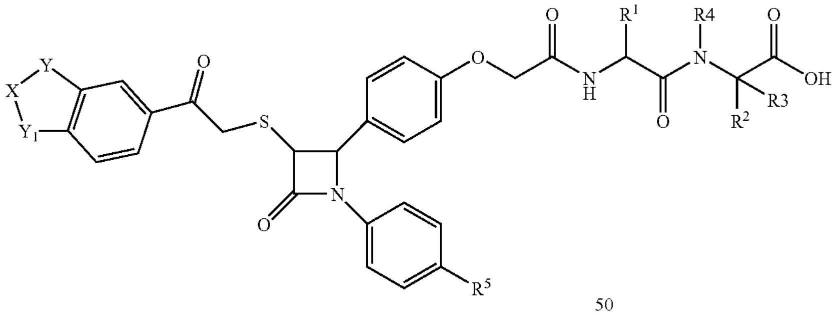

or

Process 5): reacting a compound of formula (IX):

(IX)

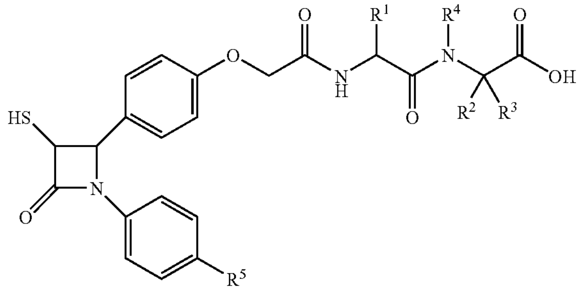

with a compound of formula (X):

(X)

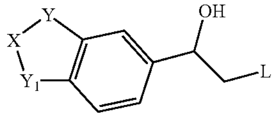

wherein L is a displaceable group; or

Process 6): reacting a compound of formula (X1):

(XI)

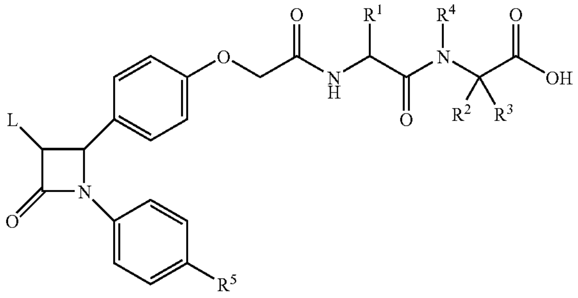

wherein L is a displaceable group; with a compound of formula (XII):

(XII)

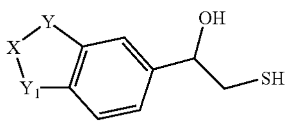

or

Process 7): De-esterifying a compound of formula (XIII)

(XIII)

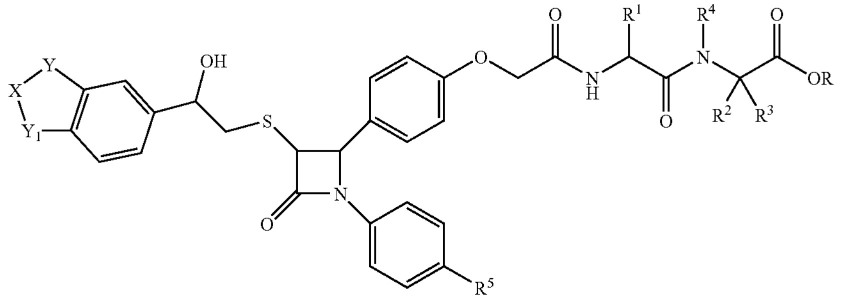

wherein the group C(O)OR is an ester group.

19. A compound according to claim 2, wherein X is —$CH_2$—.

20. A compound according to claim 2, wherein X is —$CH_2CH_2$—.

21. A compound according to claim 2, wherein X is —$CH_2CH_2CH_2$—.

22. A compound according to claim 2, wherein, $R^1$ is hydrogen;

$R^2$ and $R^3$ are, independently, hydrogen or a branched or unbranched $C_{1-6}$alkyl; wherein said $C_{1-6}$alkyl is substituted by $C_{3-6}$cycloalkyl, aryl or amino; and $R^4$ is hydrogen.

23. A compound according to claim 2 wherein, $R^1$ is hydrogen;

$R^2$ and $R^3$ are, independently, hydrogen or a branched or unbranched $C_{1-6}$alkyl; wherein said $C_{1-6}$alkyl is substituted by $C_{3-6}$cycloalkyl; and $R^4$ is hydrogen.

24. A compound according to claim 23, wherein, $R^2$ is hydrogen and $R^3$ is tert-butyl.

25. A compound according to claim 23, wherein, $R^2$ is hydrogen and $R^3$ is methyl; wherein said methyl is substituted by cyclolohexyl.

26. A compound according to claim 2, wherein, $R^5$ is chlorine or fluorine.

27. A method of treating or preventing hyperlipidemic conditions comprising the administration of an effective amount of a compound according to claim 2 to a mammal in need thereof.

28. A method of treating or preventing atherosclerosis comprising the administration of an effective amount of a compound according to claim 2 to a mammal in need thereof.

29. A pharmaceutical formulation comprising a compound according to claim 2 in admixture with a pharmaceutically acceptable adjuvant, diluent and/or carrier.

* * * * *